(12) United States Patent
Sun

(10) Patent No.: US 12,133,880 B2
(45) Date of Patent: *Nov. 5, 2024

(54) COMPOSITIONS AND METHODS FOR TREATMENT OF GCASE RELATED DISEASE STATES

(71) Applicant: Children's Hospital Medical Center, Cincinnati, OH (US)

(72) Inventor: Ying Sun, Mason, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 2 days.

This patent is subject to a terminal disclaimer.

(21) Appl. No.: 17/680,375

(22) Filed: Feb. 25, 2022

(65) Prior Publication Data

US 2023/0000948 A1 Jan. 5, 2023

Related U.S. Application Data

(60) Continuation of application No. 16/860,319, filed on Apr. 28, 2020, now Pat. No. 11,260,106, which is a division of application No. 15/896,423, filed on Feb. 14, 2018, now Pat. No. 10,675,328.

(60) Provisional application No. 62/458,628, filed on Feb. 14, 2017.

(51) Int. Cl.
| | |
|---|---|
| A61K 38/17 | (2006.01) |
| A61K 9/00 | (2006.01) |
| A61K 38/47 | (2006.01) |
| A61K 45/06 | (2006.01) |
| A61K 48/00 | (2006.01) |
| A61P 25/28 | (2006.01) |
| C12N 7/00 | (2006.01) |

(52) U.S. Cl.
CPC ........ *A61K 38/1777* (2013.01); *A61K 9/0019* (2013.01); *A61K 38/47* (2013.01); *A61K 45/06* (2013.01); *A61K 48/005* (2013.01); *A61P 25/28* (2018.01); *C12N 7/00* (2013.01); *C12Y 302/01045* (2013.01); *A01K 2227/105* (2013.01); *A01K 2267/0362* (2013.01); *A61K 48/00* (2013.01); *C12N 2740/15041* (2013.01); *C12N 2740/16043* (2013.01)

(58) Field of Classification Search
CPC .. A61K 38/1777; A61K 9/0019; A61K 38/47; A61K 45/06; A61K 48/005; A61K 48/00; A61P 25/28; C12N 7/00; C12N 2740/15041; C12N 2740/16043; C12Y 302/01045; A01K 2227/105; A01K 2267/0362

See application file for complete search history.

(56) References Cited

U.S. PATENT DOCUMENTS

| | | |
|---|---|---|
| 6,136,597 A | 10/2000 | Hope et al. |
| 6,284,469 B1 | 9/2001 | Hope et al. |
| 6,287,814 B1 | 9/2001 | Hope et al. |
| 6,312,912 B1 | 11/2001 | Hope et al. |
| 6,682,907 B1 | 1/2004 | Charneau et al. |
| 7,005,511 B2 | 2/2006 | Tsien et al. |
| 7,157,566 B2 | 1/2007 | Tsien et al. |
| 7,250,298 B2 | 7/2007 | Glick et al. |
| 7,393,923 B2 | 7/2008 | Tsien et al. |
| 9,260,725 B2 | 2/2016 | Trono et al. |
| 10,588,888 B2 | 3/2020 | Sun et al. |
| 10,675,328 B2 | 6/2020 | Sun |
| 10,751,387 B2 | 8/2020 | Sun et al. |
| 11,260,106 B2 | 3/2022 | Sun |
| 2016/0041149 A1 | 2/2016 | Lindquist et al. |
| 2020/0345808 A1 | 11/2020 | Sun et al. |

OTHER PUBLICATIONS

Adasme, T., et al., "Involvement of ryanodine receptors in neurotrophin-induced hippocampal synaptic plasticity and spatial memory formation," PNAS USA, 2011, 108:3029-3034, 6 pgs.
Aflaki, E., et al., "A New Glucocerebrosidase Chaperone Reduces α-Synuclein and Glycolipid Levels in iPSC-Derived Dopaminergic Neurons from Patients with Gaucher Disease and Parkinsonism," J Neurosci, 2016, 36(28):7441-7452, 12 pgs.
Alcalay, R.N., et al., "Glucocerebrosidase activity in Parkinson's disease with and without GBA mutations," Brain, 2015, 138(Pt 9):2648-2658, 11 pgs.
Alfonso, P., et al., "Mutation analysis and genotype/phenotype relationships of Gaucher disease patients in Spain," J Hum Genet, 2007, 52:391-396, 6 pgs.
Ali, F., et al., "Stem cells and the treatment of Parkinson's disease," Exp Neurol, 2014, 260:3-11, 9 pgs.
Alonso, M.T, et al., "Fura-2 antagonises calcium-induced calcium release," Cell Calcium, 2003, 33:27-35, 9 pgs.
Ashe, K.M., et al., "Iminosugar-based inhibitors of glucosylceramide synthase increase brain glycosphingolipids and survival in a mouse model of Sandhoff disease," PLoS One, 2011, 6(6):e21758, 11 pgs.

(Continued)

*Primary Examiner* — Kimberly Ballard
*Assistant Examiner* — Stacey N Macfarlane
(74) *Attorney, Agent, or Firm* — Frost Brown Todd LLP

(57) ABSTRACT

Disclosed are compositions and methods of treating a neurodegenerative disease in an individual. The methods disclose administration of an Integrin α4β1, Very Late Antigen-4 positive neural precursor cell ("VLA4+NPC") transfected with a lentivirus overexpressing wild type GCase to an individual having a neurodegenerative disorder. The neurodegenerative disease may include lipid storage diseases, for example Gaucher disease, Parkinson's disease (PD), Dementia with Lewy bodies.

11 Claims, 47 Drawing Sheets

Specification includes a Sequence Listing.

(56) References Cited

OTHER PUBLICATIONS

Aymami, J., et al., "Pharmacological chaperones for enzyme enhancement therapy in genetic diseases," Pharm Pat Anal, 2013, 2(1):109-124, 16 pgs.

Bading, H., et al., "Regulation of gene expression in hippocampal neurons by distinct calcium signaling pathways," Science. 1993, 260:181-186, 8 pgs.

Bae, E-J., et al., "Loss of glucocerebrosidase 1 activity causes lysosomal dysfunction and α-synuclein aggregation," Exp Mol Med, 2015, 47:e153, 8 pgs.

Balaban, R.S., "The role of $Ca^{2+}$ signaling in the coordination of mitochondrial ATP production with cardiac work," Biochim. Biophys. Acta., 2009, 1787:1334-1341, 20 pgs.

Bendikov-Bar, I., et al., "Ambroxol as a pharmacological chaperone for mutant glucocerebrosidase," Blood Cells Mol Dis, 2013, 50(2):141-145, 5 pgs.

Bito, H., et al., "CREB Phosphorylation and Dephosphorylation: a $Ca^{2+}$- and Stimulus Duration-Dependent Switch for Hippocampal Gene Expression," Cell, 1996, 87:1203-1214, 12 pgs.

Blanz, J., et al., "Parkinson's disease: acid-glucocerebrosidase activity and alpha-synuclein clearance," J Neurochem, 2016, 139(Suppl. 1):198-215, 18 pgs.

Blaya, M.O., et al., "Neural Progenitor Cell Transplantation Promotes Neuroprotection, Enhances Hippocampal Neurogenesis, and Improves Cognitive Outcomes after Traumatic Brain Injury," Exp Neurol, 2015, 264: 67-81, 29 pgs.

Bouchard, R., et al., "Presence and functional significance of presynaptic ryanodine receptors," Prog. Neurobiol, 2003, 69:391-418, 28 pgs.

Bround, M.J., et al., "Cardiomyocyte ATP Production, Metabolic Flexibility, and Survival Require Calcium Flux Through Cardiac Ryanodine Receptors in Vivo," J. Biol. Chem, 2013, 288(26):18975-18986, 12 pgs.

Brown, M.W., et al., "Recognition Memory: Material, Processes, and Substrates," Hippocampus, 2010, 20(11):1228-1244, 17 pgs.

Burrow, T.A., et al. "CNS, lung, and lymph node involvement in Gaucher disease type 3 after 11years of therapy: Clinical, histopathologic, and biochemical findings," Mol. Genet. Metab, 2015, 114:233-241, 9 pgs.

Cabrera-Salazar, M.A. et al., "Systemic Delivery of a Glucosylceramide Synthase Inhibitor Reduces CNS Substrates and Increases Lifespan in a Mouse Model of Type 2 Gaucher Disease," PLoS One, 2012, 7(8):e43310, 9 pgs.

Cervos-Navarro, J, et al. "Light microscopic and ultrastructural study on CNS lesions in infantile Gaucher's disease," Clin Neuropathol, 1990, 9(6):310-313, 4 pgs.

Chakraborty, S., et al., "The Interaction Affinity between Vascular Cell Adhesion Molecule-1 (VCAM-1) and Very Late Antigen-4 (VLA-4) Analyzed by Quantitative FRET," PLoS One, 2015, 10(3):e0121399, 15 pgs.

Chakroborty, S., et al., "Stabilizing ER $Ca^{2+}$ Channel Function as an Early Preventative Strategy for Alzheimer's Disease," PLoS One, 2012, 7:e52056, 12 pgs.

Chandler, R.J., et al., "Systemic AAV9 gene therapy improves the lifespan of mice with Niemann-Pick disease, type C1," Human Molecular Genetics, 2016, 26(1):52-64, 13 pgs.

Chen, B., et al., "Dynamic Imaging of Genomic Loci in Living Human Cells by an Optimized CRISPR/Cas System," Cell, 2013, 155:1479-1491, 23 pgs.

Chen, X., et al., "Dantrolene is neuroprotective in Huntington's disease transgenic mouse model," Mol. Neurodegener, 2011, 6:81, 12 pgs.

Chidlow, G., et al., "Evaluation of Fluoro-Jade C as a marker of degenerating neurons in the rat retina and optic nerve," Exp Eye Res, 2009, 88:426-37, 12 pgs.

Choi, S., et al., "Lysosomal Enzyme Glucocerebrosidase Protects against $A\beta_{1-42}$ Oligomer-Induced Neurotoxicity," PLoS one, 2015, 10(12):e0143854, 18 pgs.

Chow, F.A., et al., "The Autonomous Activity of Calcium/Calmodulin-Dependent Protein Kinase IV is Required for Its Role in Transcription," J. Biol. Chem., 2005, 280:20530-20538, 9 pgs.

Choy, F.Y.M., et al., "Gaucher disease among Chinese patients: Review on genotype/phenotype correlation from 29 patients and identification of novel and rare alleles," Blood Cells Mol Dis, 2007, 38:287-293, 7 pgs.

Cleeter, M.W.J., et al., "Glucocerebrosidase inhibition causes mitochondrial dysfunction and free radical damage," Neurochem. Int., 2013, 62:1-7, 7 pgs.

Clinical Trial of Ambroxol in Patients with Type I Gaucher Disease, Identifier: NCT01463215, by Exsar Corporation, ClinicalTrials. gov, Nov. 2011-Feb. 2013, 12 pgs.

Cochrane, A.W., et al., "Specific interaction of the human immunodeficiency virus Rev protein with a structured region in the env mRNA," PNAS USA, 1990, 87(3):1198-1202, 5 pgs.

Conradi, N.G., et al., "Neuropathology of the Norrbottnian Type of Gaucher Disease: Morphological and Biochemical Studies," Acta Neuropathol., 1984, 65:99-109, 11 pgs.

Corti, S., et al., "Transplanted $ALDH^{hi}SSC^{lo}$ neural stem cells generate motor neurons and delay disease progression of nmd mice, an animal model of SMARD1," Hum Mol Genet, 2006, 15(2):167-187, 21 pgs.

Cullen, V., et al., "Acid β-Glucosidase Mutants Linked to Gaucher Disease, Parkinson Disease, and Lewy Body Dementia Alter α-Synuclein Processing," Ann Neurol, 2011, 69(6): 940-953, 14 pgs.

Dai, M., et al., "Progression of Behavioral and CNS Deficits in a Viable Murine Model of Chronic Neuronopathic Gaucher Disease," PLoS one, 2016, 11(9):e0162367, 23 pgs.

Dasgupta, N., et al., "Neuropathic Gaucher disease: dysregulated mRNAs and miRNAs in brain pathogenesis and effects of pharmacologic chaperone treatment in a mouse model," Hum Mol Genet, 2015, 24:7031-48, 18 pgs.

De Feo, D., et al., "Neural stem cell transplantation in central nervous system disorders: from cell replacement to neuroprotection," Curr Opin Neurol, 2012, 25(3):322-333, 12 pgs.

Del Prete, D., et al., "Ryanodine receptors: physiological function and deregulation in Alzheimer disease," Mol. Neurodegener., 2014, 9:21, 15 pgs.

Denton, R.M., "Regulation of mitochondrial dehydrogenases by calcium ions," Biochim. Biophys. Acta., 2009, 1787:1309-1316, 8 pgs.

Depaolo, J., et al., "The Association Between Mutations in the Lysosomal Protein Glucocerebrosidase and Parkinsonism," Movement Disorders: Official Journal of the Movement Disorder Society, 2009, 24(11):1571-1578, 8 pgs.

Elrick, M.J., et al., "Impaired proteolysis underlies autophagic dysfunction in Niemann-Pick type C disease," Hum. Mol. Genet., 2012, 21(22):4876-4887, 12 pgs.

Enokizono, J., et al., "Quantitative Investigation of the Role of Breast Cancer Resistance Protein (Bcrp/Abcg2) in Limiting Brain and Testis Penetration of Xenobiotic Compounds," Drug Metab. Dispos., 2008, 36(6):995-1002, 8 pgs.

Ferreiro, E., et al., "Involvement of Endoplasmic Reticulum $Ca^{2+}$ Release Through Ryanodine and Inositol 1,4,5-Triphosphate Receptors in the Neurotoxic Effects Induced by the Amyloid-βPeptide," J. Neurosci. Res., 2004, 76:872-880, 9 pgs.

Fleming, S.M., et al., "A pilot trial of the microtubule-interacting peptide (NAP) in mice overexpressing alpha-synuclein shows improvement in motor function and reduction of alpha-synuclein inclusions," Mol Cell Neurosci, 2011, 46(3):597-606, 24 pgs.

Fleming, S.M., et al., "Early and Progressive Sensorimotor Anomalies in Mice Overexpressing Wild-Type Human α-Synuclein," J. Neurosci., 2004, 24(42):9434-9440, 7 pgs.

Fruen, B.R., et al., "Dantrolene Inhibition of Sarcoplasmic Reticulum $Ca^{2+}$ Release by Direct and Specific Action at Skeletal Muscle Ryanodine Receptors," J. Biol. Chem., 1997, 272(43):26965-26971, 7 pgs.

Fruen, B.R., et al., "Differential $Ca^{2+}$ sensitivity of skeletal and cardiac muscle ryanodine receptors in the presence of calmodulin," Am. J. Physiol. Cell Physiol., 2000, 279:C724-733, 10 pgs.

(56) References Cited

OTHER PUBLICATIONS

Furuichi, T., et al., "Multiple Types of Ryanodine Receptor/$Ca^{2+}$ Release Channels are Differentially Expressed in Rabbit Brain," J. Neurosci., 1994, 14(8):4794-4805, 12 pgs.

Gennaro, A.R., Ed., *Remington's Pharmaceutical Sciences*, 18th Ed., Mack Publ. Co., Easton, PA, 1990, 8 pgs.

Ghislat, G., et al., "Withdrawal of Essential Amino Acids Increases Autophagy by a Pathway Involving $Ca^{2+}$/Calmodulin-dependent Kinase Kinase-β (CaMKK-β)," J. Biol. Chem., 2012, 287(46):38625-38636, 12 pgs.

Giannini, G., et al., "Molecular Structure and Tissue Distribution of Ryanodine Receptors Calcium Channels," Med. Res. Rev., 1995, 15(4):313-323, 11 pgs.

Gilbert, S., et al., "Activated STAT5 Confers Resistance to Intestinal Injury by Increasing Intestinal Stem Cell Proliferation and Regeneration," Stem Cell Reports, 2015, 4(2):209-225, 17 pgs.

Ginzburg, L. et al., "Defective calcium homeostasis in the cerebellum in a mouse model of Niemann-Pick A disease," J. Neurochem., 2005, 95:1619-1628, 10 pgs.

Gong, Y., et al., "Adenoassociated Virus Serotype 9-Mediated Gene Therapy for X-Linked Adrenoleukodystrophy," Mol Ther, 2015, 23(5):824-834, 11 pgs.

Gonzalez, F., et al., "An iCRISPR platform for rapid, multiplexable, and inducible genome editing in human pluripotent stem cells," Cell Stem Cell, 2014, 15(2):215-226, 27 pgs.

Gorelik, M., et al., "Use of MR Cell Tracking to Evaluate Targeting of Glial Precursor Cells to Inflammatory Tissue by Exploiting the Very Late Antigen-4 Docking Receptor," Radiology, 2012, 265(1):175-185, 11 pgs.

Grabowski, G.A., et al., "146: Gaucher Disease," The Online Metabolic and Molecular Bases of Inherited Diseases, (eds. Valle, D., Beaudet, A., Vogelstein, B., Kinzler, K.W., Antonarakis, S.E., Ballabio, A., Scriver, C.R., Sly, W.S., Childs, B., Bunz, F., Gibson, K.M. and Mitchell, G.), The McGraw-Hill Companies, Inc., New York, 2010, 107 pgs.

Grabowski, G.A., et al., "Gaucher disease types 1 and 3: Phenotypic characterization of large populations from the ICGG Gaucher Registry," Am J Hematol., Jul. 2015, 90(Suppl 1):S12-8, 7 pgs.

Grotemeier, A., et al., "AMPK-independent induction of autophagy by cytosolic $Ca^{2+}$ increase," Cell Signal, 2010, 22:914-925, 12 pgs.

Guzman, R., et al., "Intracarotid Injection of Fluorescence Activated Cell-Sorted CD49d-Positive Neural Stem Cells Improves Targeted Cell Delivery and Behavior After Stroke in a Mouse Stroke Model," Stroke, 2008, 39(4):1300-1306, 7 pgs.

Hickey, W.F., "Basic Principles of Immunological Surveillance of the Normal Central Nervous System," GLIA, 2001, 36:118-124, 7 pgs.

Huang, X., et al., "Production of gene-corrected adult beta globin protein in human erythrocytes differentiated from patient iPSCs after genome editing of the sickle point mutation," Stem Cells, 2015, 33(5):1470-1479, 21 pgs.

Jang, S.K., et al., "A Segment of the 5' Nontranslated region of Encephalomyocarditis Virus RNA Directs Internal Entry of Ribosomes during In Vitro Translation," J Virol, 1988, 62(8):2636-2643, 8 pgs.

Jennings, J.J., Jr., et al., "Mitochondrial Aberrations in Mucolipidosis Type IV," J. Biol. Chem., 2006, 281(51):39041-39050, 10 pgs.

Kaye, E.M., et al., "Type 2 and Type 3 Gaucher Disease: A Morphological and Biochemical Study," Ann. Neurol., 1986, 20(2):223-230, 8 pgs.

Kerfoot, S.M., et al., "Reevaluation of P-Selectin and $α_4$ Integrin as Targets for the Treatment of Experimental Autoimmune Encephalomyelitis," J Immunol, 2006, 176(10):6225-6234, 10 pgs.

Khanna, R., et al., "The pharmacological chaperone isofagomine increases the activity of the Gaucher disease L444P mutant form of β-glucosidase," FEBS J, 2010, 277(7):1618-1638, 21 pgs.

Kilpatrick, B.S., et al., "Endoplasmic reticulum and lysosomal $Ca^{2+}$ stores are remodelled in GBA1-linked Parkinson disease patient fibroblasts," Cell Calcium, 2015, 59:12-20, 9 pgs.

Kiselyov, K., et al., "Aberrant $Ca^{2+}$ handling in lysosomal storage disorders," Cell Calcium., 2010, 47:103-111, 9 pgs.

Klegeris A., et al., "Functional Ryanodine Receptors Are Expressed by Human Microglia and THP-1 Cells: Their Possible Involvement in Modulation of Neurotoxicity," J Neurosci Res., Aug. 1, 2007, 85(10):2207-15, 9 pgs.

Kohn, D.B., et al., "Toward Gene Therapy for Gaucher Disease," Human Gene Therapy, 1991, 2:101-105, 5 pgs.

Koprivica, V., et al., "Analysis and Classification of 304 Mutant Alleles in Patients with Type 1 and Type 3 Gaucher Disease," Am J Hum Genet, 2000, 66:1777-1786, 10 pgs.

Korkotian, E., et al., "Elevation of Intracellular Glucosylceramide Levels Results in an Increase in Endoplasmic Reticulum Density and in Functional Calcium Stores in Cultured Neurons," J. Biol. Chem., 1999, 274(31):21673-21678, 6 pgs.

Krause, T., et al., "Dantrolene—A review of its pharmacology, therapeutic use and new developments," Anaesthesia, 2004, 59:364-373, 10 pgs.

Kuter, D.J., et al., "Miglustat therapy in type 1 Gaucher disease: Clinical and safety outcomes in a multicenter retrospective cohort study," Blood Cells Mol. Dis., 2013, 51: 116-124, 9 pgs.

Larsen, J.M., et al., "Recent Advances in Delivery Through the Blood-Brain Barrier," Curr Top Med Chem, 2014, 14:1148-1160, 13 pgs.

Lee, Y-H., et al., "Stem Cells Expressing Homing Receptors Could be Expanded From Cryopreserved and Unselected Cord Blood," J Korean Med Sci, 2004, 19:635-639, 5 pgs.

Lim, J-A., et al., "Defects in calcium homeostasis and mitochondria can be reversed in Pompe disease," Autophagy, 2015, 11(2):385-402, 18 pgs.

Liou, B., et al., "Analyses of Variant Acid β-Glucosidases: Effects of Gaucher Disease Mutations," J Biol Chem, 2006, 281:4242-53, 12 pgs.

Liou, B., et al., "Modulating ryanodine receptors with dantrolene attenuates neuronopathic phenotype in Gaucher disease mice," Hum Mol Genet, 2016, 25:5126-5141, 16 pgs.

Lloyd-Evans, E., et al., "Niemann-Pick disease type C1 is a sphingosine storage disease that causes deregulation of lysosomal calcium," Nat. Med., 2008, 14(11):1247-1255, 10 pgs.

Lukina, E., et al., "Eliglustat, an investigational oral therapy for Gaucher disease type 1: Phase 2 trial results after 4 years of treatment," Blood Cells Mol. Dis., 2014, 53:274-276, 3 pgs.

Lunn, J., et al., "Stem Cell Technology for Neurodegenerative Diseases," Ann Neurol, 2011, 70(3):353-361, 15 pgs.

Mali, P., et al., "RNA-Guided Human Genome Engineering via Cas9," Science, 2013, 339(6121):823-826, 8 pgs.

Malik, Z.A., et al., "Mission CaMKIIγ: Shuttle Calmodulin from Membrane to Nucleus," Cell, 2014, 159:235-237, 3 pgs.

Marshall, J., et al., "Improved management of lysosomal glucosylceramide levels in a mouse model of type 1 Gaucher disease using enzyme and substrate reduction therapy," J Inherit Metab Dis, 2010, 33(3):281-289, 16 pgs.

Marshall, J., et al., "CNS-accessible Inhibitor of Glucosylceramide Synthase for Substrate Reduction Therapy of Neuronopathic Gaucher Disease," Mol. Ther., 2016, 24(6):1019-1029, 11 pgs.

Marugan, J.J., et al., "Non-iminosugar glucocerebrosidase small molecule chaperones," MedChemComm, 2012, 3(1):56-60, 5 pgs.

Mazzulli, J.R., et al., "Gaucher's Disease Glucocerebrosidase and α-synuclein form a bidirectional pathogenic loop in synucleinopathies," Cell, 2011, 146(1):37-52, 28 pgs.

Mbaya, E., et al., "Calcium signalling-dependent mitochondrial dysfunction and bioenergetics regulation in respiratory chain Complex II deficiency," Cell Death Differ., 2010, 17:1855-1866, 12 pgs.

Mehra, D., et al., "Multiple Modes of Ryanodine Receptor 2 Inhibition by Flecainide," Mol Pharmacol., Dec. 2014., 86(6):696-706, 11 pgs.

Mu, T.-W., et al., "Partial Restoration of Mutant Enzyme Homeostasis in Three Distinct Lysosomal Storage Disease Cell Lines by Altering Calcium Homeostasis," PLoS Biol., 2008, 6(2):e26, 13 pgs.

Muehlschlegel, S. et al., "Dantrolene: mechanisms of neuroprotection and possible clinical applications in the neurointensive care unit," Neurocrit. Care., 2009, 10(1):103-115, 19 pgs.

(56) References Cited

OTHER PUBLICATIONS

Murphy, K.E., et al., "Reduced glucocerebrosidase is associated with increased α-synuclein in sporadic Parkinson's disease," Brain, 2014, 137(Pt 3):834-848, 15 pgs.

Nietupski, J.B., et al., "Iminosugar-based inhibitors of glucosylceramide synthase prolong survival but paradoxically increase brain glucosylceramide levels in Niemann-Pick C mice," Mol. Genet. Metab., 2012, 105:621-628, 8 pgs.

Nilsson, O., et al., "Accumulation of Glucosylceramide and Glucosylsphingosine (Psychosine) in Cerebrum and Cerebellum in Infantile and Juvenile Gaucher Disease," J. Neurochem., 1982, 39:709-718, 6 pgs.

Nizzardo, M., et al., "Minimally invasive transplantation of iPSC-derived ALDHhiSSClo VLA4+ neural stem cells effectively improves the phenotype of an amyotrophic lateral sclerosis model," Human Molecular Genetics, 2014, 23(2):342-354, 13 pgs.

Ong, D.S., et al., "Endoplasmic Reticulum $Ca^{2+}$ Increases Enhance Mutant Glucocerebrosidase Proteostasis," Nat. Chem. Biol., 2010, 6(6):424-432, 22 pgs.

Orvisky, E., et al., "Glucosylsphingosine accumulation in tissues from patients with Gaucher disease: correlation with phenotype and genotype," Mol. Genet. Metab., 2002, 76:262-270, 9 pgs.

Osellame, L.D. et al., "Defective quality control mechanisms and accumulation of damaged mitochondria link Gaucher and Parkinson diseases," Autophagy, 2013, 9(10):1633-1635, 3 pgs.

Osellame, L.D., et al., "Mitochondria and Quality Control Defects in a Mouse Model of Gaucher Disease—Links to Parkinson's Disease," Cell Metab., 2013, 17:941-953, 13 pgs.

Ostrovskaya, O., et al., "Inhibition of Ryanodine Receptors by 4-(2-Aminopropyl)-3,5-dichloro-N,N-dimethylaniline (FLA 365) in Canine Pulmonary Arterial Smooth Muscle Cells," Journal of Pharmacology and Experimental Therapeutics, Oct. 2007, 323(1):381-390, 10 pgs.

Oules, B., et al., "Ryanodine receptor blockade reduces amyloid-beta load and memory impairments in Tg2576 mouse model of Alzheimer disease," J. Neurosci., 2012, 32(34):11820-11834, 38 pgs.

Ozawa, T., "Modulation of ryanodine receptor $Ca^{2+}$ channels (Review)," Mol. Med. Rep., 2010, 3:199-204, 6 pgs.

Parenti, G., "Treating lysosomal storage diseases with pharmacological chaperones: from concept to clinics," EMBO Mol Med, 2009, 1:268-279, 12 pgs.

Patnaik, S., et al., "Discovery, Structure-Activity Relationship, and Biological Evaluation of Noninhibitory Small Molecule Chaperones of Glucocerebrosidase," J Med Chem, 2012, 55(12):5734-5748, 15 pgs.

Pelled, D., et al., "Enhanced calcium release in the acute neuronopathic form of Gaucher disease," Neurobiol. Dis., 2005, 18:83-88, 6 pgs.

Pelled, D., et al., "Inhibition of Calcium Uptake via the Sarco/Endoplasmic Reticulum $Ca^{2+}$-ATPase in a Mouse Model of Sandhoff Disease and Prevention by Treatment with N-Butyldeoxynojirimycin," J. Biol. Chem., 2003, 278(32):29496-29501, 6 pgs.

Pluchino, S., et al., "Neurosphere-derived multipotent precursors promote neuroprotection by an immunomodulatory mechanism," Nature, 2005, 436(7048):266-271, 6 pgs.

Pluchino, S., et al., "Injection of adult neurospheres induces recovery in a chronic model of multiple sclerosis," Nature, 2003, 422:688-694, 7 pgs.

Popescu, B.O., et al., "Dantrolene protects neurons against kainic acid induced apoptosis in vitro and in vivo," J. Cell Mol. Med., 2002, 6(4):555-569, 15 pgs.

Ran, F.A., et al., "Genome engineering using the CRISPR-Cas9 system," Nature Protocols, Nov. 2013, 8(11):2281-2308, 49 pgs.

Reitz, M., et al., "Intranasal delivery of neural stem/progenitor cells: a noninvasive passage to target intracerebral glioma," Stem Cells Transl Med, 2012 1:866-873, 8 pgs.

Richter, F., et al., "A GCase Chaperone Improves Motor Function in a Mouse Model of Synucleinopathy," Neurotherapeutics, 2014, 11(4):840-856, 17 pgs.

Rigat, B. et al., "Diltiazem, a L-type $Ca^{2+}$ channel blocker, also acts as a pharmacological chaperone in Gaucher patient cells," Mol. Genet. Metab., 2009, 96(4):225-232, 18 pgs.

Rocha, E.M., et al., "Glucocerebrosidase gene therapy prevents α-synucleinopathy of midbrain dopamine neurons" Neurobiol Dis, 2015, 82:495-503, 9 pgs.

Rockenstein, E., et al., "Glucocerebrosidase modulates cognitive and motor activities in murine models of Parkinson's disease," Human Molecular Genetics, 2016, 25(13):2645-2660, 16 pgs.

Rockenstein, E., et al. "Differential Neuropathological Alterations in Transgenic Mice Expressing α-synuclein From The Platelet-Derived Growth Factor and Thy-1 Promoters," J Neurosci Res, 2002, 68(5):568-578, 11 pgs.

Rogers, G.W., et al., "High Throughput Microplate Respiratory Measurements Using Minimal Quantities of Isolated Mitochondria," PLoS One, 2011, 6(7):e21746, 12 pgs.

Sa, Q., et al., "VCAM-1/α4β1 Integrin Interaction Is Crucial for Prompt Recruitment of Immune T Cells into the Brain during the Early Stage of Reactivation of Chronic Infection with *Toxoplasma gondii* To Prevent Toxoplasmic Encephalitis," Infect Immun, 2014, 82(7):2826-2839, 14 pgs.

Sardi, S.P., et al., "CNS expression of glucocerebrosidase corrects α-synuclein pathology and memory in a mouse model of Gaucher-related synucleinopathy," PNAS USA, 2011, 108(29):12101-12106, 6 pgs.

Sardi, S.P., et al., "Augmenting CNS glucocerebrosidase activity as a therapeutic strategy for parkinsonism and other Gaucher-related synucleinopathies," PNAS USA, 2013, 110(9):3537-3542, 6 pgs.

Sawkar, A.R., et al., "Gaucher Disease-Associated Glucocerebrosidases Show Mutation-Dependent Chemical Chaperoning Profiles," Chem. Biol., 2005, 12:1235-1244, 10 pgs.

Schindelin, J., et al., "Fiji—an Open Source platform for biological-image analysis," Nat. Methods, 2012, 9(7):676-682, 15 pgs.

Schondorf, D.C., et al., "iPSC-derived neurons from GBA1-associated Parkinson's disease patients show autophagic defects and impaired calcium homeostasis," Nat. Commun., 2014, 5:4028, 17 pgs.

Schultheis, P.J., et al., "Atp13a2-deficient mice exhibit neuronal ceroid lipofuscinosis, limited α-synuclein accumulation and age-dependent sensorimotor deficits," Hum. Mol. Genet., 2013, 22(10):2067-2082, 16 pgs.

Settembre, C., et al., "A block of autophagy in lysosomal storage disorders," Hum. Mol. Genet., 2008, 17(1):119-129, 11 pgs.

Shaner, N.C., et al., "Improved monomeric red, orange and yellow fluorescent proteins derived from *Discosoma* sp. red fluorescent protein," Nat Biotechnol, 2004, 22(12):1567-1572, 6 pgs.

Shechter, R., et al., "Recruitment of Beneficial M2 Macrophages to Injured Spinal Cord Is Orchestrated by Remote Brain Choroid Plexus," Immunity, 2013, 38(3):555-569, 26 pgs.

Sidransky, E., et al., "Multicenter Analysis of Glucocerebrosidase Mutations in Parkinson's Disease," N Engl J Med, 2009, 361(17):1651-1661, 11 pgs.

Simone, C., et al., "iPSC-Derived Neural Stem Cells Act via Kinase Inhibition to Exert Neuroprotective Effects in Spinal Muscular Atrophy with Respiratory Distress Type 1," Stem Cell Reports, 2014, 3(2):297-311, 15 pgs.

Soderling, T.R., "The $Ca^{2+}$-calmodulin-dependent protein kinase cascade," Trends Biochem. Sci., 1999, 24:232-236, 5 pgs.

Stone, D.L., et al., "Glucocerebrosidase Gene Mutations in Patients With Type 2 Gaucher Disease," Hum Mutat, 2000, 15:181-188, 8 pgs.

Sun, Y., et al., "Tissue-specific effects of saposin A and saposin B on glycosphingolipid degradation in mutant mice," Hum Mol Genet, 2013, 22(12):2435-2450, 16 pgs.

Sun, Y., et al., "Ex Vivo and In Vivo Effects of Isofagomine on Acid β-Glucosidase Variants and Substrate Levels in Gaucher Disease," J Biol Chem, 2012, 287(6):4275-4287, 13 pgs.

Sun, Y., et al., "Gaucher disease mouse models: point mutations at the acid β-glucosidase locus combined with low-level prosaposin expression lead to disease variants," J. Lipid Res., 2005, 46:2102-2113, 12 pgs.

(56) References Cited

OTHER PUBLICATIONS

Sun, Y., et al., "Impaired autophagosomes and lysosomes in neuronopathic Gaucher disease," Autophagy, 2010, 6(5):648-649, 2 pgs.
Sun, Y., et al., "In Vivo and Ex Vivo Evaluation of L-Type Calcium Channel Blockers on Acid β-Glucosidase in Gaucher Disease Mouse Models," PLoS One, 2009, 4(10):e7320, 8 pgs.
Sun, Y., et al., "Isofagomine In Vivo Effects in a Neuronopathic Gaucher Disease Mouse," PLoS One, 2011, 6(4):e19037, 12 pgs.
Sun, Y., et al., "Neuronopathic Gaucher disease in the mouse: viable combined selective saposin C deficiency and mutant glucocerebrosidase (V394L) mice with glucosylsphingosine and glucosylceramide accumulation and progressive neurological deficits," Hum. Mol. Genet., 2010, 19(6):1088-1097, 10 pgs.
Sun, Y., et al., "Properties of Neurons Derived from Induced Pluripotent Stem Cells of Gaucher Disease Type 2 Patient Fibroblasts: Potential Role in Neuropathology," PLoS One, 2015, 10(3):e0118771, 20 pgs.
Sun, Y., et al., "Substrate Compositional Variation with Tissue/Region and Gbal Mutations in Mouse Models—Implications for Gaucher Disease," PLoS One, 2013, 8(3):e57560, 14 pgs.
Sundberg, M., et al., "Improved cell therapy protocols for Parkinson's disease based on differentiation efficiency and safety of hESC-, hiPSC-, and non-human primate iPSC-derived DA neurons," Stem Cells, 2013, 31(8):1548-1562, 27 pgs.
Tabata, H., et al., "Efficient In Utero Gene Transfer System to the Developing Mouse Brain Using Electroporation: Visualization of Neuronal Migration in the Developing Cortex," Neuroscience, 2001, 103(4):865-872, 8 pgs.
Tantawy, A.A., et al., "Evoked potentials and neurocognitive functions in pediatric Egyptian Gaucher patients on enzyme replacement therapy: a single center experience," J. Inherit. Metab. Dis., 2013, 36:1025-1037, 13 pgs.
Tremblay, R.G., et al., "Differentiation of mouse Neuro 2A cells into dopamine neurons," J. Neurosci. Methods, 2010, 186:60-67, 8 pgs.
Tsuchiya, R., et al., "Cell type-selective expression of green fluorescent protein and the calcium indicating protein, yellow cameleon, in rat cortical primary cultures," Brain Res., 2002, 956(2):221-229, 9 pgs.
Tsuji, S., et al., "A Mutation in the Human Glucocerebrosidase Gene in Neuronopathic Gaucher's Disease," N Engl J Med, 1987, 316(10):570-575, 6 pgs.
Vitner, E.B., et al., "RIPK3 as a potential therapeutic target for Gaucher's disease," Nat. Med., 2014, 20(2):204-208, 6 pgs.
Wang, F., et al., "$Ca^{2+}$ Homeostasis Modulation Enhances the Amenability of L444P Glucocerebrosidase to Proteostasis Regulation in Patient-Derived Fibroblasts," ACS Chem. Biol., 2011, 6:158-168, 11 pgs.
Wang, R., et al., "Promoter-Dependent Enhanced Green Fluorescent Protein Expression During Embryonic Stem Cell Propagation and Differentiation," Stem Cells Dev, 2008, 17(2):279-289, 11 pgs.
Watson, C.L., et al., "An in vivo model of human small intestine using pluripotent stem cells," Nat Med, 2014, 20(11):1310-1314, 16 pgs.
Watson, M.B., et al., "Regionally-specific microglial activation in young mice over-expressing human wildtype alpha-synuclein," Exp Neurol, 2012, 237(2):318-334, 34 pgs.
Wehrens, X.H.T., et al., "Protection from Cardiac Arrhythmia Through Ryanodine Receptor-Stabilizing Protein Calstabin2," Science, 2004, 304(5668):292-6, 5 pgs.
Wernig, M., et al., "Neurons derived from reprogrammed fibroblasts functionally integrate into the fetal brain and improve symptoms of rats with Parkinson's disease," PNAS USA, 2008, 105(15):5856-5861, 6 pgs.
Wigderson, M., et al., "Characterization of Mutations in Gaucher Patients by cDNA Cloning," Am J Hum Genet, 1989, 44:365-377, 13 pgs.
Williams, I.M., et al., "Improved neuroprotection using miglustat, curcumin and ibuprofen as a triple combination therapy in Niemann-Pick disease type C1 mice," Neurobiol. Dis., 2014, 67:9-17, 9 pgs.
Wong, K., et al., "Neuropathology provides clues to the pathophysiology of Gaucher disease," Mol. Genet. Metab., 2004, 82(3):192-207, 16 pgs.
Wu, Y-P., et al., "Deletion of macrophage-inflammatory protein la retards neurodegeneration in Sandhoff disease mice," PNAS USA, 2004, 101(22):8425-8430, 6 pgs.
Wu, X., et al., "Development of a Novel Trans-Lentiviral Vector That Affords Predictable Safety," Mol Ther, 2000, 2(1):47-55, 9 pgs.
Xu, Y-H., et al., "Accumulation and distribution of α-synuclein and ubiquitin in the CNS of Gaucher disease mouse models," Mol Genet Metab, 2011, 102(4):436-447, 12 pgs.
Xu, Y-H., et al., "Comparative Therapeutic Effects of Velaglucerase Alfa and Imiglucerase in a Gaucher Disease Mouse Model," PLoS One, 2010, 5(5):e10750, 15 pgs.
Xu, Y-H., et al., "Dependence of reversibility and progression of mouse neuronopathic Gaucher disease on acid β-glucosidase residual activity levels," Mol. Genet. Metab., 2008, 94:190-203, 14 pgs.
Xu, Y-H., et al., "Effect of cellular type on expression of acid β-glucosidase: implications for gene therapy in Gaucher disease," Gene Ther, 1995, 2(9):647-654, 5 pgs.
Xu, Y-H., et al., "Multiple pathogenic proteins implicated in neuronopathic Gaucher disease mice," Hum. Mol. Genet., 2014, 23(15):3943-3957, 15 pgs.
Yednock, T.A., et al., "Prevention of experimental autoimmune encephalomyelitis by antibodies against α4β1 integrin," Nature, 1992, 356:63-66, 4 pgs.
Yu, T., et al., "Ryanodine receptor antagonists adapt NPC1 proteostasis to ameliorate lipid storage in Niemann-Pick type C disease fibroblasts," Hum. Mol. Genet., 2012, 21(14):3205-3214, 10 pgs.
Yusuf-Makagiansar, H., et al., "Inhibition of LFA-1/1CAM-1 and VLA-4NCAM-1 as a Therapeutic Approach to Inflammation and Autoimmune Diseases," Med Res Rev, 2002, 22(2):146-167, 22 pgs.
Zennou, V., et al., "HIV-1 Genome Nuclear Import Is Mediated by a Central DNA Flap," Cell, 2000 101(2):173-185, 13 pgs.
Zhang, X., et al., "Genome-wide analysis of cAMP-response element binding protein occupancy, phosphorylation, and target gene activation in human tissues," Proc. Natl. Acad. Sci. U S A., 2005, 102(12):4459-4464, 6 pgs.
Zufferey, R., et al., "Woodchuck Hepatitis Virus Posttranscriptional Regulatory Element Enhances Expression of Transgenes Delivered by Retroviral Vectors," J Virol, 1999, 73(4):2886-2892, 7 pgs.
Zunke, F., et al., "Characterization of the complex formed by β-glucocerebrosidase and the lysosomal integral membrane protein type-2," PNAS USA, 2016, 113(14):3791-3796, 6 pgs.

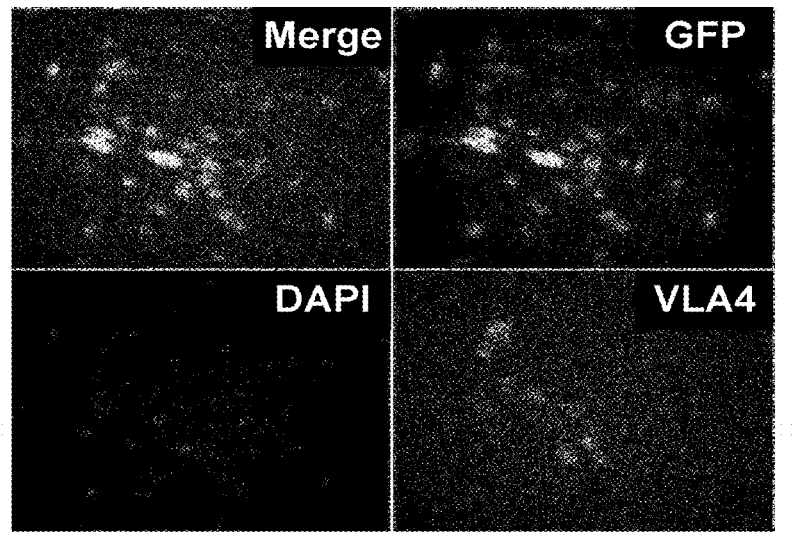
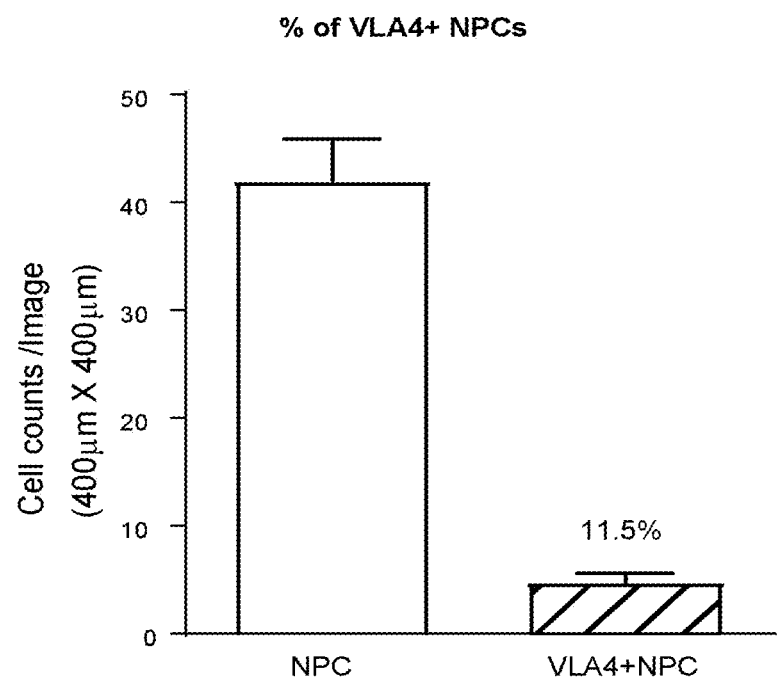
FIG. 1A

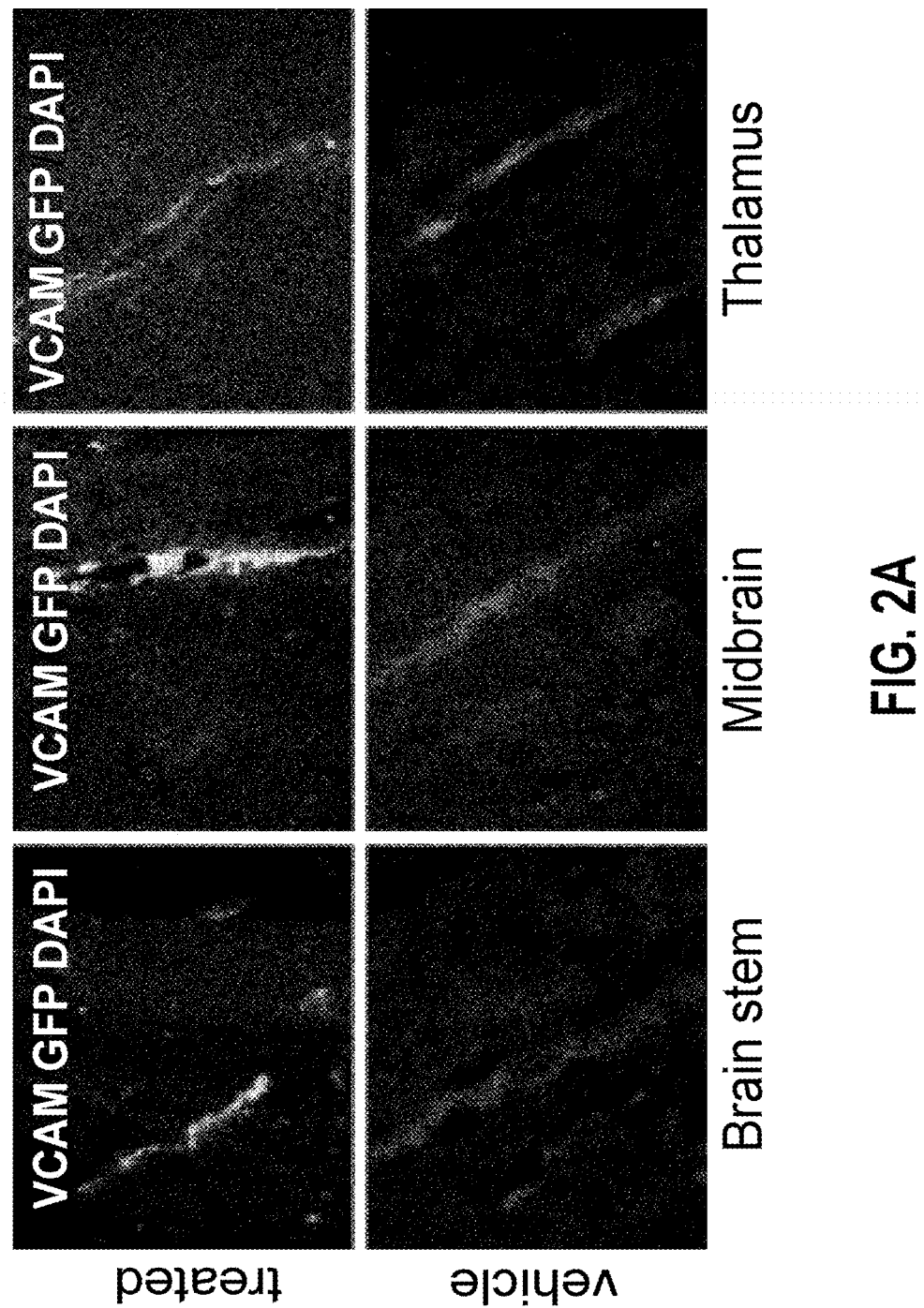

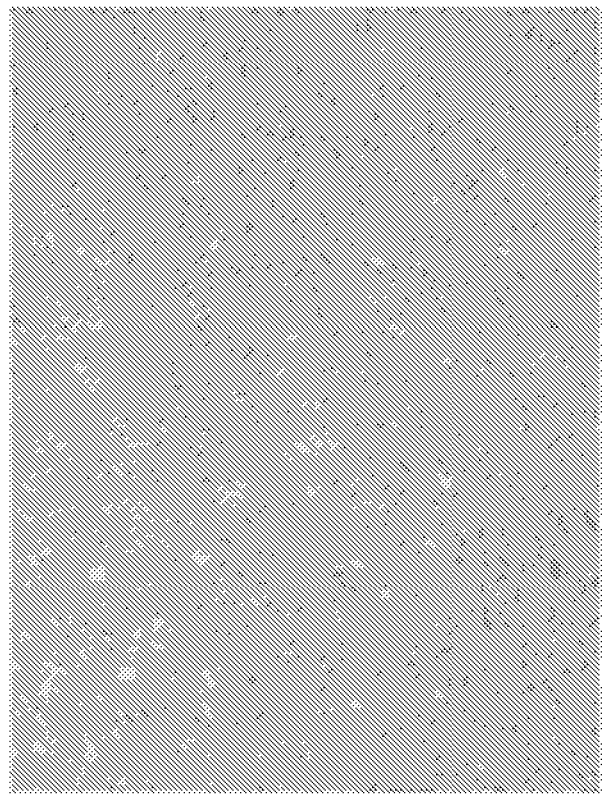
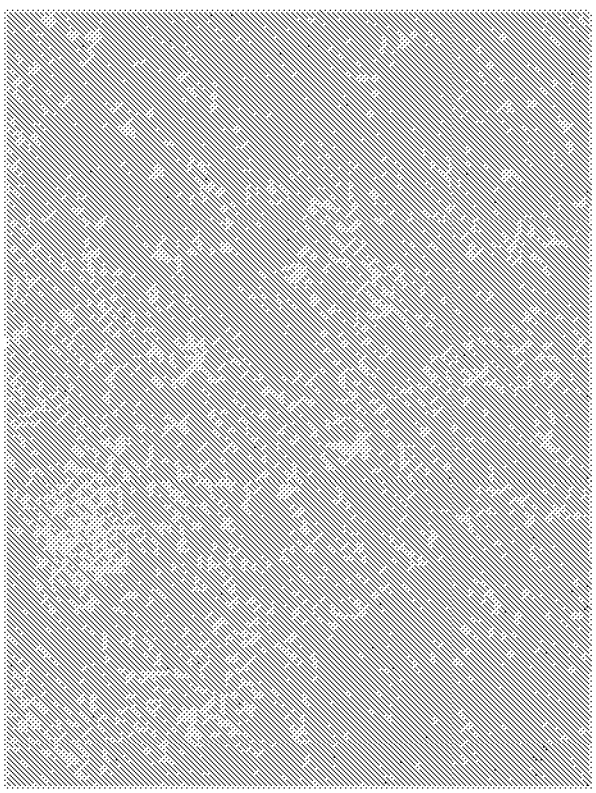
FIG 9B

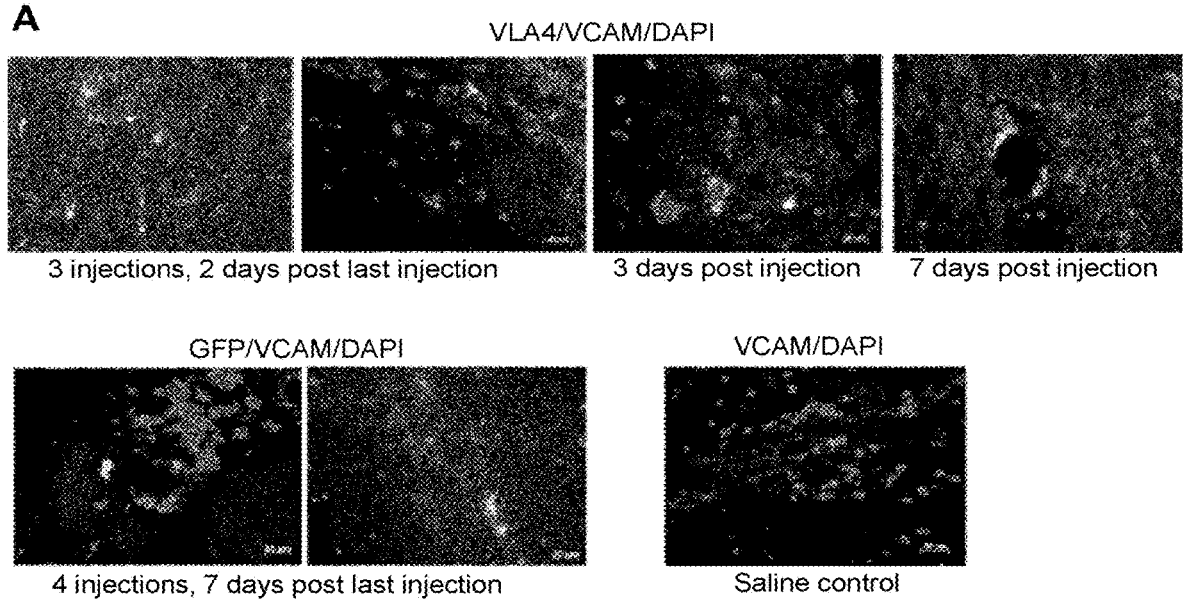
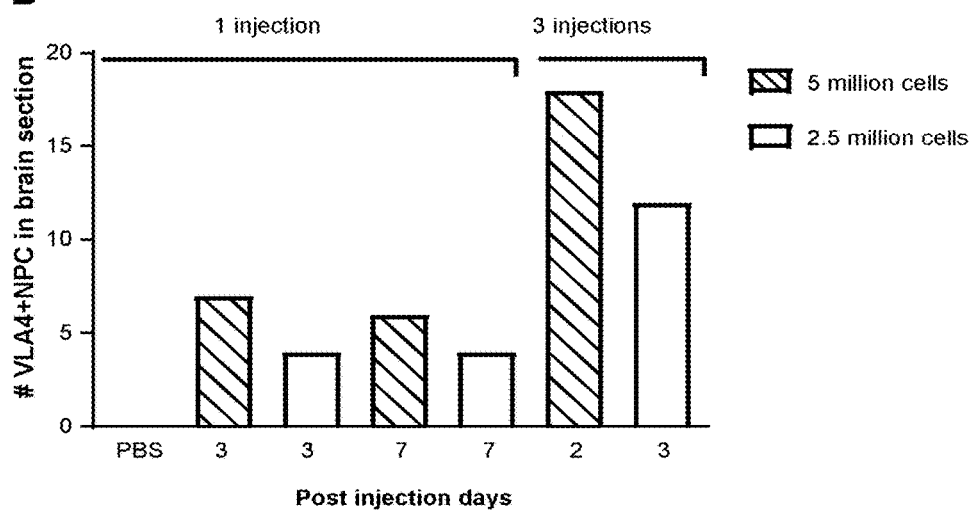
FIG. 13

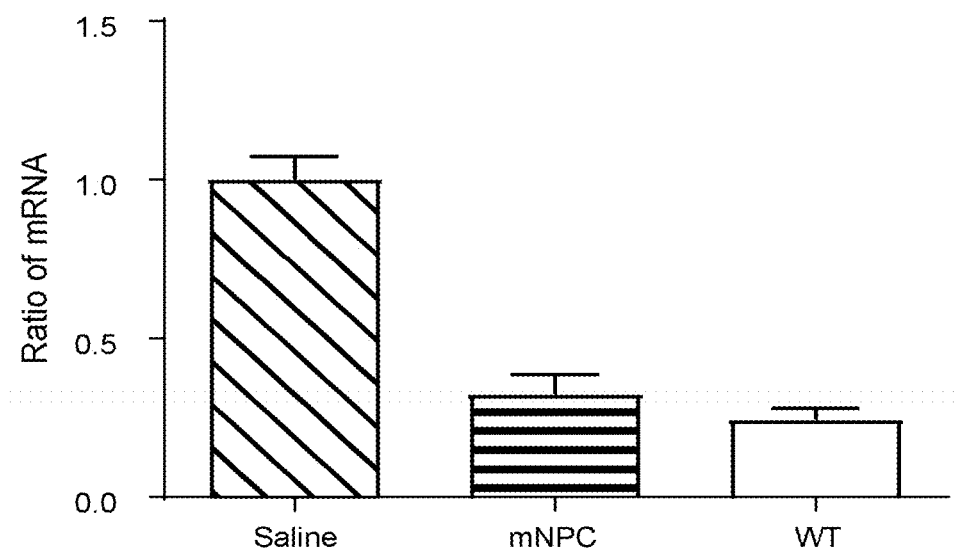
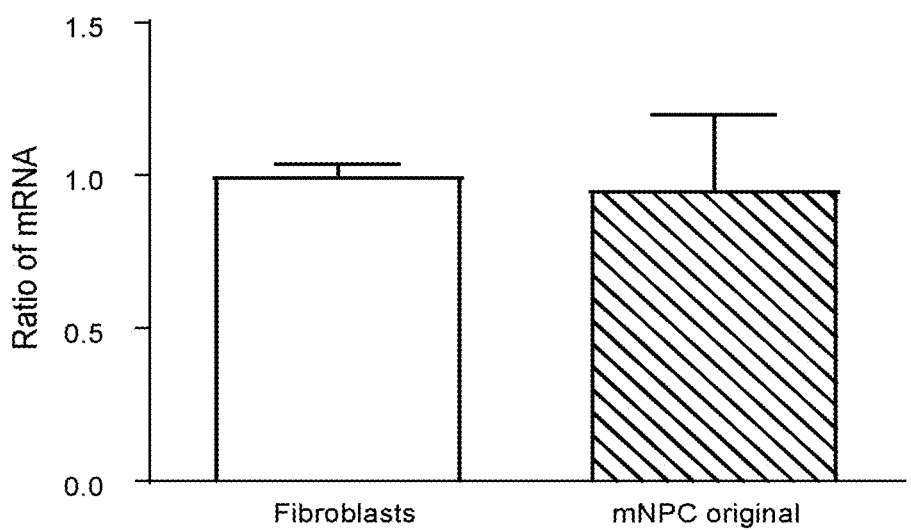
FIG. 16D

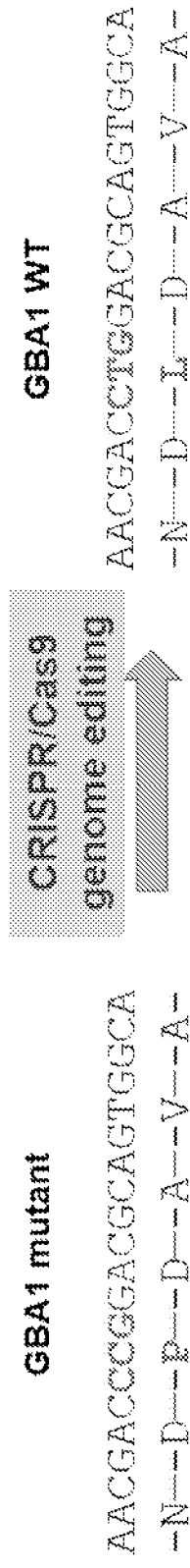
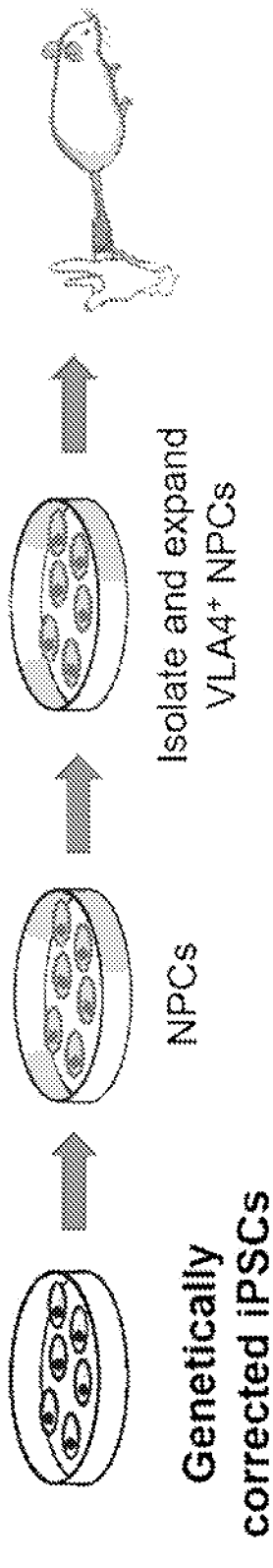
FIG 18

Cell Line: iPSC47_36, hGBAP444 correction → L444 CCG back to CTG gRNA targeting site

WT:  TGCCAGTCAGAAGAACGACCTGGACGCAGTGGCACT (SEQ ID NO: 33)

KI:  TGCCAGTCAGAAGAACGAtCtGAtGCcGTGGCACT (SEQ ID NO: 34)

Cut with BtgI: CCRYGG (SEQ ID NO: 35)

Patient's Strand:   AAG AAC GAC CTG GAC GCA GTG GCA CTG ATG (SEQ ID NO: 36)

Corrected Strand:   AAG AAC GAt GCc GTG GCA CTG ATG (SEQ ID NO: 37)

Genotyping primers used: (pseudogene not amplified) 651bp

VS4247: gtgcgtaactttgtcgacagtcc (SEQ ID NO: 38) (also sequencing primer)

VS4249: CTGAGAGTGTGATCCTGCCAAG (SEQ ID NO: 39)

ssODN design t*c*t*tcagcccacttcccagacctcaccattgccctcaccggtttagcacgaccacaacagagagccatcgggatgcatcagtgccacGgcAtccAgAtcgttctctgactggcaaccagc*c*c*c (SEQ ID NO: 40)
- silent mutations in upper case
- Phosphorothioate modified bases (*)

FIG. 19

Clone 9: Homozygous KI of intended BP mutation, but not all silent mutations, compare sequences below. These indicate that both alleles are present, unlike the previous clone that one allele is missing.

Allele 1: AAG AAC GAt CtG GAt GCc GTG GCA CTG ATG (SEQ ID NO: 41)
Allele 2: AAG AAC GAC CtG GAt GCc GTG GCA CTG ATG (SEQ ID NO: 42)

FIG 21 iPSC Clones:
Clone 9: P444 is corrected → L444 (WT). It has only one functional allele because the other L444 is on the mutant allele
Clone 16: P444 is not corrected → P444/L444-MT, looks like not useful
Clone 27: mixed clones, may have a L444/L444-MT clone
Clone 40: mutations on both alleles, uncorrected clone
Clone 44: P444 is corrected + 10 bp deletion on the mutant (P415R) allele → L444/del-P415R
Clones 5,6,24,29 are unmodified. P444 is not corrected Control iPSC: H1 is from a healthy individual

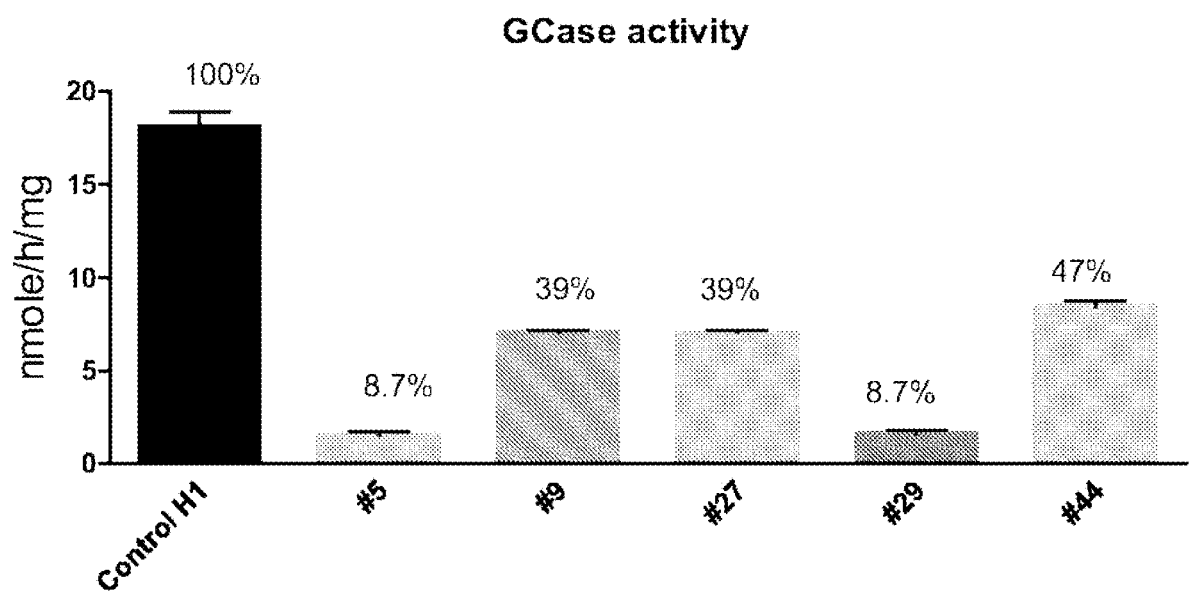

1. For PLVX-EF1a-IRES-mCherry (8904bp)

```
         5'...T^CTAGA...3'
Xba I:   3'...AGATC_T...5'
```

Primer-PLVX-GBA1-F: 5'- GAGACTAGT TCTAGA GCCACC ATGGAGTTTTCAAGTCCTTC - 3'
(SEQ ID NO: 43)
      SpeI   XbaI    Kozac    GBA1

Primer-PLVX-GBA1-R: 5'- CGCGGCCGC TCTAGA TCACTGGCGACGCCACAGGTA - 3'
(SEQ ID NO: 44)
                    XbaI    GBA1

2. For FUGW(9941 bp) (EGFP)

5'...A̋CCGGT...3'
AgeI: 3'...TGGCC̣A...5'

Primer-FUGW-GBA1-F: 5'- <u>TCCCCGGGT ACCGGT</u> GCCACC ATGGAGTTTTCAAGTCCTTC - 3'
  (SEQ ID NO: 45)
   SpeI    AgeI    Kozac    GBA1

Primer-FUGW-GBA1-R: 5'- <u>ATGGTGGCG ACCGGT</u> TCACTGGCGACGCCACAGGTA - 3'
  (SEQ ID NO: 46)
       AgeI      GBA1

COMPOSITIONS AND METHODS FOR TREATMENT OF GCASE RELATED DISEASE STATES

CROSS-REFERENCE TO RELATED APPLICATIONS

This application is a continuation of U.S. patent application Ser. No. 16/860,319, entitled "Compositions and Methods for Treatment of GCase Related Disease States" filed on Apr. 28, 2020 and issued as U.S. Pat. No. 11,260,106 on Mar. 1, 2022, which is a divisional of U.S. patent application Ser. No. 15/896,423, entitled "Compositions and Methods for Treatment of GCase Related Disease States," filed on Feb. 14, 2018 and issued as U.S. Pat. No. 10,675,328 on Jun. 9, 2020, which claims priority to and benefit of 62/458,628, filed on Feb. 14, 2017. The contents of which are incorporated herein in their entirety for all purposes.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 17680375_ST25.txt, the date of creation of the ASCII text file is Jul. 29, 2022, and the size of the ASCII text file is 9.14 KB (9,368 bytes).

BACKGROUND

Lysosomal storage diseases such as Globoid cell leukodystrophy, GM2 gangliosidosis, Niemann-Pick C, Mucopolysaccharidoses, Fabry, Tay-Sachs, Sandhoff and Hypercholesterolemia and Gaucher Disease are associated with increased cellular immune inflammation and have limited treatment options. Gaucher disease ("GD"), in particular, is a rare disease with an incidence of about 1 in 60,000 in the general population and 1 in 850 among Ashkenazi Jewish populations. Worldwide there are about 121,522 Gaucher disease patients and here in the US, approximately 5000 Americans are suffering from this disease.

GD results from mutations in the glucocerebrosidase gene GBA1 causing functional disruption of the encoded lysosomal enzyme, acid beta-glucosidase, leading to excess accumulation of glucosylceramide (GC) mainly in macrophages (Mϕs) and elevated plasma level of cytokines and chemokines in human GD patients. Acid beta-glucosidase is crucial for the degradation of GC into glucose and ceramide. The excess accumulation of GC in innate and adaptive immune cells within several visceral organs, bone and brain sparks a pro-inflammatory environment resulting in tissue recruitment of several inflammatory immune cells. This pro-inflammatory environment causes tissue damage and promotes clinical GC manifestation.

Improved treatments are needed. Currently, the cost to treat an individual with enzyme replacement therapy is significant, in the range of approximately $100,000 to $300,000 per year. Similarly, substrate reduction therapy (e.g., eligustat and miglustat) is equally expensive. While alternative treatments have potential, such as gene therapy, substrate reduction therapy, and alternative enzyme replacement products, such treatments have been hampered by limitations in the understanding of disease pathogenesis and toxicity concerns due to the blood brain barrier and procedural risks (particularly with respect to gene therapy methods).

Thus, there is an urgent need for alternative therapeutic options for the above-noted disease states and disease states of similar etiology. Further alternative treatments are needed for the management of disease complications in GD and other lysosomal storage diseases associated with increased cellular immune inflammation. The instant disclosure satisfies one or more of these needs in the art.

BRIEF SUMMARY

Disclosed are compositions and methods of treating a neurodegenerative disease in an individual. The methods disclose administration of an Integrin α4β1, Very Late Antigen-4 positive neural precursor cell ("VLA4+NPC") transfected with a lentivirus overexpressing wild type GCase to an individual having a neurodegenerative disorder. The neurodegenerative disease may include lipid storage diseases, for example Gaucher disease, Parkinson's disease (PD), Dementia with Lewy bodies.

BRIEF DESCRIPTION OF THE DRAWINGS

This application file contains at least one drawing executed in color. Copies of this patent or patent application publication with color drawing(s) will be provided by the Office upon request and payment of the necessary fee. Those of skill in the art will understand that the drawings, described below, are for illustrative purposes only. The drawings are not intended to limit the scope of the present teachings in any way.

FIG. 1A-1E. Enrichment and characterization of VLA4+ mNPCs. (FIG. 1A) WT GFP+mouse (m) iPSC-derived NPCs had 11% VLA4+cells stained with anti-mouse VLA4 antibody. All mouse NPCs are GFP positive. DAPI stains cell nuclei. (FIG. 1B) FACS using anti-VLA4 antibody enriched VLA4+GFP+mNPCs. (FIG. 1C) The FACS sorted cells were stained by anti-VLA4 antibody. Scale bar=xx nm. (FIG. 1D) VLA4+m NPCs are validated by neural stem cell markers, anti-Nestin and anti-SOX2 antibodies. (FIG. 1E) VLA4+mNPCs were differentiated into neurons, oligodendrocytes, and astrocytes. DAPI stains cell nuclei. Scale bar=xx nm.

FIG. 2A-2F. The GFP+VLA4+mNPCs engrafted into the brains of 4L;C* mice by intravenous administration. GFP+VLA4+mNPCs ($1\times10^6$ cells) were transplanted by intravenous injection, twice per week, into 4L;C* mice starting at 30 days of age. (FIG. 2A) Donor GFP+mNPCs were detected in the VCAM1+ endothelia cell layer in the brain, particularly in the brainstem, midbrain and thalamus. Representative images of some donor GFP+ cells acquiring (FIG. 2B) glial phenotype that are positive for GFAP, (FIG. 2C) neuronal phenotype that are positive for NeuN), and (FIG. 2D) oligodendrocyte phenotype that are positive for O4. (FIG. 2E) qRT-PCR data showed number of GFP positive cells in midbrain. (FIG. 2F) The distribution of GFP positive cells in the mouse brain with 2× IV/week injections).

(FIG. 3A) mNPCs transplanted 4L;C* mice had significantly ($p<0.05$) prolonged survival compared with Vehicle (saline) injected 4L;C* mice with treatment regime, one IV/week, two IVs/week or three IVs/week. (FIG. 3B) The hindpaw clasping test, a marker of neurodegenerative disease, showed significantly delayed clasping in the mNPC transplanted 4L;C* mice (two IVs/week and three IVs/week) compared to saline-4L;C* control. (FIG. 3C) Transplantation of mNPCs significantly improved sensorimotor function in 4L;C* mice at 50 days of age by gait analysis for the mice with treatment of one IV/week, two IVs/week and three IVs/week. Student's t-test.

(FIG. 6A-FIG. 6D) GCase activity. GCase activity in midbrain of mNPC treated 4L;C* mice was significantly increased by 35% at 50 days of age (p=0.002) (FIG. 6A) and modestly increased by 16% at end-stage (FIG. 6B) compared to that in vehicle-4L;C* mice. In the brainstem, mNPC treatment enhanced the GCase activity by 28% (FIG. 6C) at the 50 days of age and by 16% end-stages (FIG. 6D) compared to that in vehicle-4L;C* mice. The data represent the mean±S.E. (n=3 mice), assayed in triplicate. Student's t-test. ***, p<0.001. (FIG. 6E and FIG. 6F) Substrate levels. GC levels (FIG. 6E) and GS levels (FIG. 6F) in the midbrain of mNPC transplanted 4L;C* mice at 50 days of age showed 34% and 23% reduction compared to that in vehicle-4L;C* mice. The data represent the mean±S.E. and analyzed by Student's t-test. *, p<0.05 (n=3 mice). The GC and GS levels were normalized by mg wet tissues.

FIG. 8D depicts mRNA expression of LIF in brain and in cells.

FIG. 9A-9B. Isolation of VLA4+ human and mouse iPSC-derived NPCs and mouse C17.2 NPCs. A portion of human and mouse iPSC-derived NPCs and mouse C17.2 NPCs express VLA4. (FIG. 9A) Fluorescence-activated cell sorting of VLA4+NPCs by flow cytometry (FACS). (FIG. 9B) Human and mouse VLA4+NPCs maintain NPC morphology.

FIG. 13. Engraftment of VLA4+C17.2 NPC in GD mouse brains. (A) GFP labeled VLA4+C17.2 cells engrafted into GD mouse brains by IV administration. The mouse brains were collected 2 days, 3 days or 7 days post last injection. The VLA4+ cells detected by anti-VLA4 or anti-GFP antibodies were detected in mice brains received IV delivered VLA4+C17.2 NPCs. None of VLA4+ cells were detected in PBS injected mice brain. (B) The GFP positive C17.2 NPCs were counted in sagittal brain sections of treated mouse brain, 10 images per mouse.

FIG. 16A-16F. Neurotrophic factor expression. The mRNA expression of neurotrophic factors in mice brains and cells were determined by qRT-PCR. Compared to vehicle-4L;C* brain, CNTF (FIG. 16A) and TNFα (FIG. 16B) expressed in NPC showed decreased expression in treated 4L:C* brain; IGF1 (FIG. 16C) and FGF2 (FIG. 16D) did not show superior expression in NPC over fibroblasts, and their levels were decreased in treated 4L;C* brain; JAG1 (FIG. 16E) and TGFβ2 (FIG. 16F) did not express in NPC, their levels were increased in treated 4L;C* brain. (Duplicated experiments with triplicated sample/experiment, n=3 mice).

FIG. 18. Approach of genetic correction of GBA1 mutation for cell therapy. The single stranded guide (g) RNAs are designed to target the mutation, L444P (GBA1 mutation at nt14446, T>C) on iPSCs. The corrected iPSC will be derived to neural precursor cells (NPC) for cell transplantation.

FIG. 19. gRNA design for genetic correction of GBA1 mutation L444P. Sequences of gRNA targeting the mutation L444P (GBA1 mutation at nt14446, T>C), a phosphorothioate-modified single stranded oligonucleotide (ssODN) donor template and genotyping primers.

FIG. 21. Restored GCase activity in the genetically-corrected iPSC clones. Corrected GD-iPSC clones are assayed for GBA1 encoding enzyme acid β-glucosidase (GCase) activity to confirm restoring GCase in corrected clones. Corrected clones (#9, #27, #44) recovered GCase activity at ~40-47% of normal level, compared to the control H1 clone with normal GBA1 gene, which reached to the heterozygous GBA1 levels.

DETAILED DESCRIPTION

Definitions

Figure 1B:
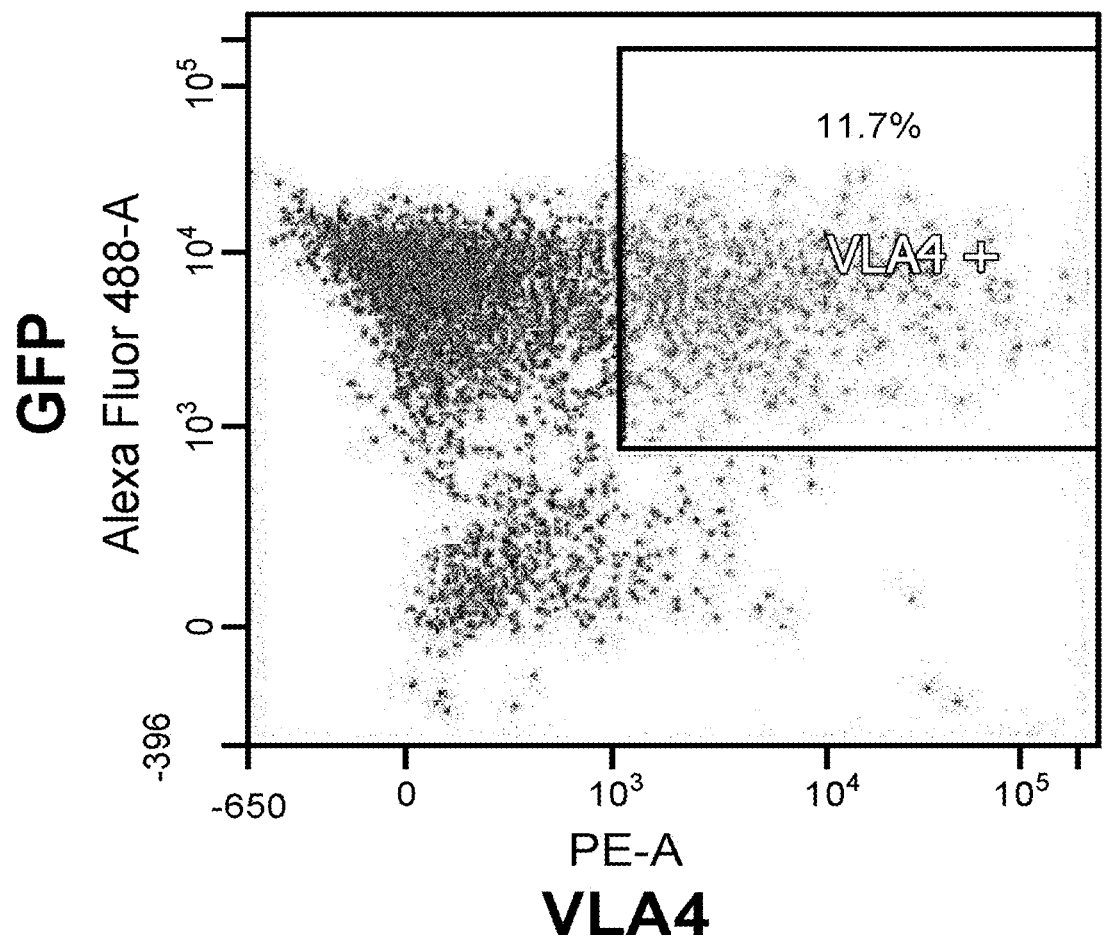
Figure 1C:
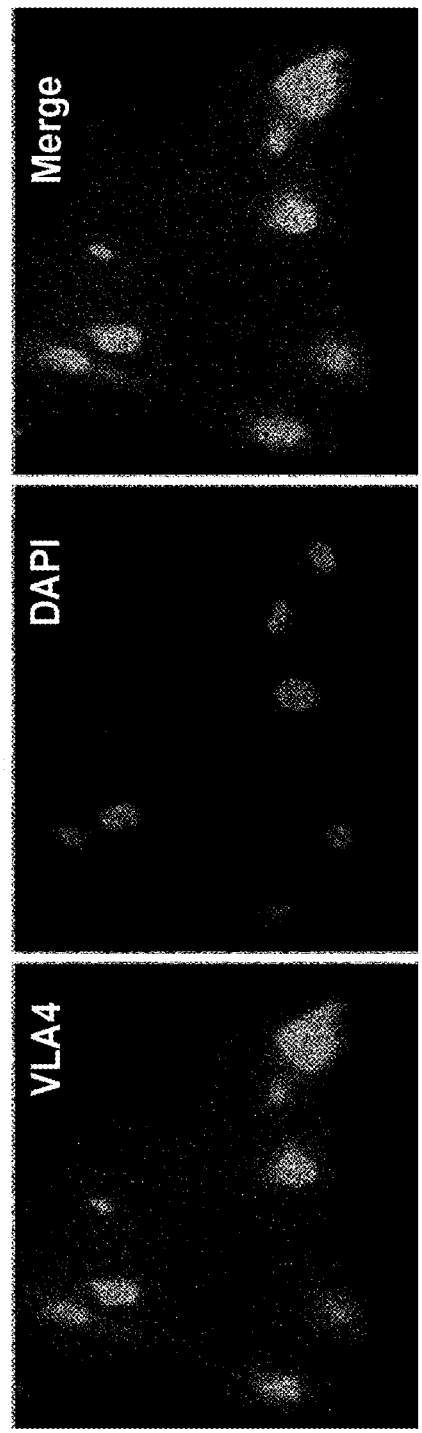
Figure 1D:
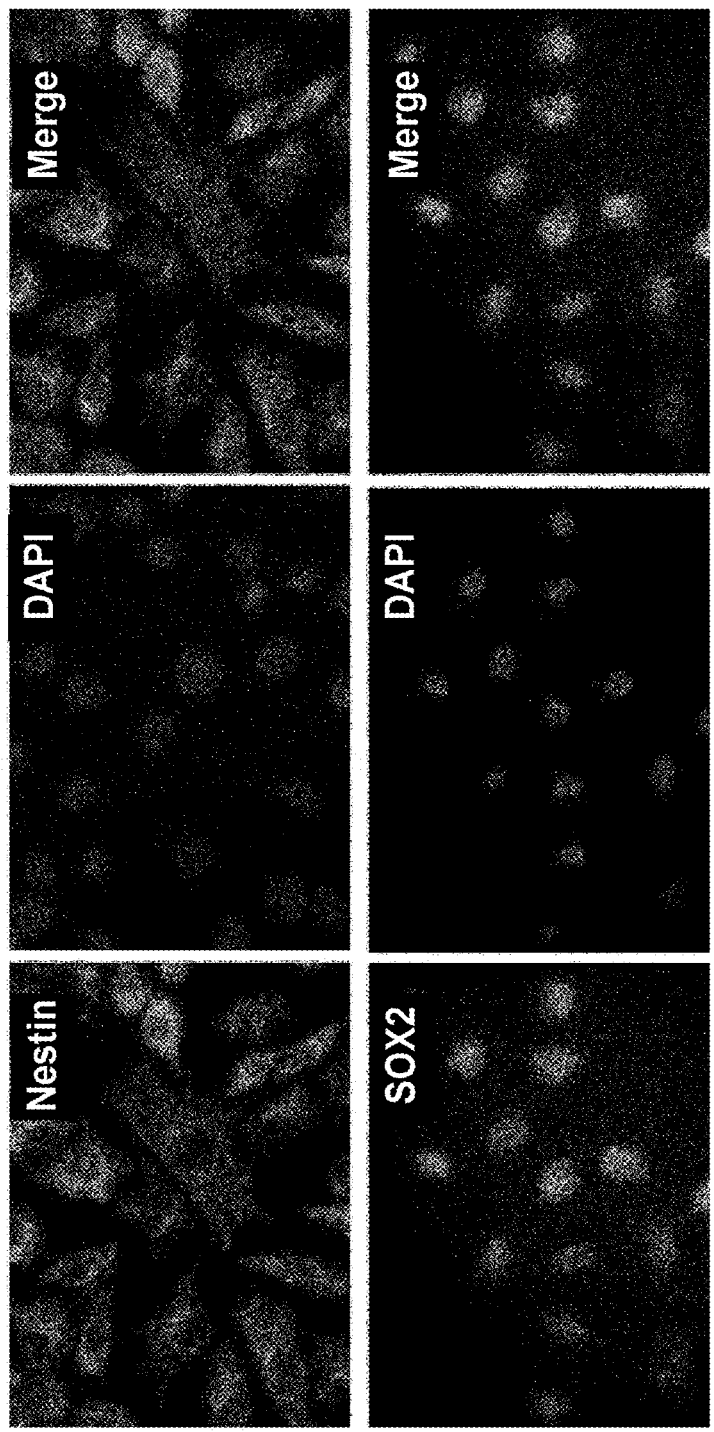
Figure 1E:
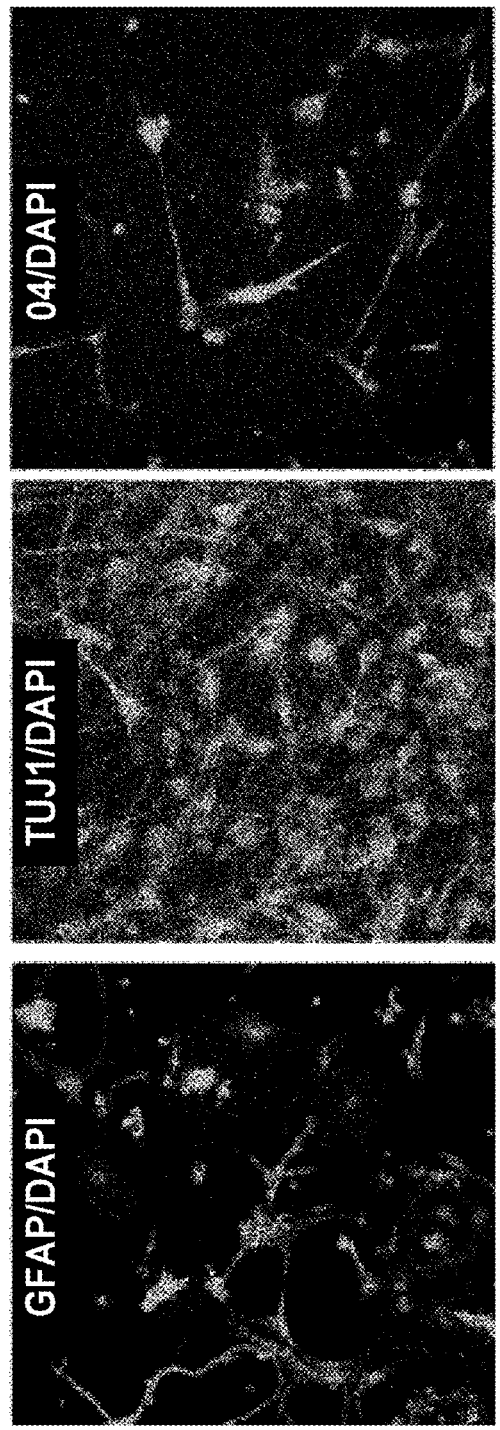
Figure 2B:
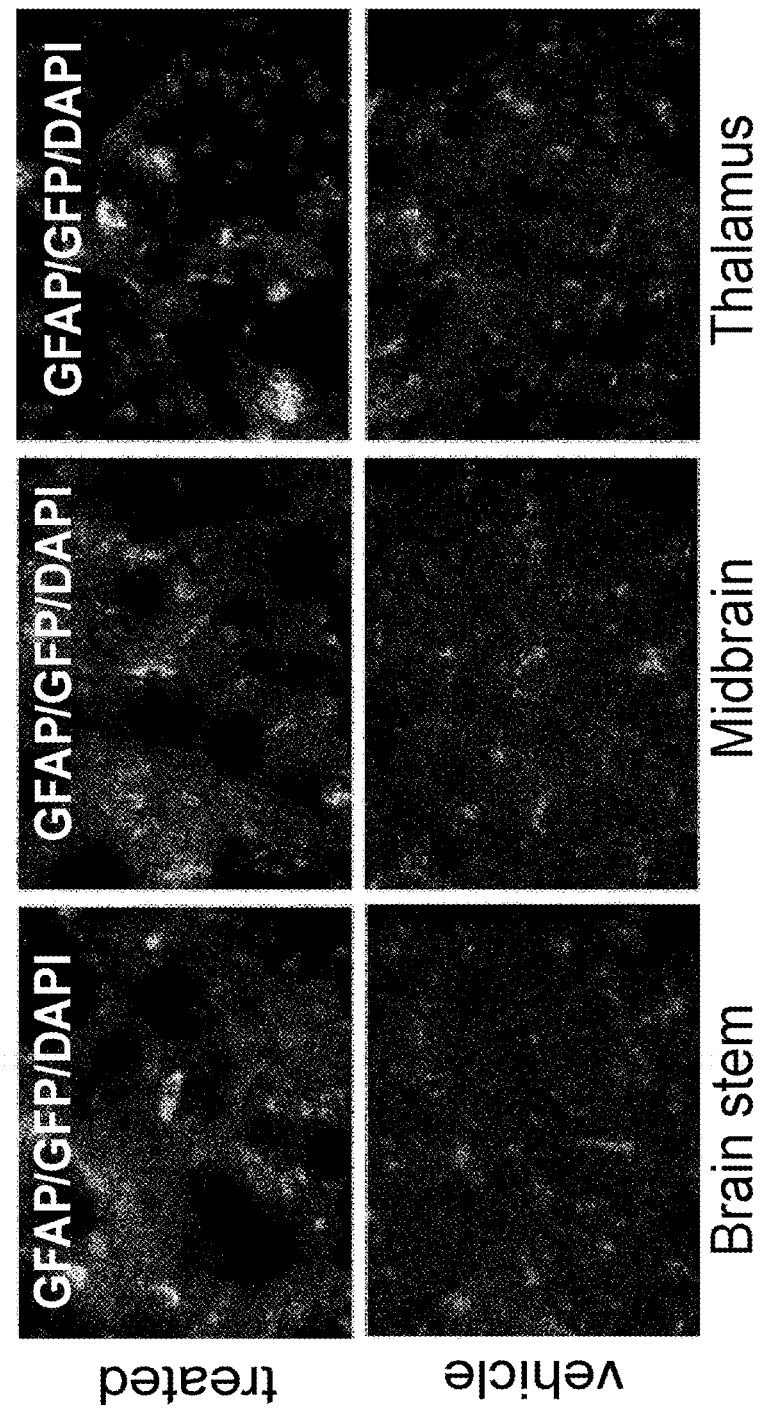
Figure 2C:
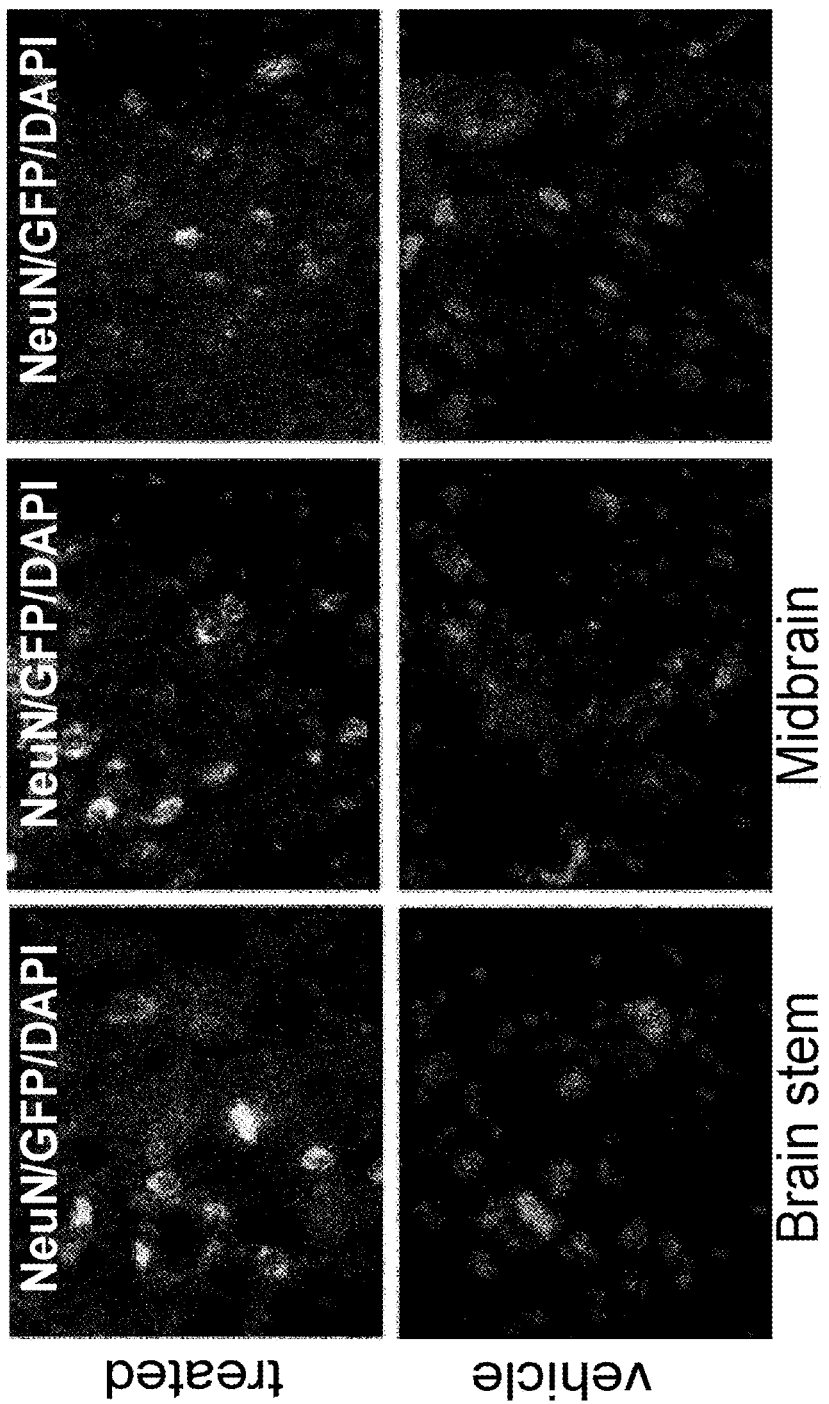
Figure 2D:
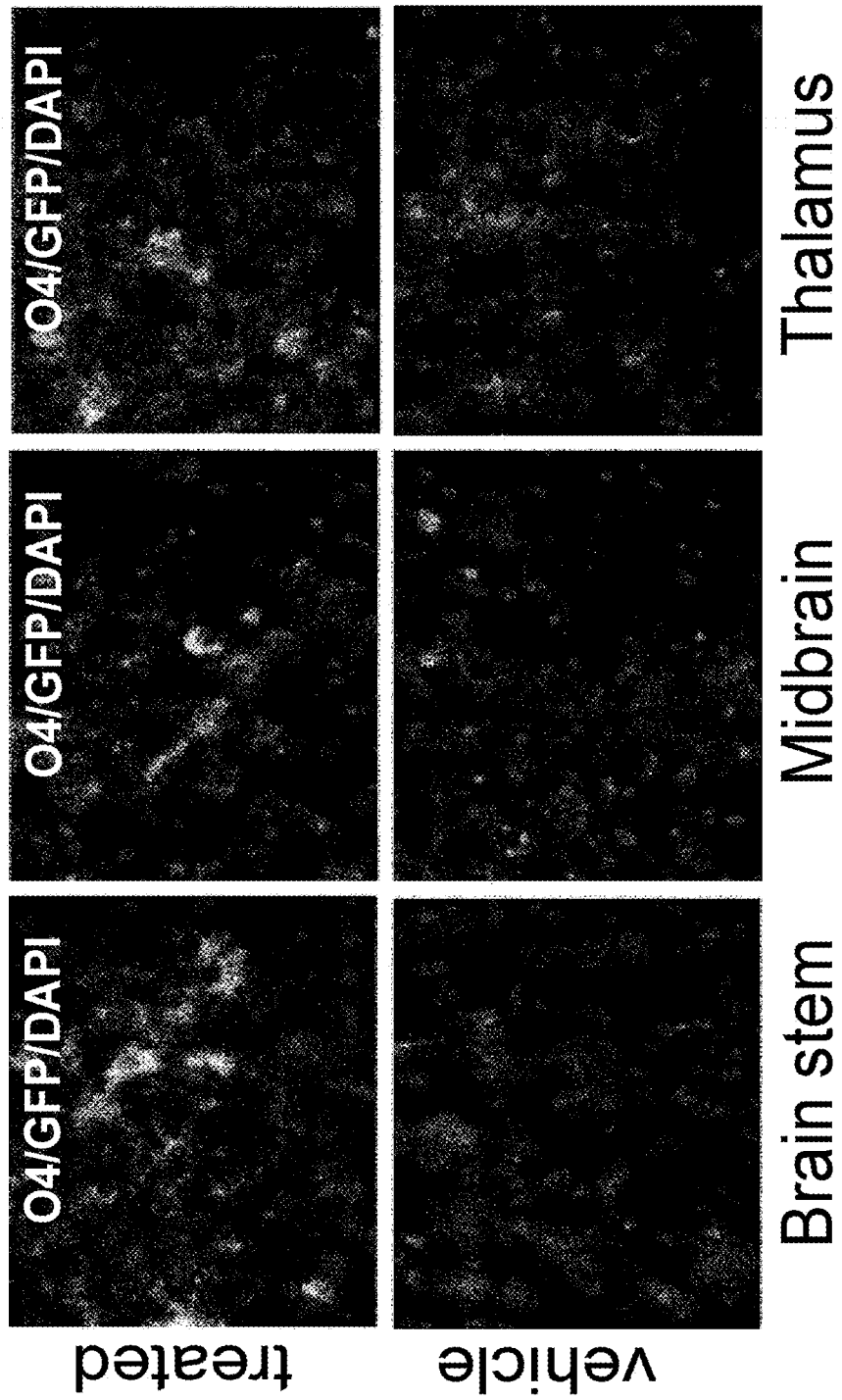
Figure 2E:
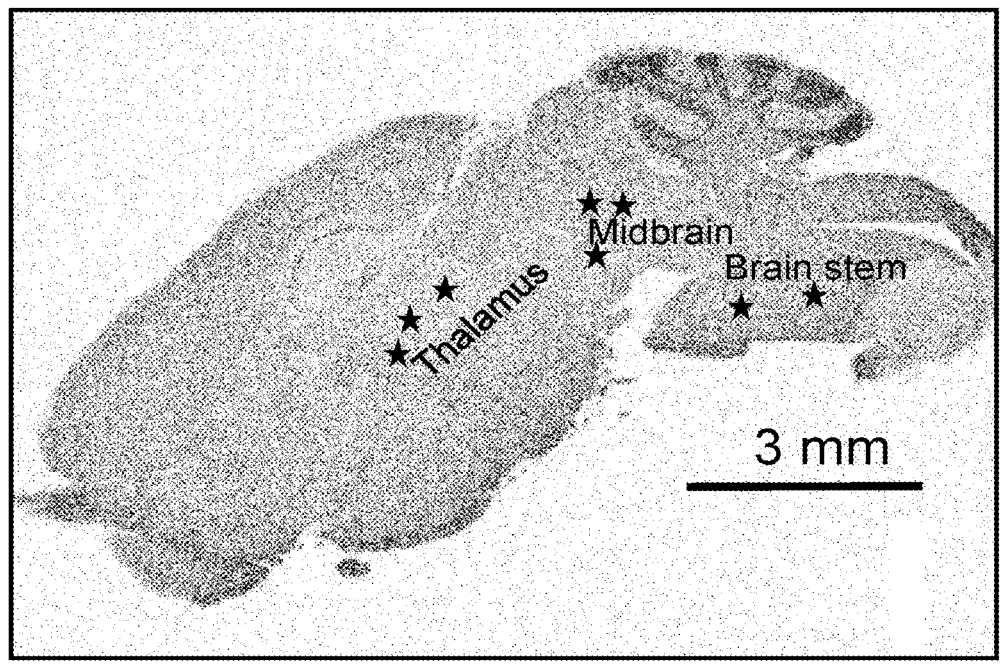
Figure 2F:
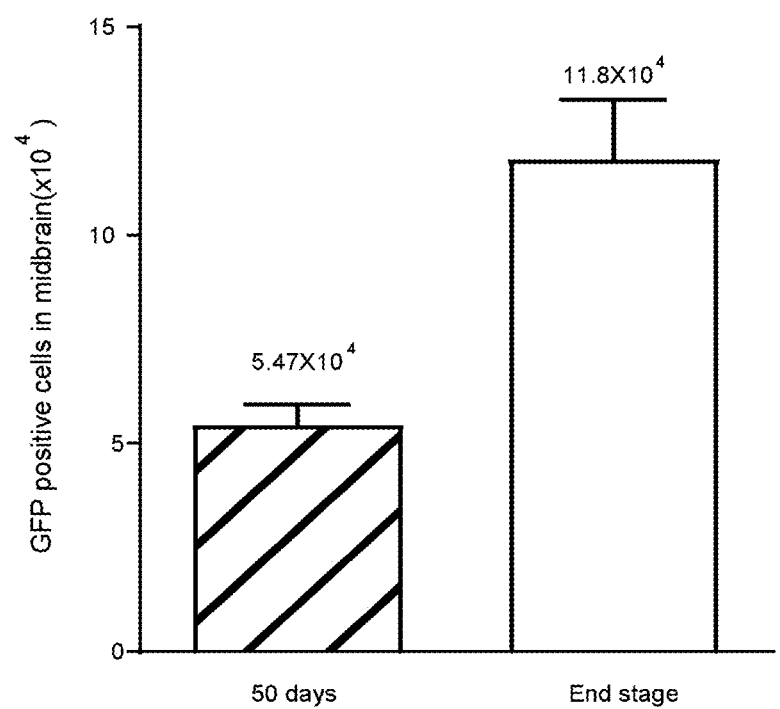

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

There is no effective treatment available for neuronopathic Gaucher disease characterized by progressive neurodegeneration phenotype. A therapy of non-invasive transplantation of neural precursor cells for disease states such as neuronopathic Gaucher disease is disclosed.

Gaucher disease is caused by GBA1 mutations leading to functional deficiency of lysosomal acid-β-glucosidase. GBA1 mutations that cause Gaucher disease have been identified as the most common genetic risk factor for Parkinson's disease. Applicant has developed a non-invasive, autologous induced pluripotent stem cell (iPSC)-based cell and gene therapy for treatment of diseases such as neuronopathic Gaucher disease and Parkinson's disease. A subclass of neural stem and precursor cells (NPCs), including iPSCs-derived NPCs, express VLA4 (Integrin α4β1, Very Late Antigen-4) which allows NPCs to cross the blood-brain-barrier.

Applicant has found that the GBA1 mutation in human Gaucher disease iPSCs can be genetically corrected and iPSC-derived NPCs having a VLA4+ population can be established. Applicant has found that the VLA4+NPCs maintained multipotency and differentiated into neurons, astrocytes, and oligodendrocytes. The non-invasive delivery of iPSC derived VLA4+NPCs benefit individuals having Parkinson's disease by increasing GBA1 gene product, promoting neuroprotection and direct cell replacement through differentiation to functional cell types in the central nervous system.

A subclass of neural stem and precursor cells (NPCs), including induced pluripotent stem cell (iPSC)-derived NPCs, express VLA4 (Integrin alpha4beta1, Very Late Antigen-4) allows systemically delivered NPCs to cross the blood-brain-barrier via interaction with endothelial VCAM 1 (vascular cell adhesion molecule). Applicant has established multipotent human and mouse iPSC-derived VLA4+ NPCs. Mouse iPSC-derived VLA4+NPCs expressing GFP engrafted in neuronopathic Gaucher disease (4L;C*) mouse brain following intravenous injection. GFP positive cells were distributed in brain stem, midbrain, and thalamus in the transplanted 4L;C* brains and were differentiated into neurons, astrocytes and oligodendrocytes. The NPC transplanted 4L;C* mice showed improved sensorimotor function by gait analysis and delayed neurodegenerative disease progression by the hindlimb clasping test. NPC transplantation significantly prolonged life span of 4L;C* mice. Histological analysis of brain sections by Fluoro-Jade C staining showed significantly reduced neurodegeneration in the brain stem, midbrain, and thalamus of transplanted mice. CNS inflammation, detected by anti-CD68 and anti-GFAP antibodies, was significantly decreased in the brain and spinal cord of transplanted mice. The oxygen consumption rate of NPC treated brain mitochondria was significantly improved compared to vehicle-mice. These results demonstrated the potential efficacy of non-invasive delivery of iPSC-derived NPCs to improve neuronopathic phenotype in the mouse model of neuronopathic Gaucher disease. Applicant has thus established the feasibility of non-invasive, autologous cell therapies using iPSC-derived precursor cells to achieve personalized medicine for neuronopathic Gaucher disease and other neurodegenerative diseases.

In one aspect, a method of treating a neurodegenerative disease in an individual in need thereof is disclosed. The method may, in some aspects, comprise the step of administering to the individual an Integrin α4β1, Very Late Antigen-4 positive neural precursor cell ("VLA4+NPC") The VLA4+NPC may be transfected with a lentivirus overexpressing wild type GCase. The neurodegenerative disease may be selected from Gaucher disease, Parkinson's disease (PD), or Dementia with Lewy bodies. In one aspect, the neurodegenerative disease may be one which is characterized by reduced GCase activity, accumulation of substrates (GC), and/or alpha synuclein aggregation. In one aspect, the neurodegenerative disease may be one which is caused or exacerbated by a GBA1 mutation. In one aspect, the Gaucher disease may be type II nGD. In one aspect, the Gaucher disease may be type III nGD.

In one aspect, the NPC may be derived from an iPSC. The iPSC may be derived from a human fibroblast. Human iPSCs as described herein were established in Pluripotent Stem Cell Core at CCHMC from health individual or GD patients' fibroblasts, using methods known in the art. An exemplary protocol and study were published in Sun, Y., et al. (2015) PLoS One 10(3): e0118771. Mouse iPSCs may be derived from wild type GFP+ mouse fibroblasts.

In one aspect, the VLA4+NPC may be administered to said individual via intravenous administration. One of ordinary skill in the art will readily appreciate suitable carriers for IV administration, such as, for example, sterile solutions commonly used in the art.

In one aspect, the lentivirus may comprise a promoter capable of driving transgene expression in the central nervous system. For example, the promoter may be selected from a human elongation factor 1 alpha ("EF1α") promoter or an Ubiquitin C promoter (UbC). Other suitable promoters will be readily understood by one of ordinary skill in the art.

In one aspect, the VLA4+NPC may be co-administered with a chaperone molecule. For example, the VLA4+NPC may be co-administered with a chaperone molecule such as Dantrolene, Ambroxol, or a combination thereof. Dantrolene and Ambroxol can access a variety of organs including the CNS to restore mutant GCase activity acting as chaperon-inducer or chaperone. Dantrolene, an antagonist of ryanodine receptors, modulates ER-calcium mobilization to regulate calcium-dependent chaperones for GCase protein folding to enhance its function. Dantrolene has been used to safely to treat malignant hyperthermia. Applicant has shown that Dantrolene is capable of repairing mutant GCase activity in GD mutant fibroblasts and nGD mice providing a therapeutic option for GD. Ambroxol, a commonly used expectorant, has been in pilot studies to evaluate its safety and efficacy in vGD and nGD patients and in a Phase I trial for vGD (ClinicalTrials.gov Identifier: NCT01463215) and may be used with the disclosed methods. Ambroxol binds to GCase in a pH dependent manner, assisting in folding at the neutral pH of the ER and releases from GCase at the acidic pH of the lysosome, and may further be used with the disclosed methods.

In one aspect, the VLA4+NPC may be delivered in an amount sufficient to increase GCase activity in the brain. In one aspect, the VLA4+NPC may be delivered in an amount sufficient to improve one or more parameters selected from neurological pathology, survival, brain inflammation, brain neurodegeneration, GCase activity, GCase substrate level, mitochondrial function, neurotropic factor expression, or combinations thereof.

In one aspect, the VLA4+NPC may be co-administered with an ERT (imiglucerase, velaglucerase alfa, taliglucerase alpha) or SRT (eligustat, miglustat, ibiglustat/Verglustat, or combinations thereof, preferably ibiglustat/Verglustat.

In one aspect, a method of treating a neurodegenerative disease in an individual having one or more mutations in a GCase gene is disclosed. The method may comprise the step of administering to the individual an Integrin α4β1, Very Late Antigen-4 positive neural precursor cell ("VLA4+NPC"), wherein fibroblasts or other somatic cells for generating iPSC and the VLA4+NPC may be harvested from the individual, and wherein the VLA4+NPC may contain one or more corrected GCase genes. In one aspect, the corrected GCase gene may be a CRISPR-corrected GCase gene, using methods known in the art. (See, e.g., Ran F A, Hsu P D, Wright J, Agarwala V, Scott D A, et al. (2013) Genome engineering using the CRISPR-Cas9 system. Nature protocols 8: 2281-2308.) In one aspect, the VLA4+NPC containing one or more CRISPR-corrected GCase genes may be administered intravenously to an individual in need thereof.

In one aspect, one or more CRISPR corrected genes may be achieved by carrying out one or more of the following steps: contacting an iPSC derived from said individual with a guide RNA ("gRNA") specific for a targeted genomic region containing one or more mutations and a CRISPR-associated endonuclease (examples include, but are not limited to, Cas9, S. pyogenes Cas9 (SpCas9), Cpf1, or the like) in an amount and for a duration sufficient to convert said mutation to a wild-type sequence; assessing CRISPR-Cas9 cleavage activity; genotyping edited human iPSC cell clones; functionally screening said edited human iPSC cell clones via an enzyme activity assay; karyotyping for chromosomal analysis of the edited human iPSC cell clones; differentiating said iPSC cells to neural precursor cells (NPCs); deriving a VLA4+NPC enriched population from said NPCs, preferably wherein said step of deriving said VLA4+NPC population is carried out by subjecting the NPCs to a FACS sorting step.

In one aspect, the VLA4+NPC enriched population may comprise at least 50% NPC cells that are VLA4+, or at least 60% NPC cells that are VLA4+, or at least 70% NPC cells that are VLA4+, or at least 80% NPC cells that are VLA4+, or at least 90% NPC cells that are VLA4+, or about 100% NPC cells that are VLA4+. The VLA4+NPC enriched population may be administered to an individual in an amount of at least about $1 \times 10^6$ cells per injection. In one aspect, the VLA4+NPC enriched population may be administered at a concentration of about $1 \times 10^6$ cells/100 ul. In one aspect, the VLA4+NPC enriched population may be administered in a carrier selected from saline or phosphate buffered saline. In one aspect, the VLA4+NPC enriched population may be co-administered with a neurotropic factor in an amount sufficient to increase cell engraftment. In one aspect, the VLA4+NPC population may be administered 1 to 3 times per week. In certain aspects, the NPC cell clearance may be monitored in blood by Flow cytometry using neural stem cell marker (e.g., nestin). In one aspect, the VLA4+NPC may further comprise a detectable tag, for example, GFP, by transduction of lentiviral GFP into NPCs. In certain embodiments, the GFP tag can be used to track the tissue distribution of engrafted NPCs.

In one aspect, the targeted genomic region may be a region wherein a functional mutation is located. For example, there are more than 400 known GBA1 mutations.

(See, e.g., Grabowski G A, Zimran A, Ida H. "Gaucher disease types 1 and 3: Phenotypic characterization of large populations from the ICGG Gaucher Registry". Am J Hematol. 2015 July; 90 Suppl 1:S12-8. doi: 10.1002/ajh.24063. Review) In one aspect, the VLA4+NPC population may be assayed for secretion of wild-type GCase protein prior to administration to an individual in need thereof.

In one aspect, a method of transplanting a cell in the central nervous system of an individual is disclosed. In this aspect, the method may comprise administering a VLA4+ NPC derived from the individual, wherein the administration may be intravenous. The method may be used to treat a neurodegenerative disease such as Gaucher disease, Parkinson's disease (PD), Dementia with Lewy Bodies, or a lysosomal disease with a brain manifestation, including lysosomal diseases with brain diseases, or a lysosomal disease with a brain manifestation, including lysosomal diseases with brain diseases. The neurodegenerative disease may be one characterized by reduced GCase activity and/or alpha synuclein aggregation, for example, neuronopathic Gaucher disease, or a neurodegenerative disease caused by a GBA1 mutation. In certain aspects, the NPC may be derived from an iPSC. As set forth above, the VLA4+NPC may be co-administered with a chaperone molecule as described. The VLA4+NPC may be delivered in an amount sufficient to improve one or more parameters selected from neurological pathology, survival, brain inflammation, brain neurodegeneration, GCase activity, GCase substrate level, mitochondrial function, neurotropic factor expression, or combinations thereof in the treated individual.

In one aspect, a medicament for the treatment of a neurodegenerative disease comprising an Integrin α4β1, Very Late Antigen-4 positive neural precursor cell ("VLA4+ NPC") transfected with a lentivirus overexpressing wild type GCase, as described in any of the embodiments above, is disclosed.

Examples

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. Those of skill in the art should, in light of the present disclosure, appreciate that many changes can be made in the specific embodiments that are disclosed and still obtain a like or similar result without departing from the spirit and scope of the invention.

Applicant has genetically corrected GBA1 mutation in human iPSCs derived from an individual with Gaucher disease (GD). Specifically, CRISPR/Cas9 was used to correct the L444P mutation in an iPSC line harboring compound heterozygous GBA1 mutations (L444P/P415R).

In the following examples, patient iPSCs are from GD neuronopathic variants having GBA1 mutations: L444P/P415R. L444P is second most prevalent GD causing mutation. It is a severe mutation that, in homozygosity or compound heterozygosity with other mutations, leads to neuropathic type GD.

The clone originally selected for correction (iPSC47_32) was one described in Sun, Y., et al. (2015) PLoS One 10(3): e0118771, which describes the generation of GD-specific human iPSCs. Applicant has generated iPSCs from fibroblasts derived from both human GD patients and normal individuals. The iPSCs can differentiate into NPCs using a routine neural aggregation-based protocol. (Sun, Y., et al. (2015) PLoS One 10(3): e0118771). NPCs can be stably passaged in vitro whilst maintaining the expression of nestin and sox2. NPCs possess multipotency when they were cultured with FGF8 and SHH. Resulting cultures contained both GFAP+astrocytes and Tuj1+ neurons, demonstrating multipotency. Neurons possessed prototypical electrophysiological properties when assayed by whole cell patch-clamp. (Sun, Y., et al. (2015) PLoS One 10(3): e0118771).

Figure 3A:
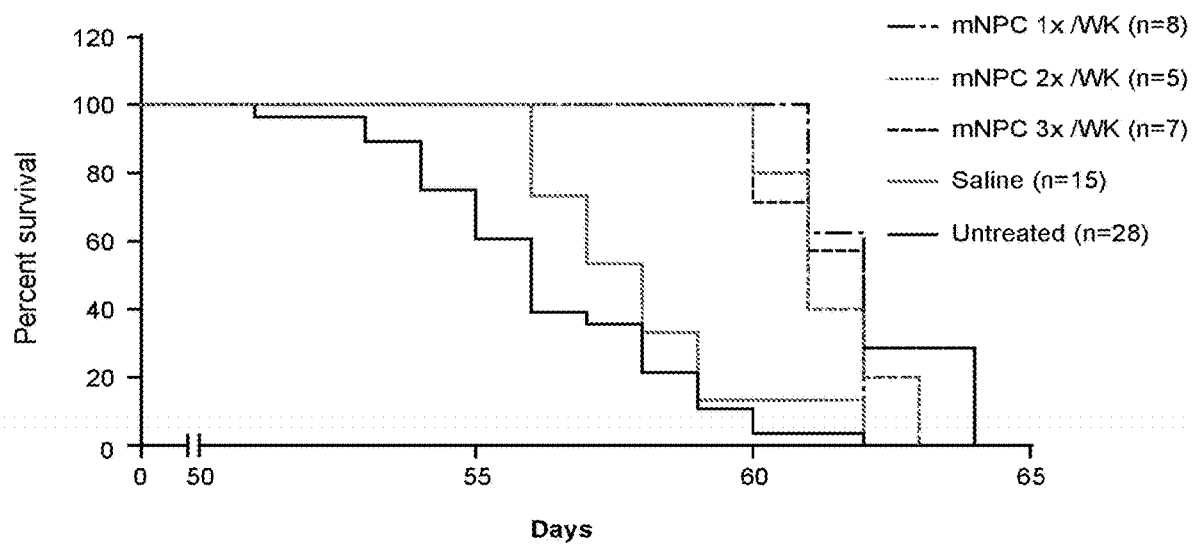
FIG. 3A-3C. Transplantation of GFP+VLA4+mNPCs (mNPCs) into 4L;C* mice prolonged survival and improved sensorimotor function.
Figure 3B:
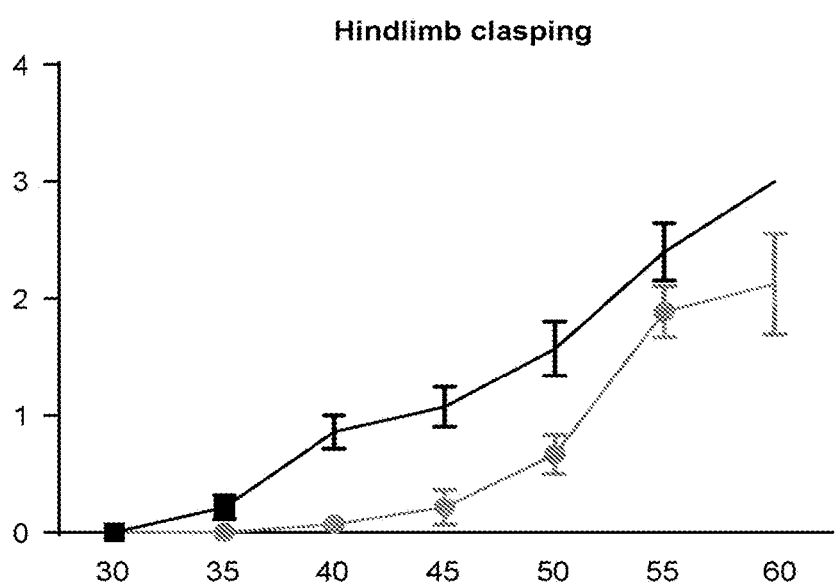
Figure 3C:
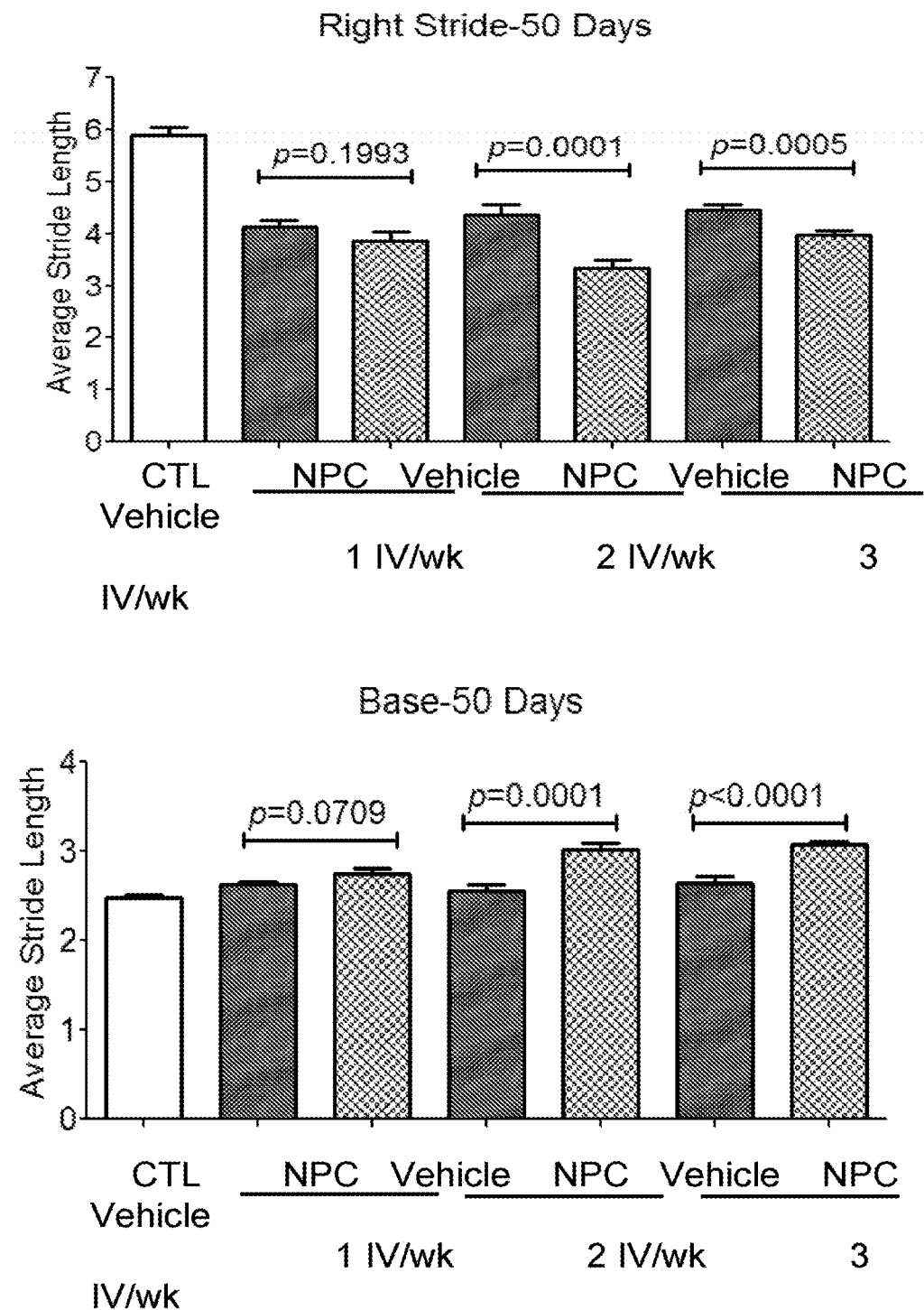
Figure 4A:
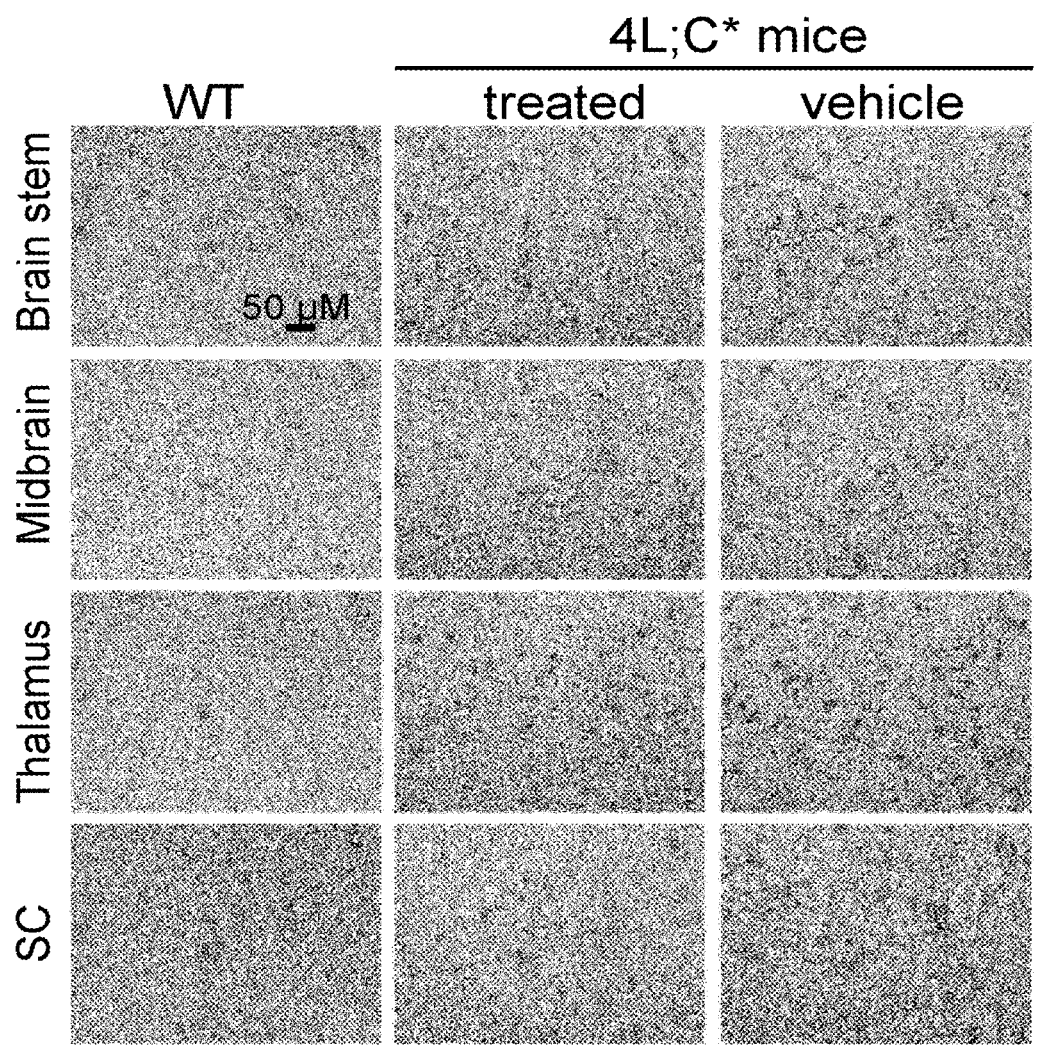
FIG. 4A-4D. Reduced CNS-inflammation in mNPC transplanted 4L;C*. The sections from 50-days-4L;C mice were stained with inflammation markers, anti-CD68 antibody (brown) (FIG. 4A) for activated microglial/macrophages and anti-GFAP (brown) (FIG. 4B) antibody for astrogliosis. Quantitative data showed significantly reduced CD68 (FIG. 4C) and GFAP (FIG. 4D) signals in brainstem, midbrain and thalamus of treated 4L;C mice compared to vehicle-4L;C* control, indicating decreased inflammation. Student's t-test. *, p<0.05, **, p<0.01.
Figure 4B:
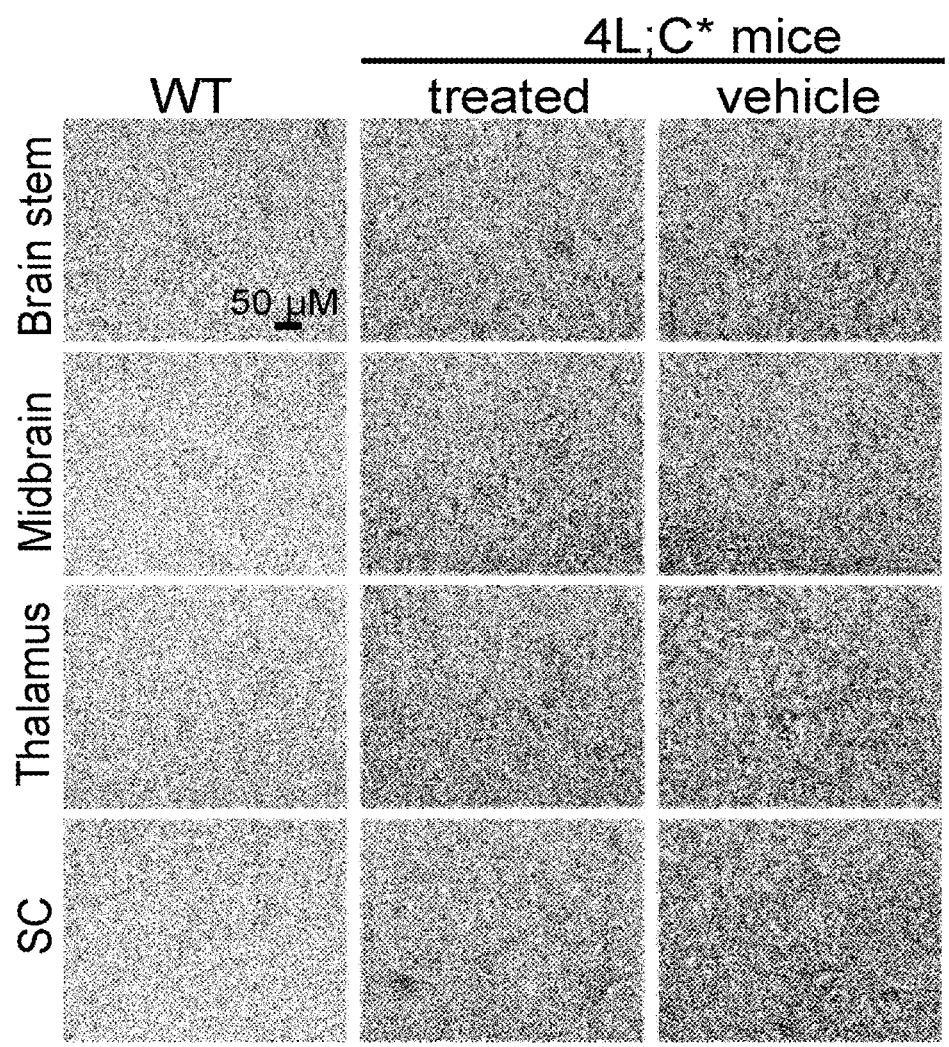
Figure 4C:
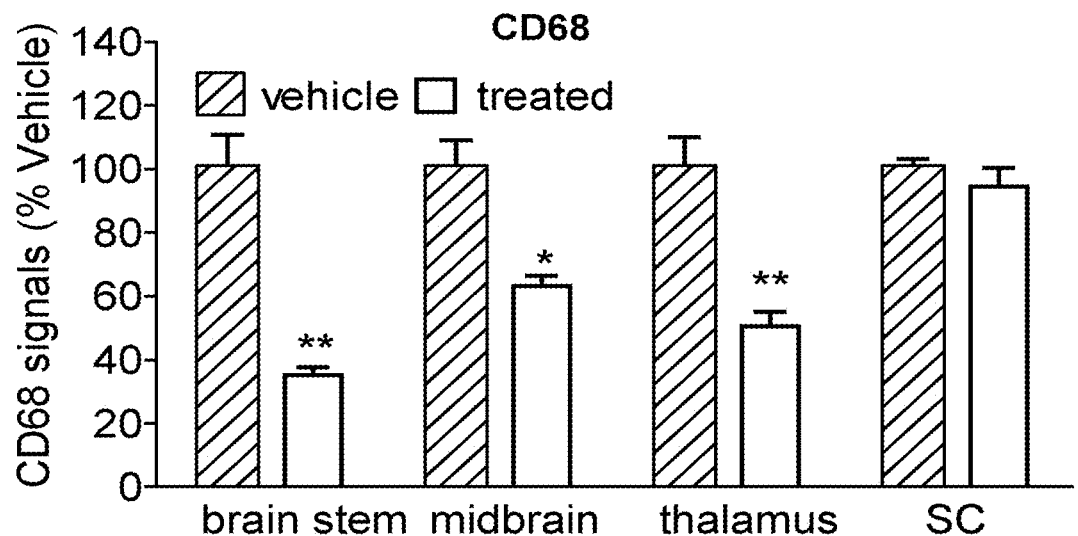
Figure 4D:
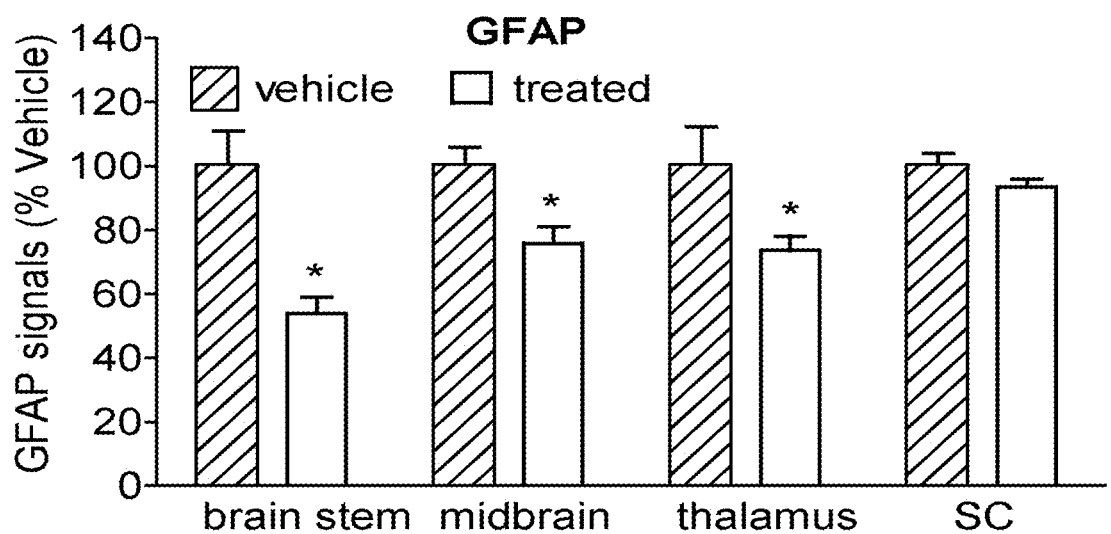
Figure 5:
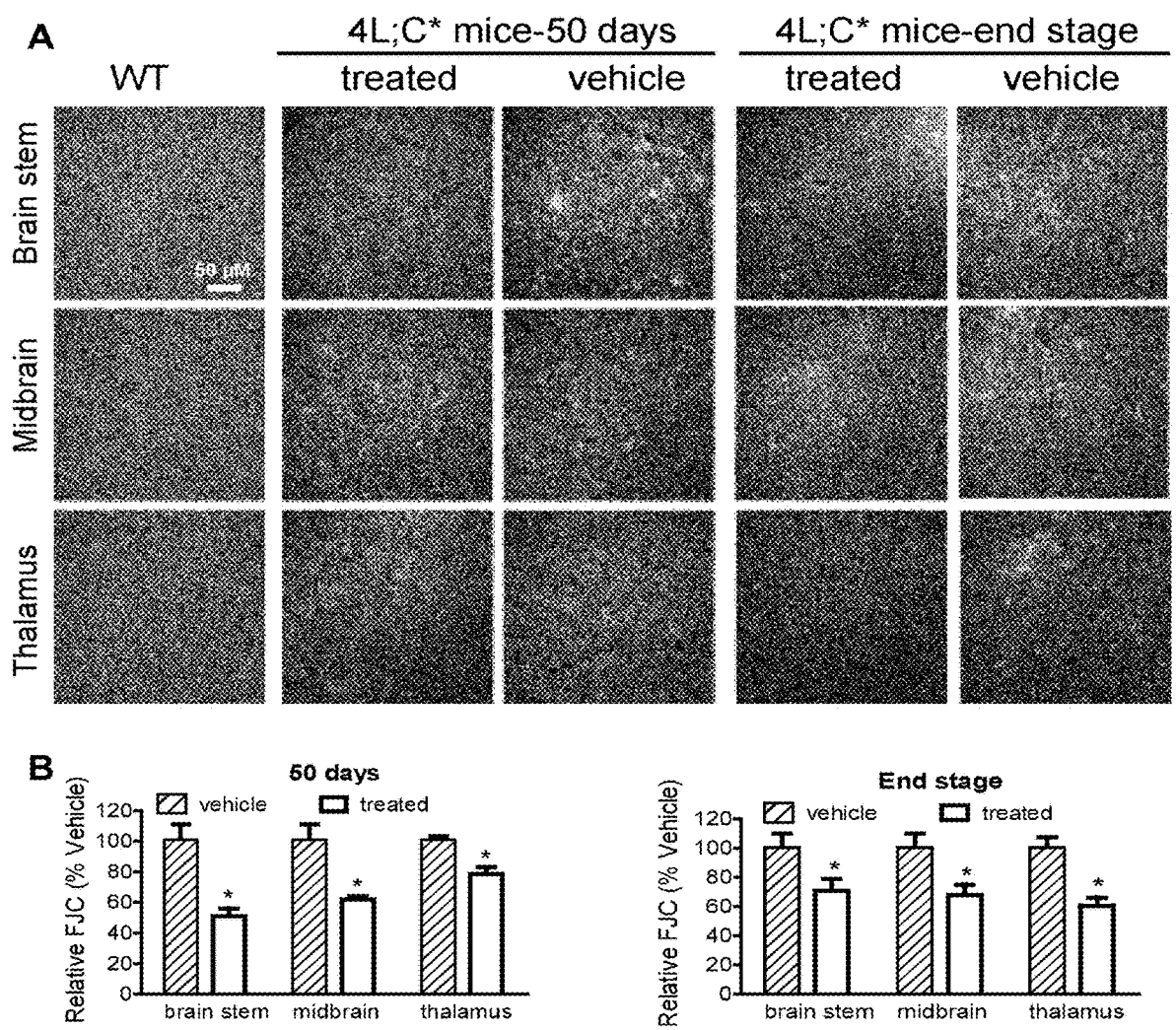
FIG. 5. mNPC transplantation mitigated neurodegeneration. Fluoro-Jade C- (FJC-) positive cells were examined in the mice brains at 50 days of age (A) and about 60 days of age at terminal stage in 4L;C* mice treated with mNPC or saline. FJC-positive signals were reduced in midbrain, brainstem and thalamus regions. Quantitative data showed significantly reduction of neurodegeneration (FJC signals) at 50 days of age and at terminate stage in mNPC treated 4L;C* brains compared to vehicle-4L;C* mice. Student's t-test. *, p<0.05. (B)
Figure 6A:
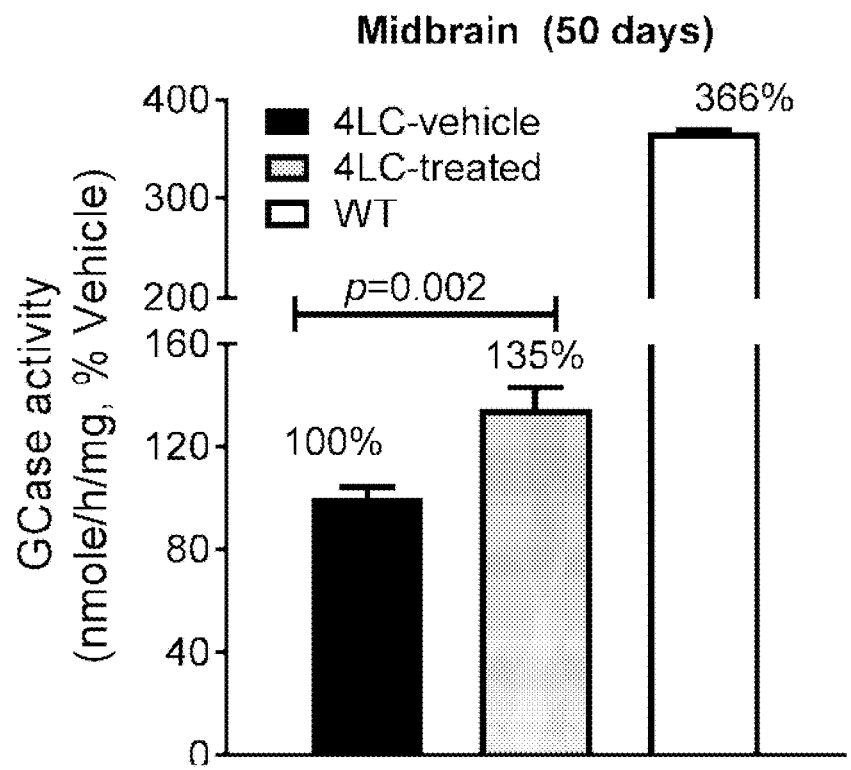
FIG. 6A-6F. Analyses of GCase and substrate levels in mNPC treated brain.
Figure 6B:
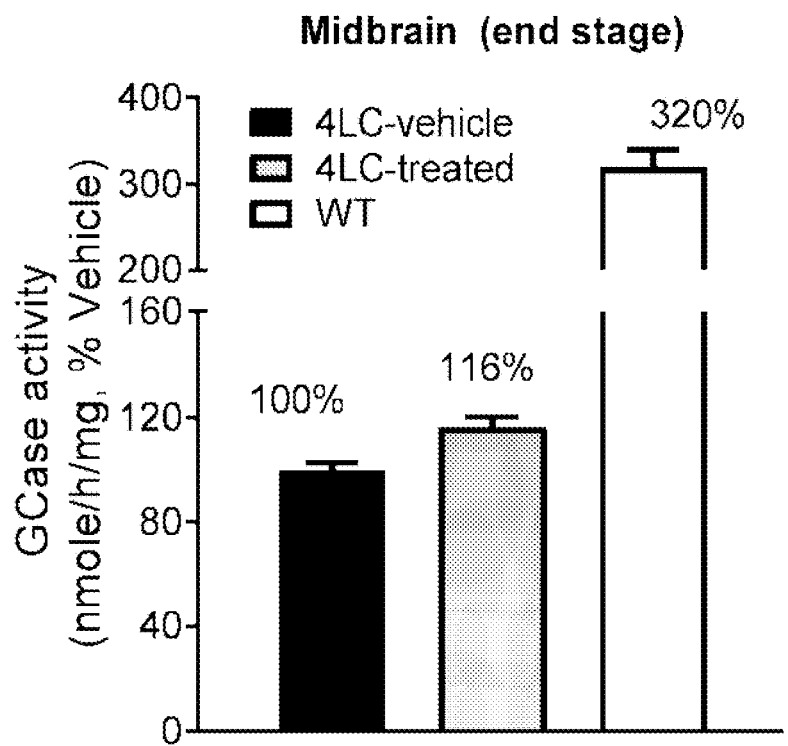
Figure 6C:
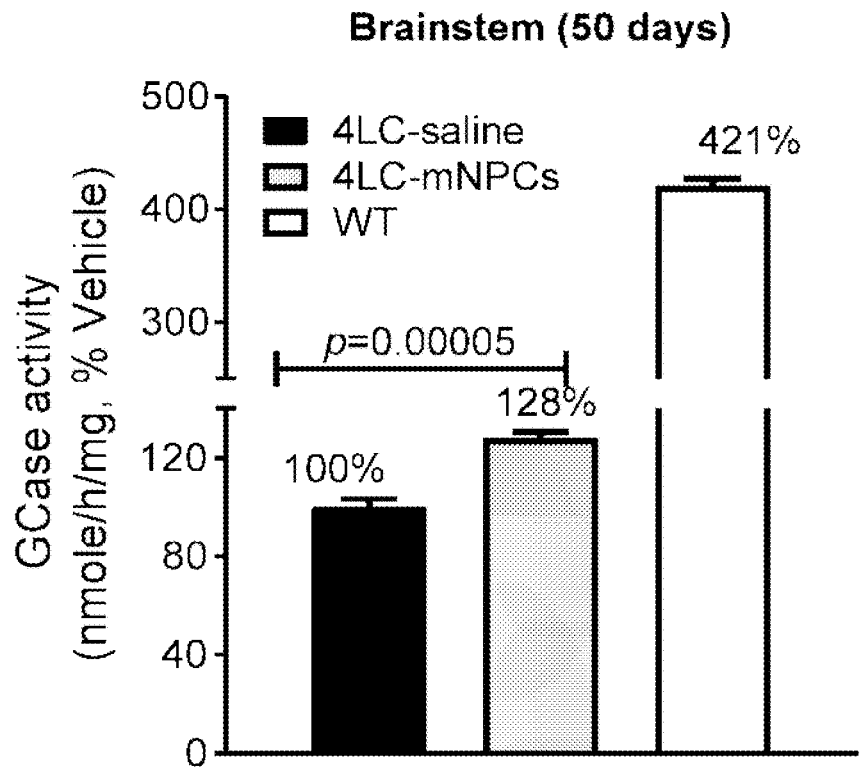
Figure 6D:
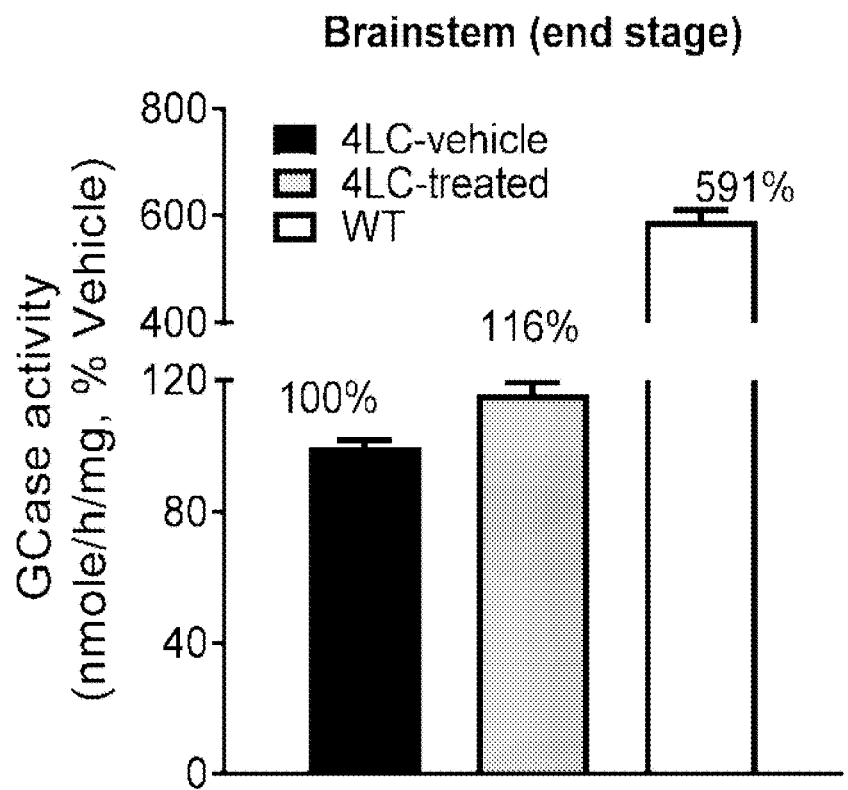
Figure 6E:
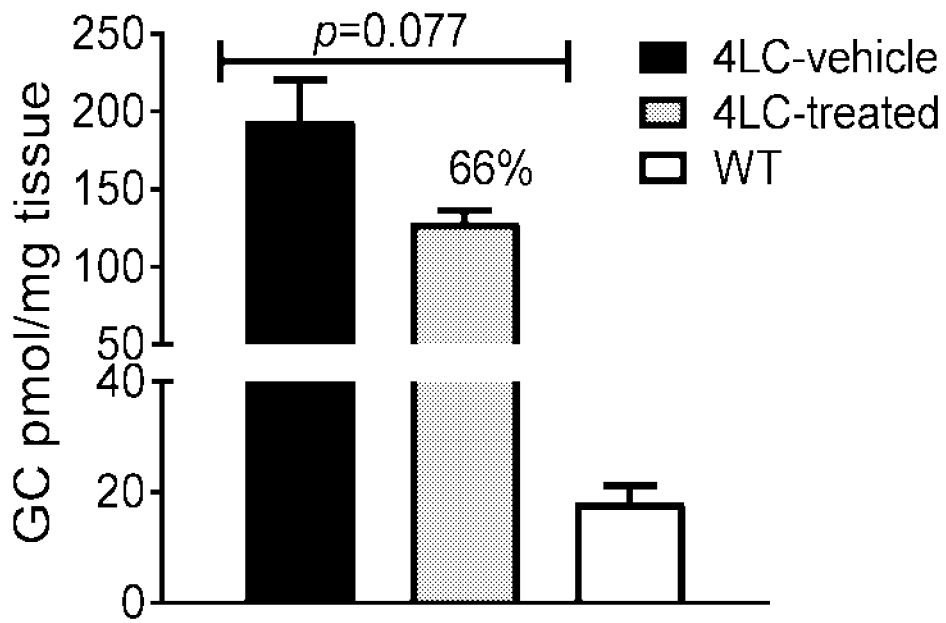
Figure 6F:
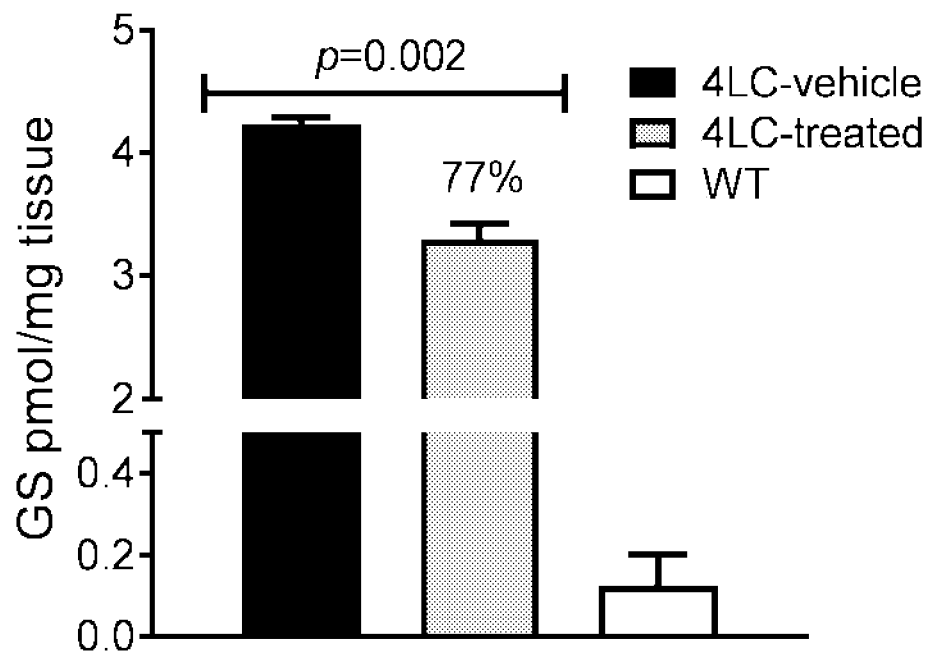
Figure 7:
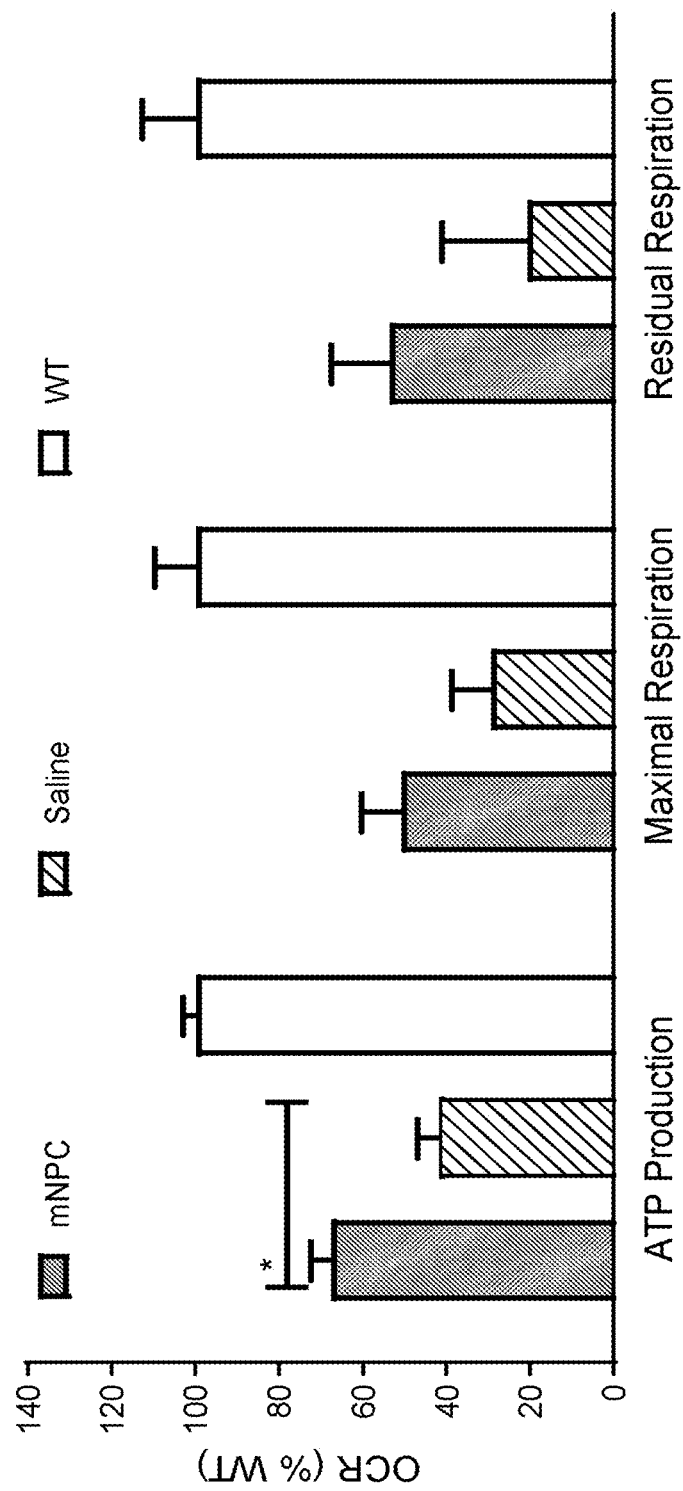
FIG. 7. Improved mitochondrial function in mNPC transplanted 4L;C* mice brain. Vehicle-4L;C* brain had decreased mitochondrial function with 42% of ATP production, 30% of maximal respiration, 21% of residual respiration OCR rate compared to WT brains. mNPC treatment improved 4L;C* brain ATP production, maximal respiration, residual respiration OCR rate to 64%, 66%, 64% of WT level, respectively. One-way ANOVA with post-hoc Tukey test (P<0.05), n=3 mice/group, 6 replicates/sample/assay, duplicate assays.
Figure 8A:
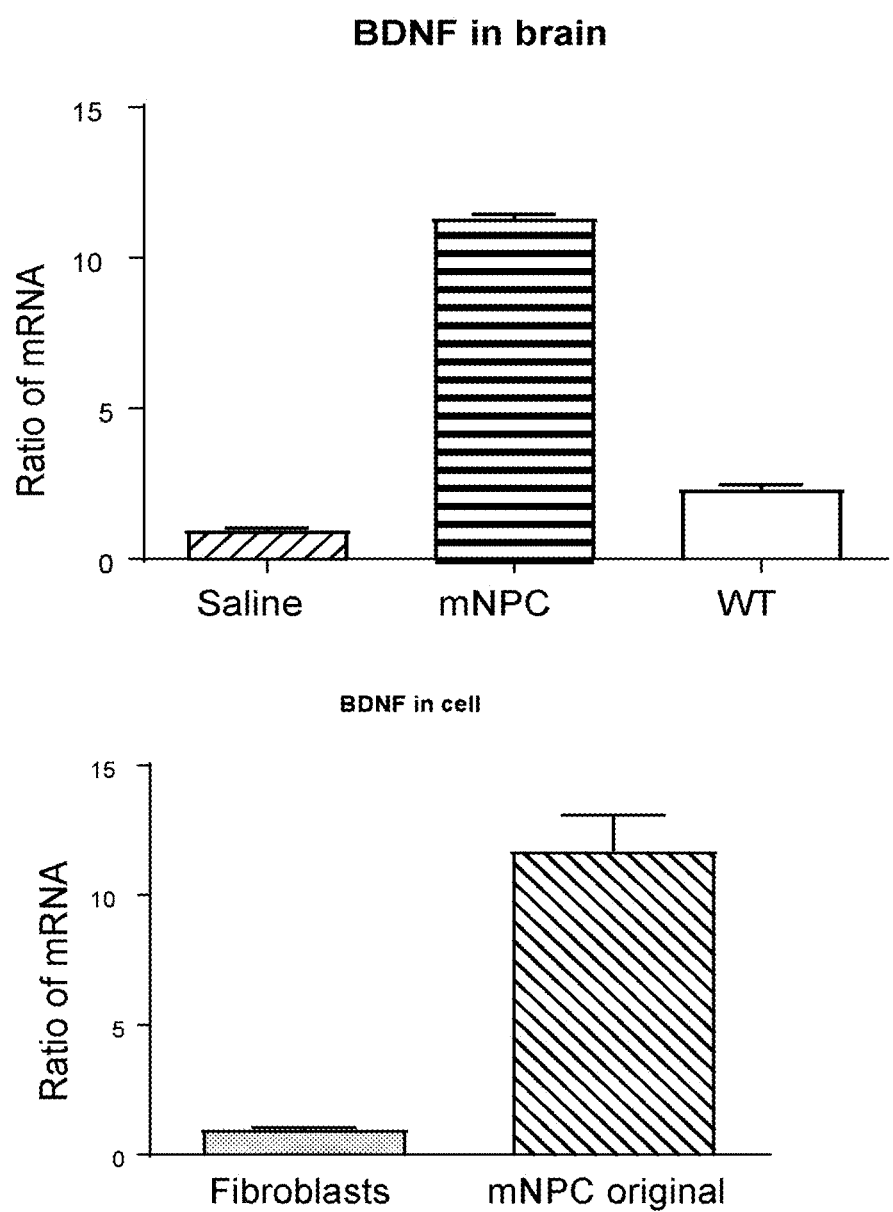
FIG. 8A-8D. The mRNA expression of neuron trophic factors in 4L;C* mice brain. The mRNA expression of BDNF (FIG. 8A), NT-3 (FIG. 8B) and GDNF (FIG. 8C) in 4L;C* brain were determined by qRT-PCR. BDGF, NT-3 and GDNF mRNA levels were increased at 1 mons after NPCs injection and slightly were decreased after four weeks. The mRNA expression of BDNF (FIG. 8A), NT-3(FIG. 8B) and GDNF (FIG. 8C) in cells were consistent with the results.
Figure 8B:
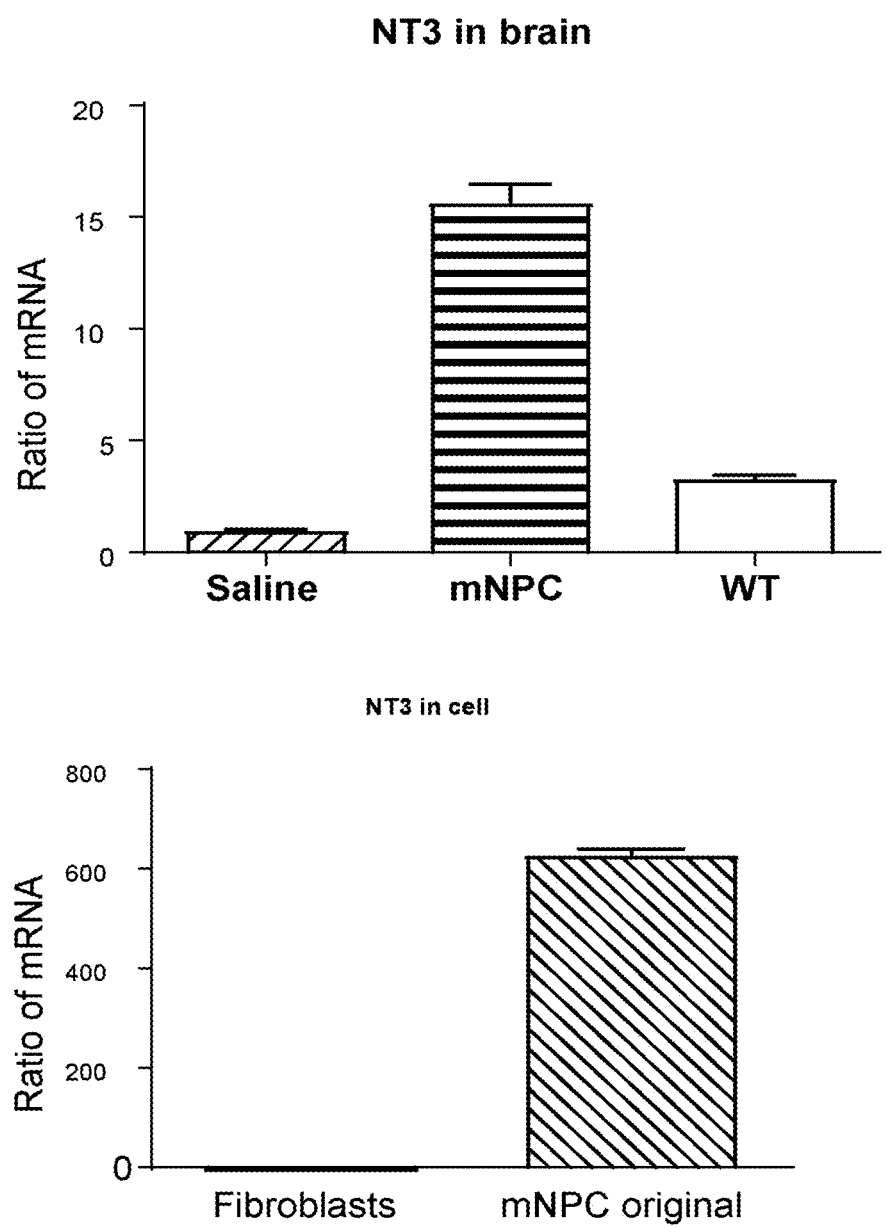
Figure 8C:
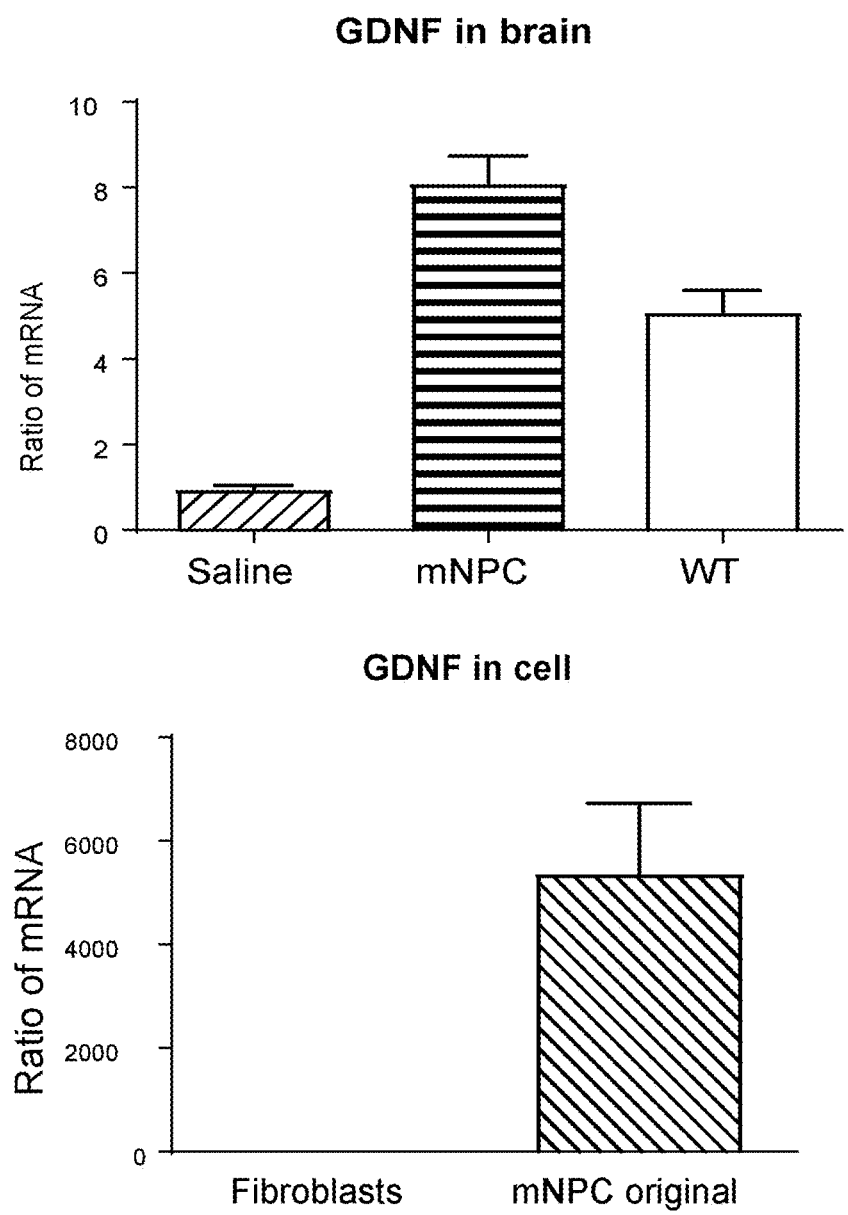
Figure 8D:
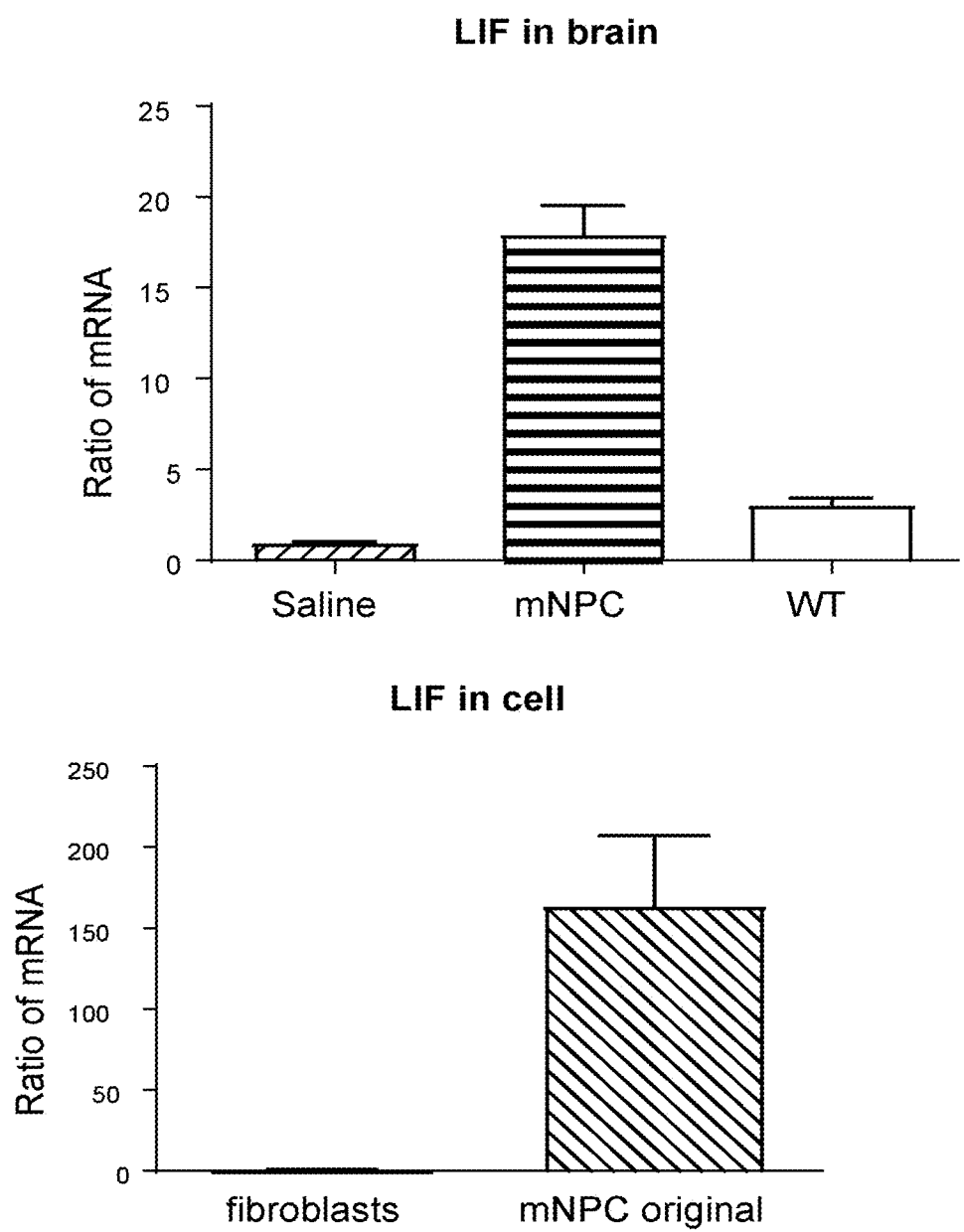
Figure 9A:
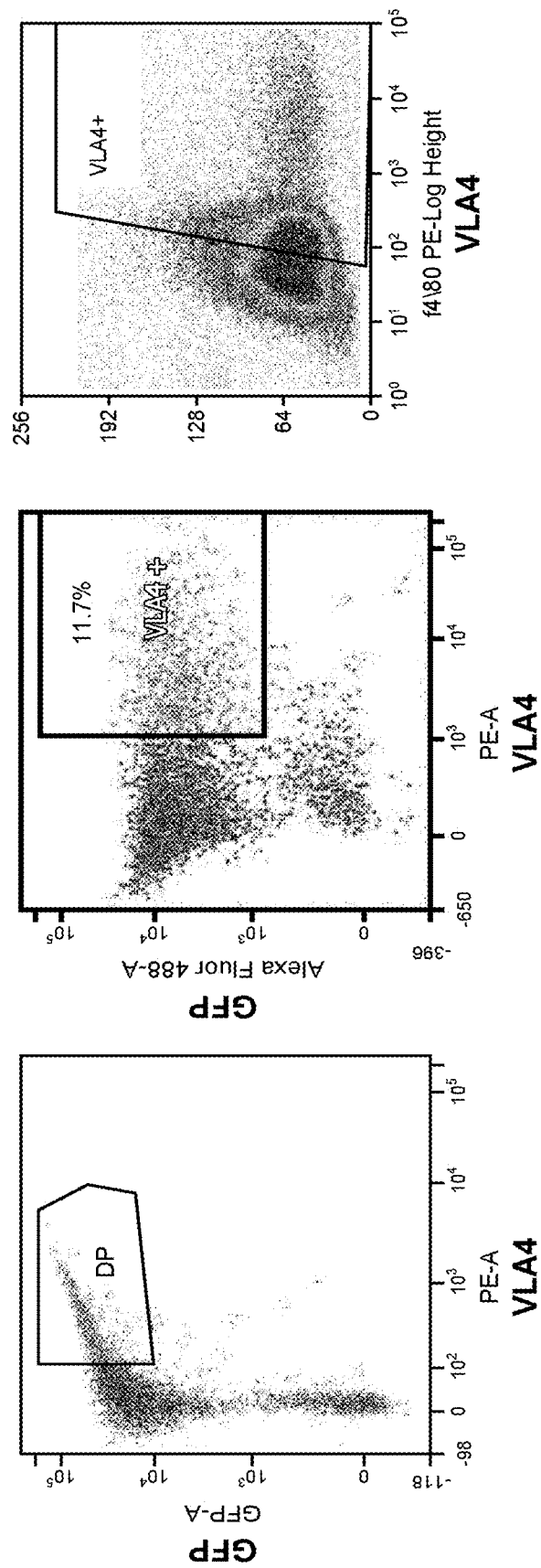
Figure 10:
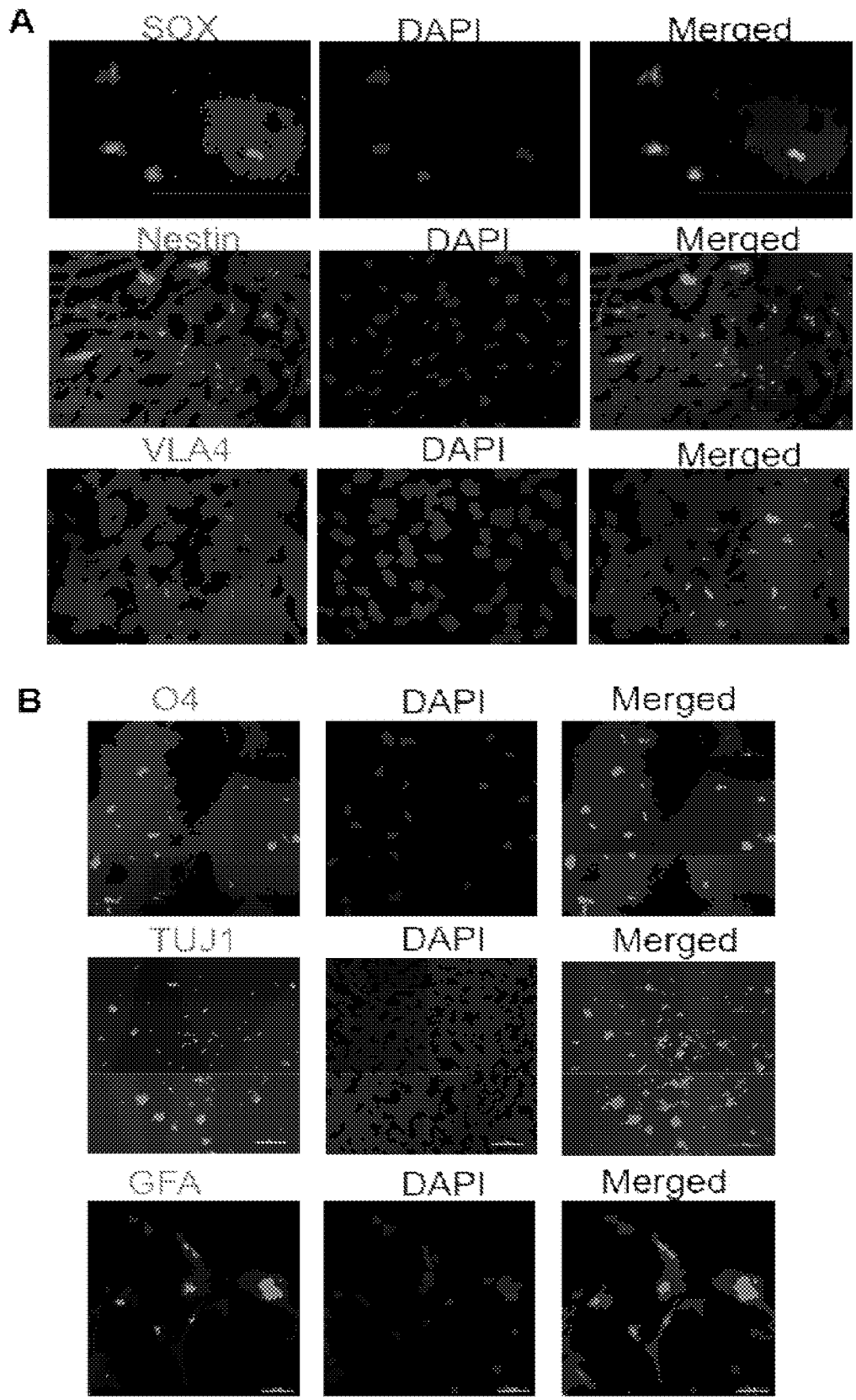
FIG. 10. VLA4+ human GD2 iPSC-derived NPCs maintain NPC properties and multipotency. Compared to total NPCs, VLA4+NPCs are stained positive for neural stem cell markers, anti-Nestin and anti-Sox2 (A), and have potency to differentiate into neurons (Tuj 1, red), oligodendrocytes (O4, red), and astrocytes (GFAP, red) (B). DAPI stains cell nuclei.
Figure 11:
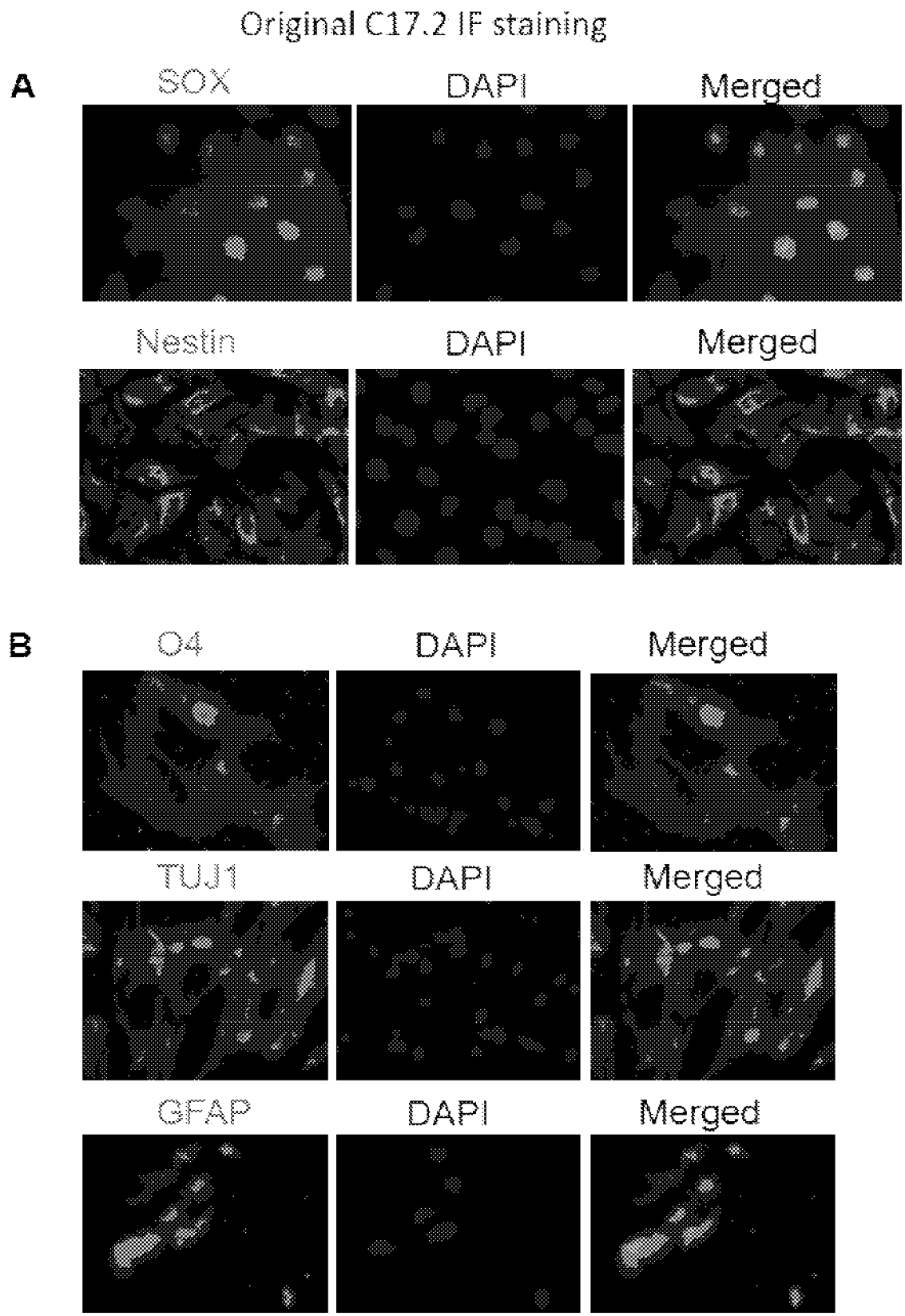
FIG. 11. Characterization of C17.2 cells. C17.2 cells have neural stem cells properties stained positive by anti-Nestin and anti-Sox2 antibodies (A) and have potency (B) to differentiate into neurons (Tuj 1, red), oligodendrocytes (O4, red), and astrocytes (GFAP, red). DAPI stains cell nuclei.
Figure 12:
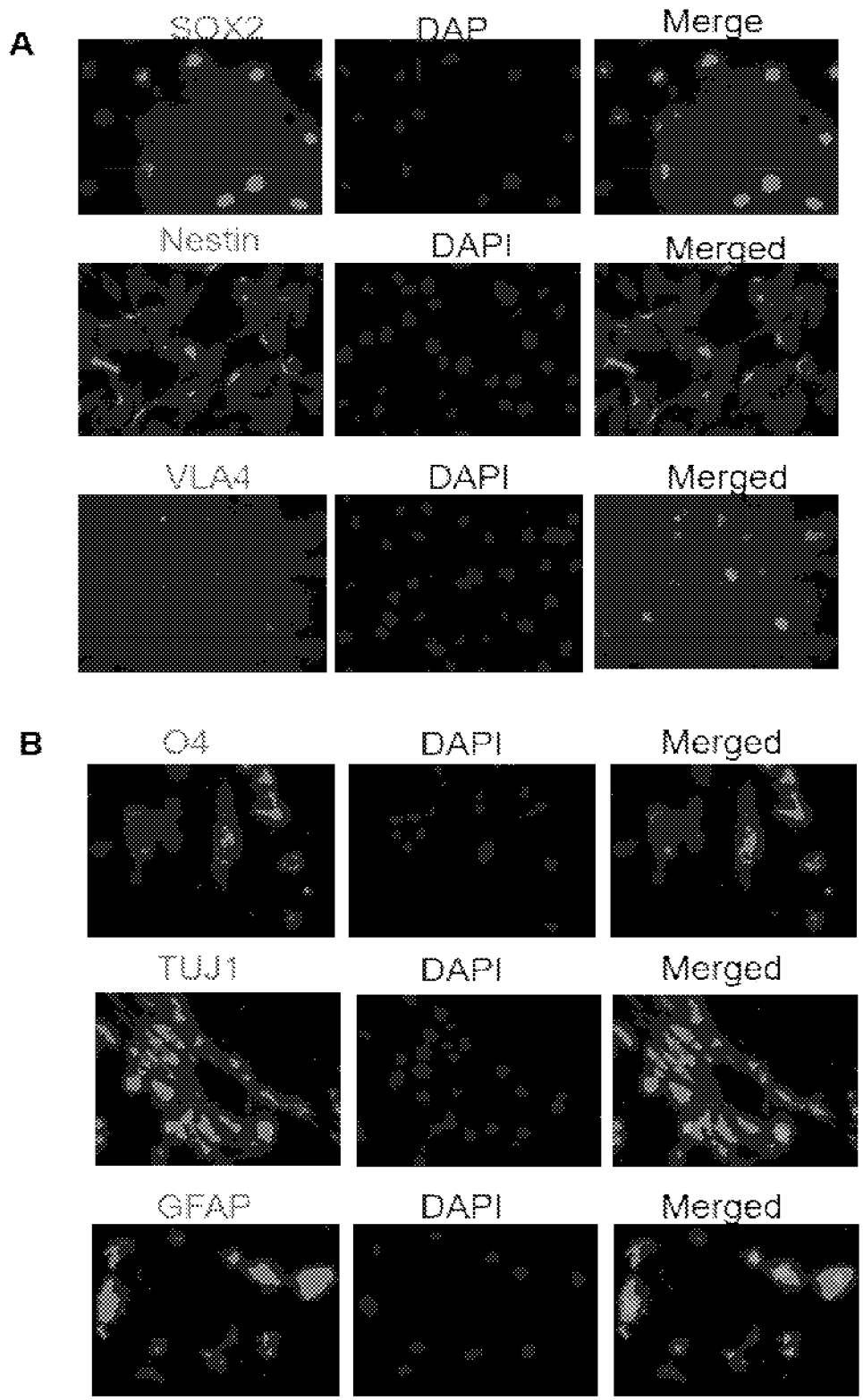
FIG. 12. Characterize VLA4+C17.2 cells. VLA4+C17.2 cells were isolated by FACS. (A) The FACS sorted cells were stained positive by anti-VLA4 antibody. VLA4+C17.2 cells were validated by neural stem cell markers, anti-Nestin and anti-SOX2 antibodies. (B) VLA4+C17.2 cells were differentiated into neurons (Tuj 1, red), oligodendrocytes (O4, red), and astrocytes (GFAP, red). DAPI stains cell nuclei.
Figure 14:
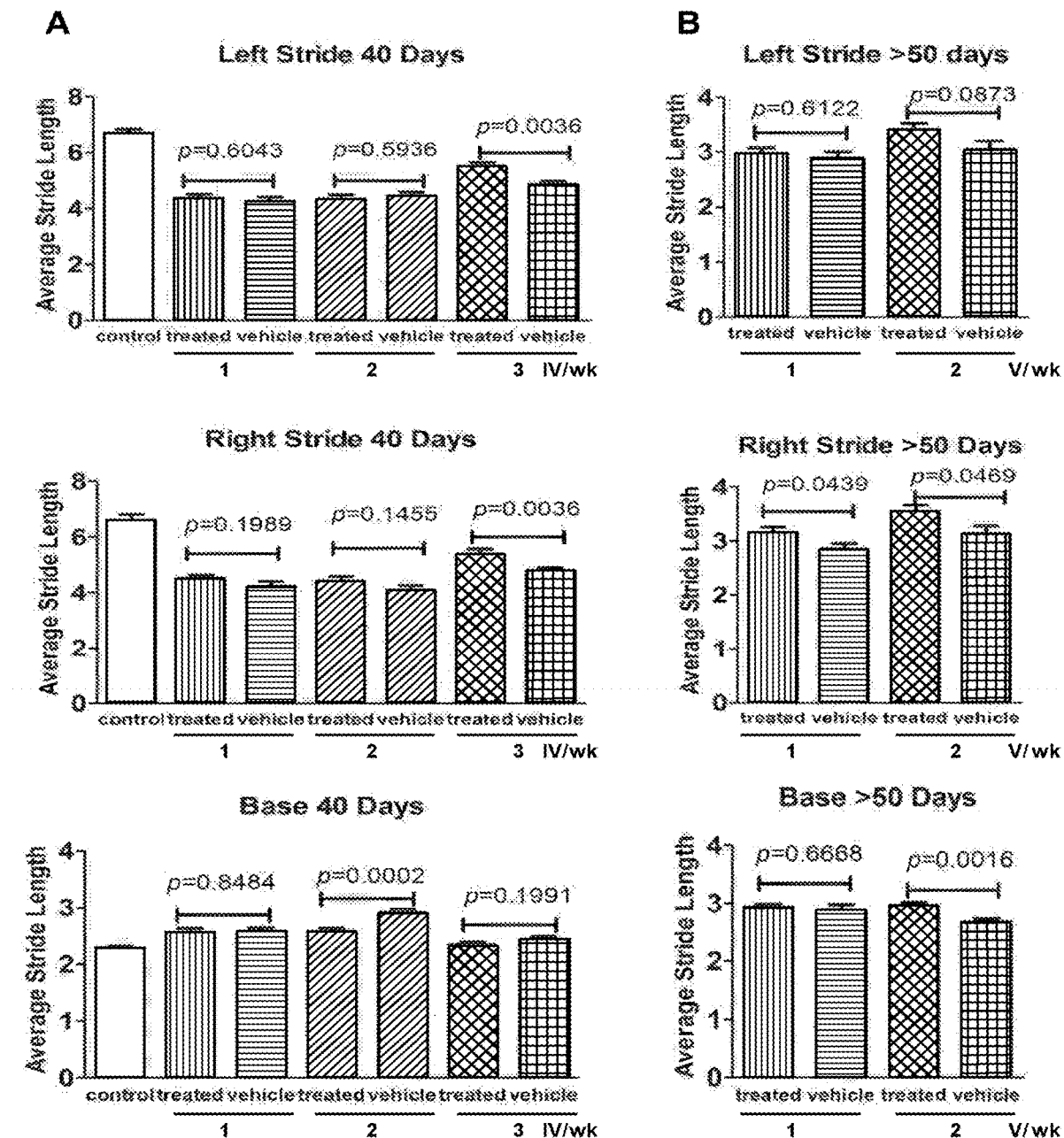
FIG. 14. Effect of transplantation of mNPCs on sensorimotor function. Gait analysis of 4L;C* mice at 40 days of age (A) and terminate stage (B). 4L;C* mice were administered mNPCs by one IV/week, two IV/week and three IV/week. Student's t-test.
Figure 15:
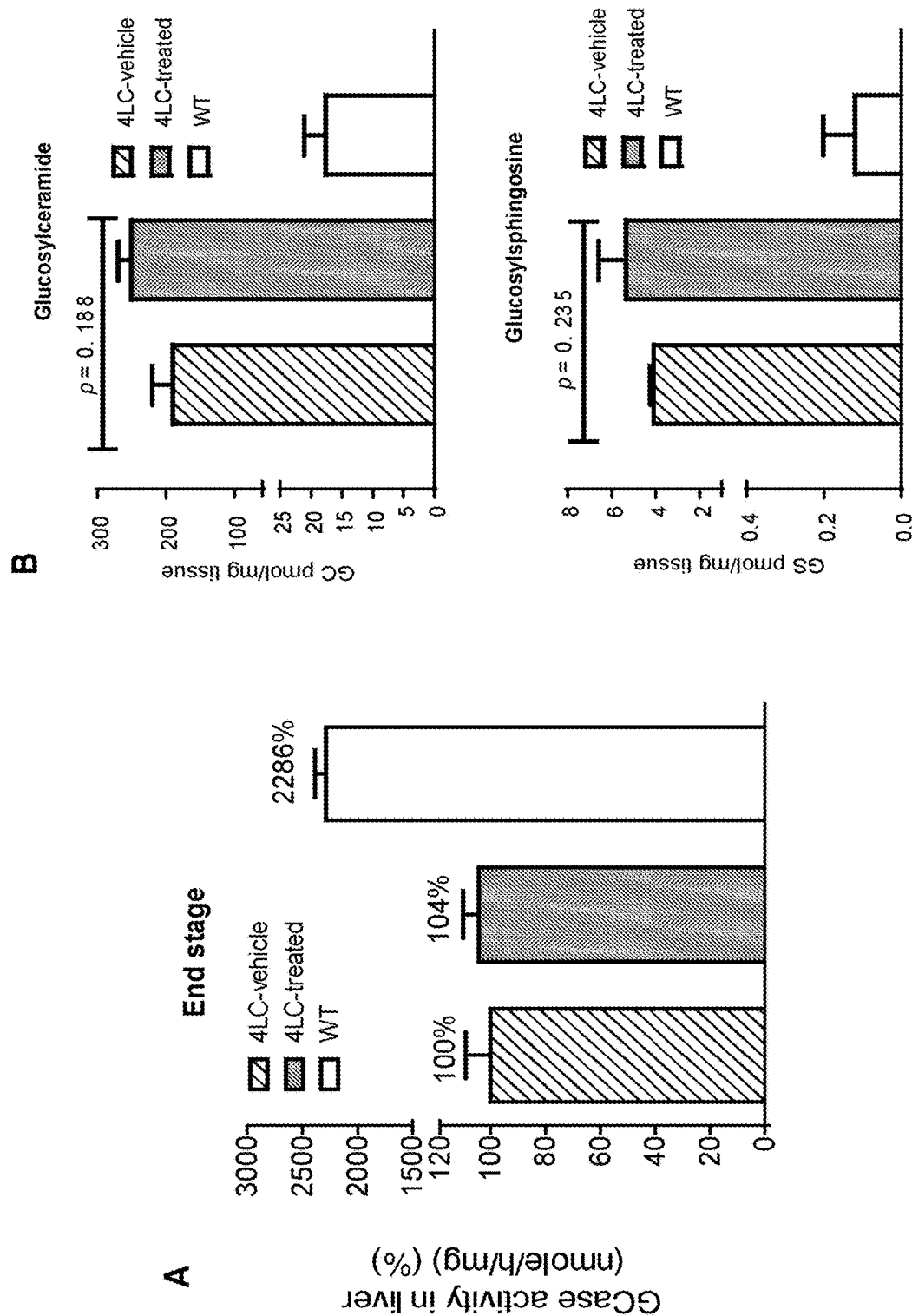
FIG. 15. Analysis of liver and brain from transplanted mice. (A) GCase activity in the liver was not altered in the mNPC treated 4L;C* mice compared to vehicle control at 50 days of age. (B) Substrate analysis in terminal age mice showed that GC and GS levels in NPC treated 4L;C* brain were not significant different from vehicle-4L;C*.
Figure 16A:
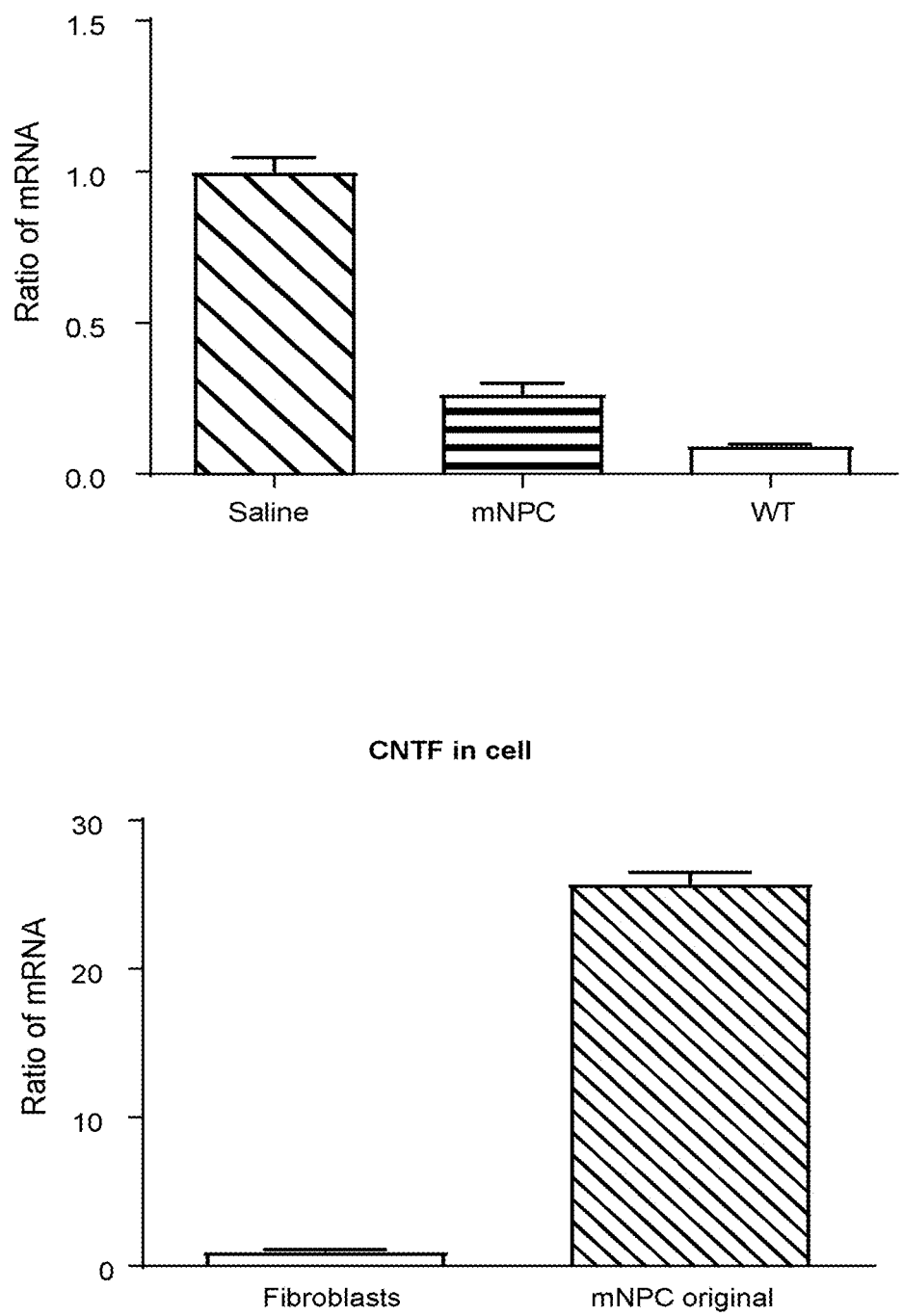
Figure 16B:
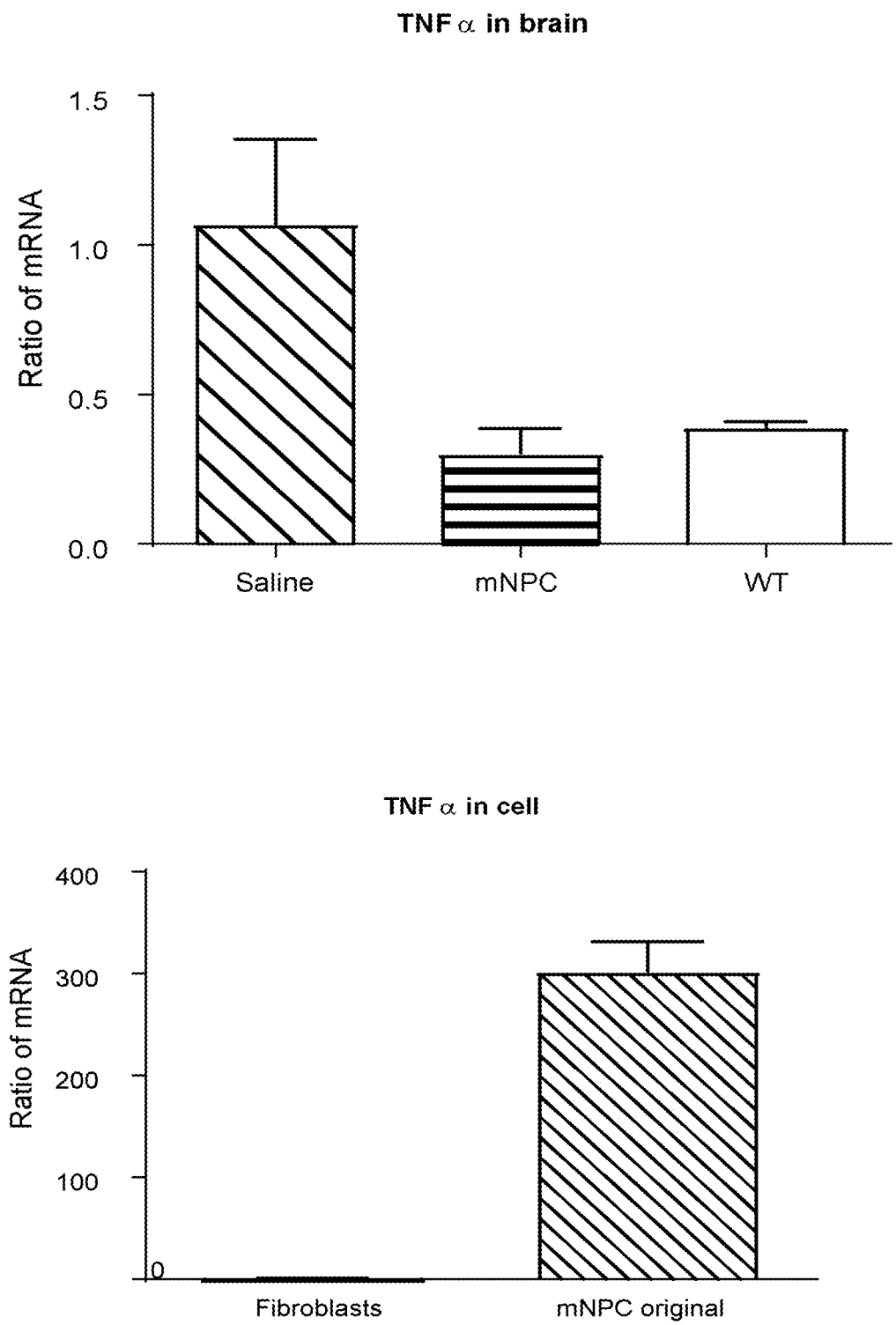
Figure 16C:
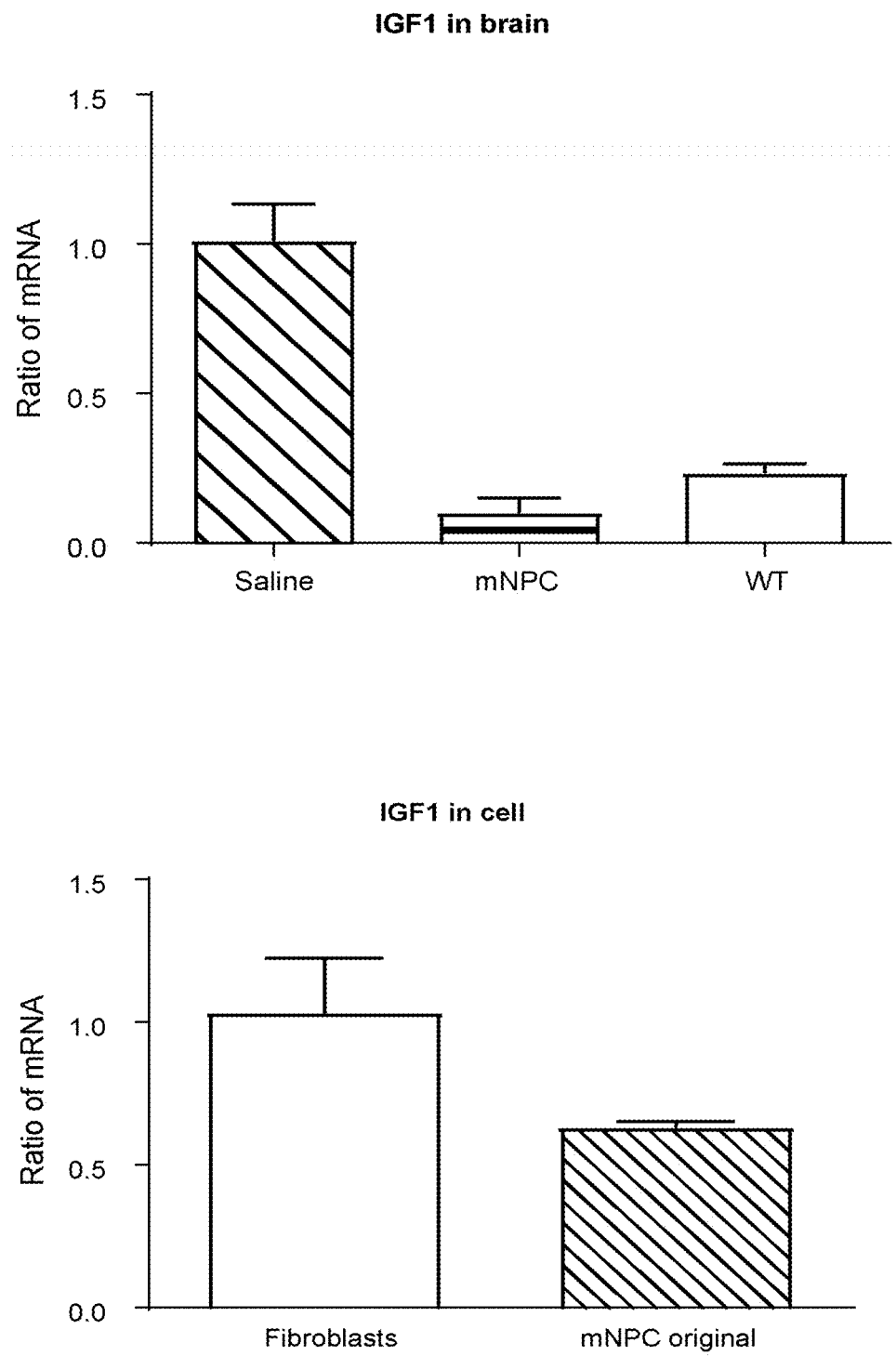
Figure 16E:
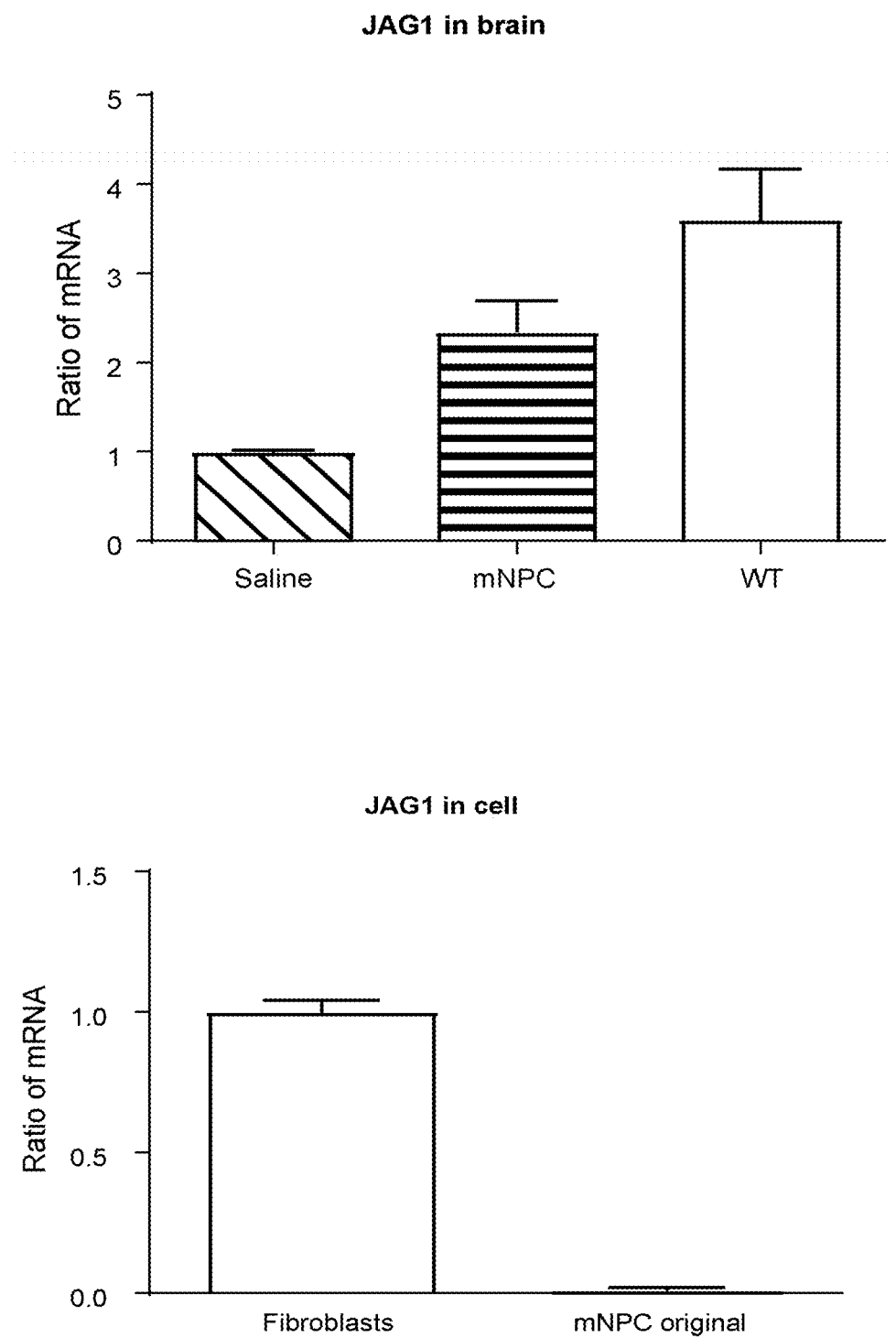
Figure 16F:
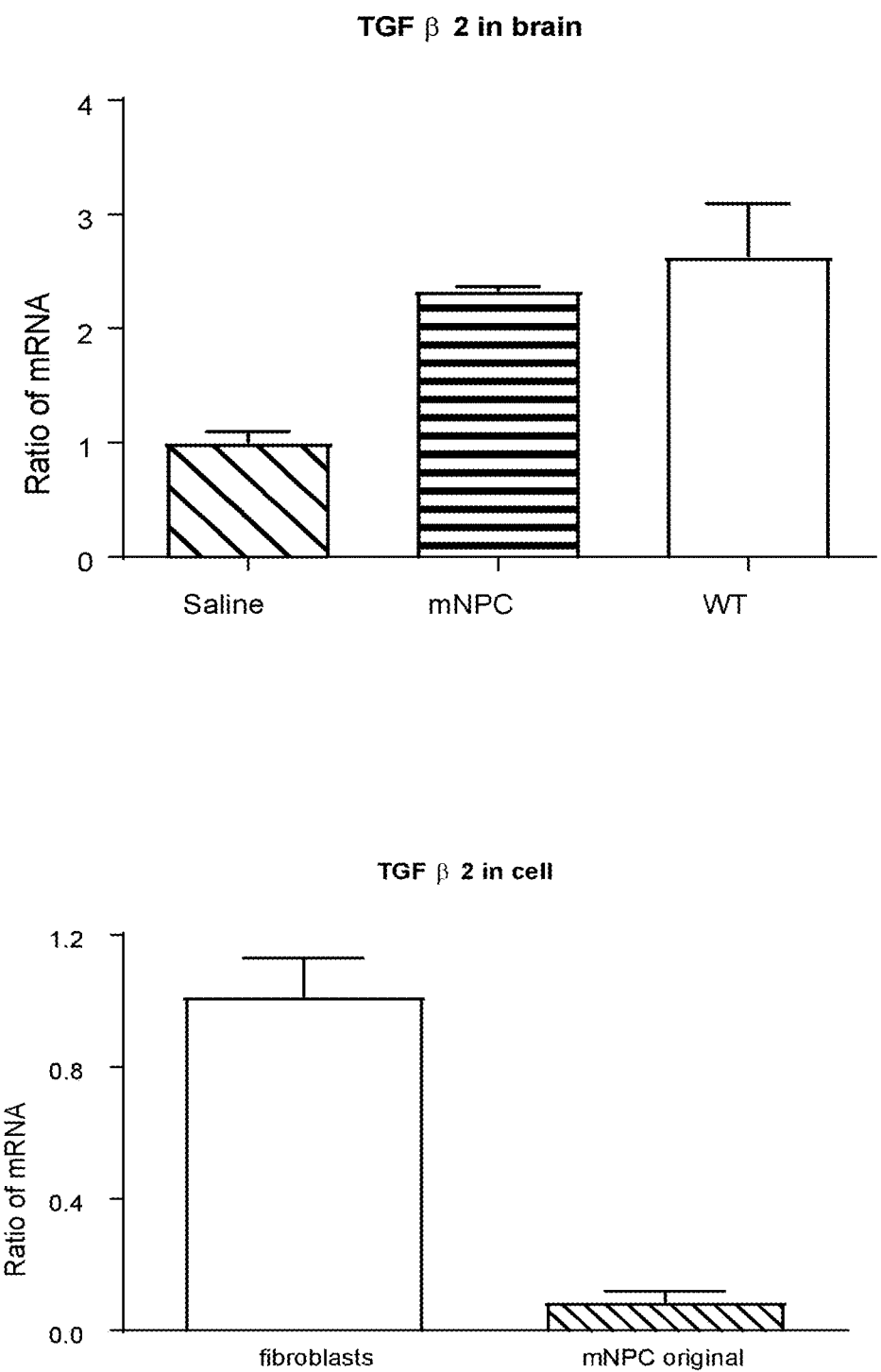
Figure 17:
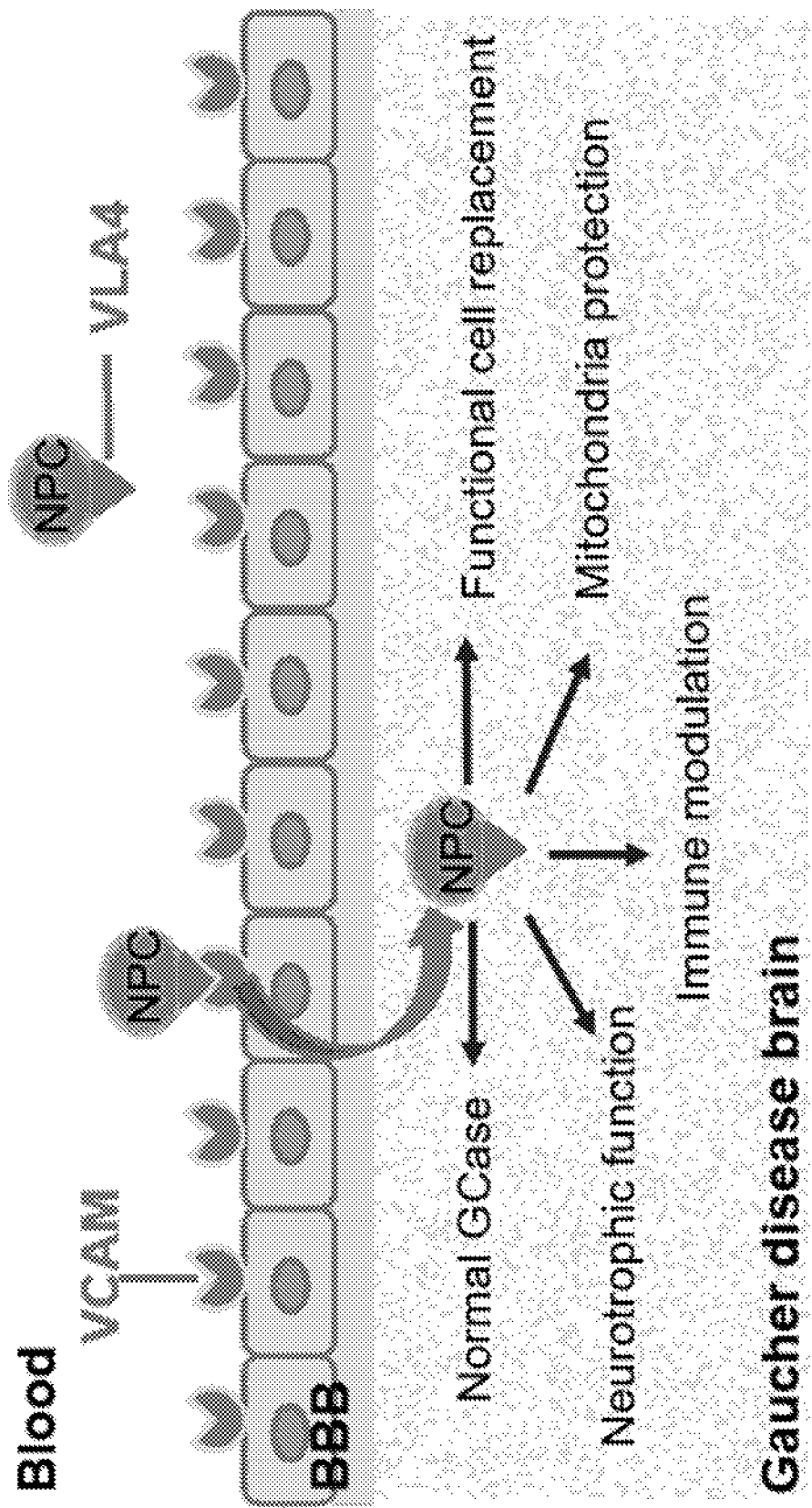
FIG. 17. Scheme: IV delivered VLA4+NPC cross BBB through interaction with VCAM1. The therapeutic efficacy was achieved by functional cell replacement, providing neurotropic function and normal GCase, protecting mitochondrial function, suppressing CNS inflammation neurodegeneration.
Figure 20:
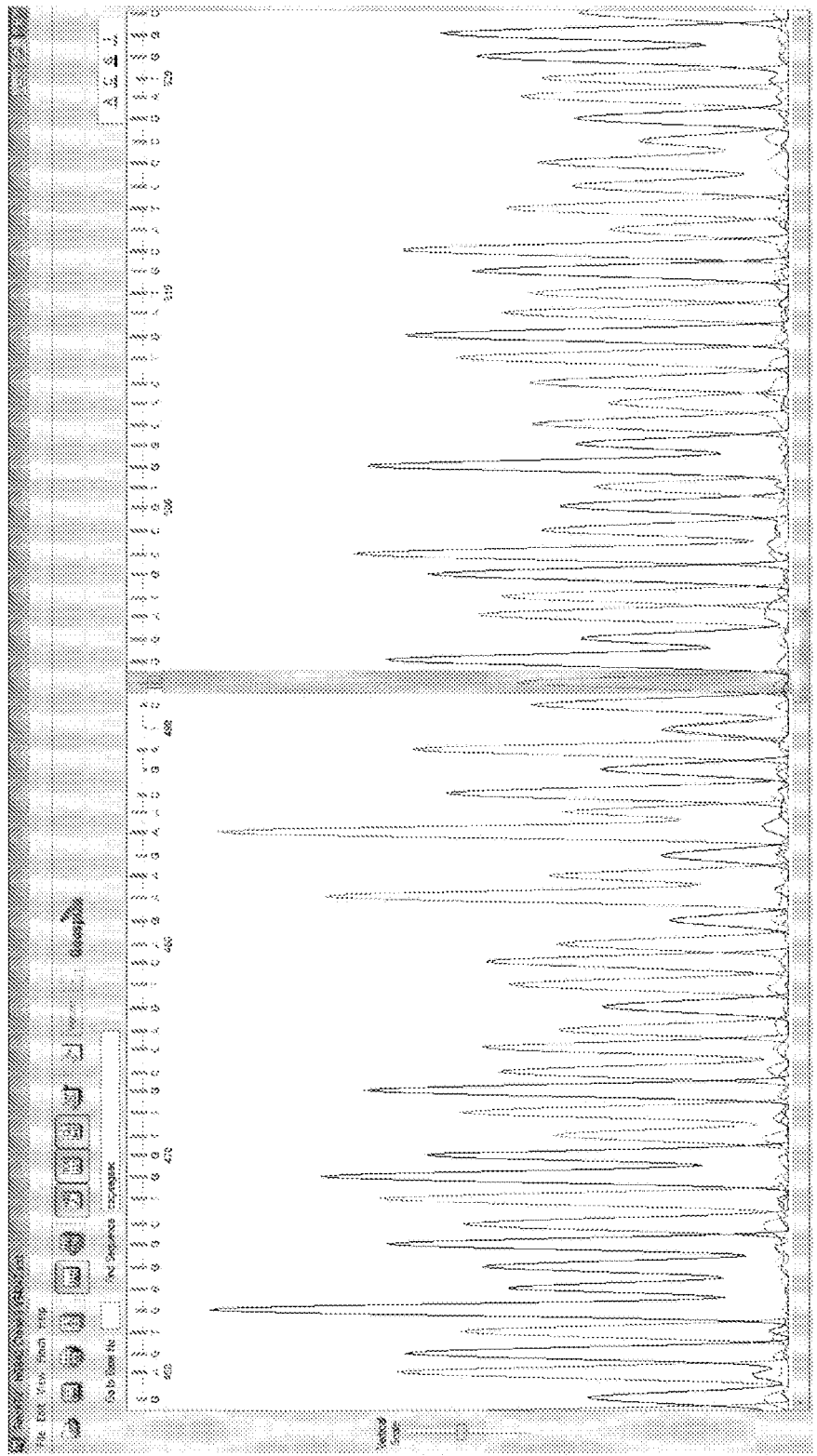
FIG. 20. Sequence of corrected clone 9. An example of the corrected clone #9 was verified for the correction of the mutant allele and not affect WT allele by Sanger sequencing.
Figure 22A:
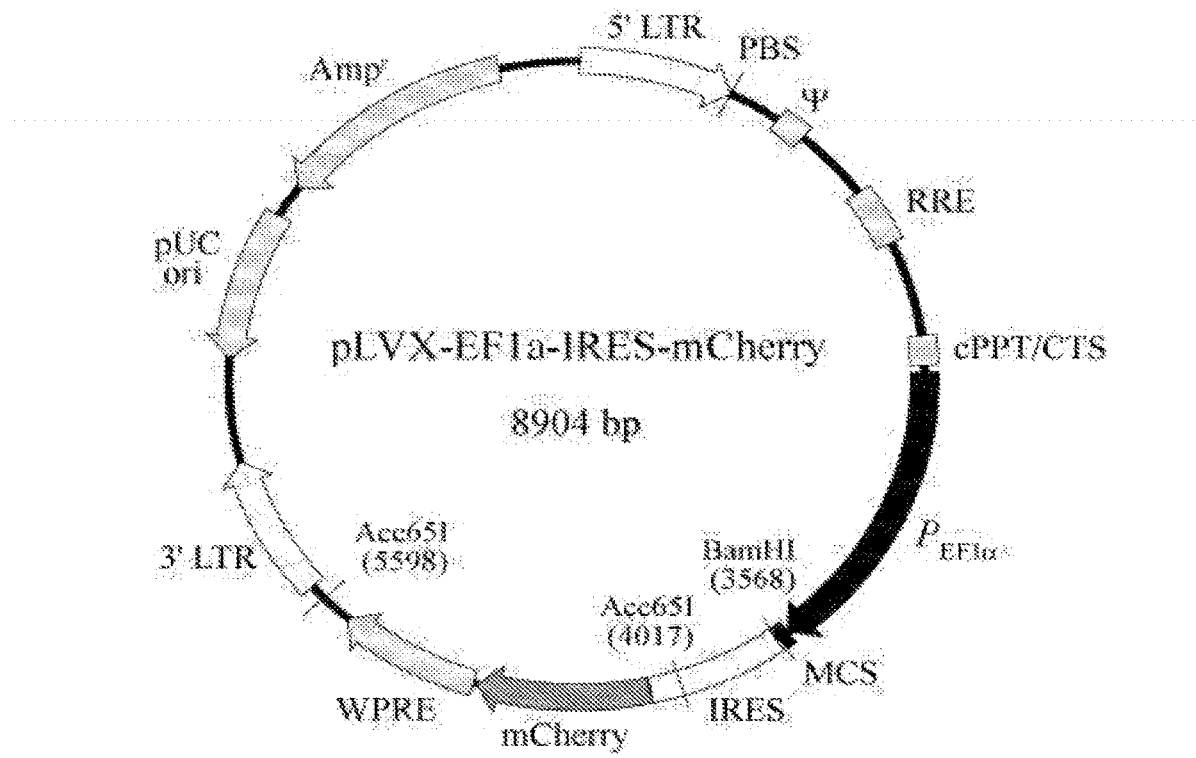
FIG. 22A-22B. Generation of human GBA1 expression lentiviral vector. Human WT GBA1 cDNA was cloned into the two lentiviral vectors (shown in FIG. 22A and FIG. 22B) using In-Fusion Cloning kit. The lentiviral vectors were packaged into viral particles. 1 and 2 showing cloning sites for each vector.
Figure 22B:
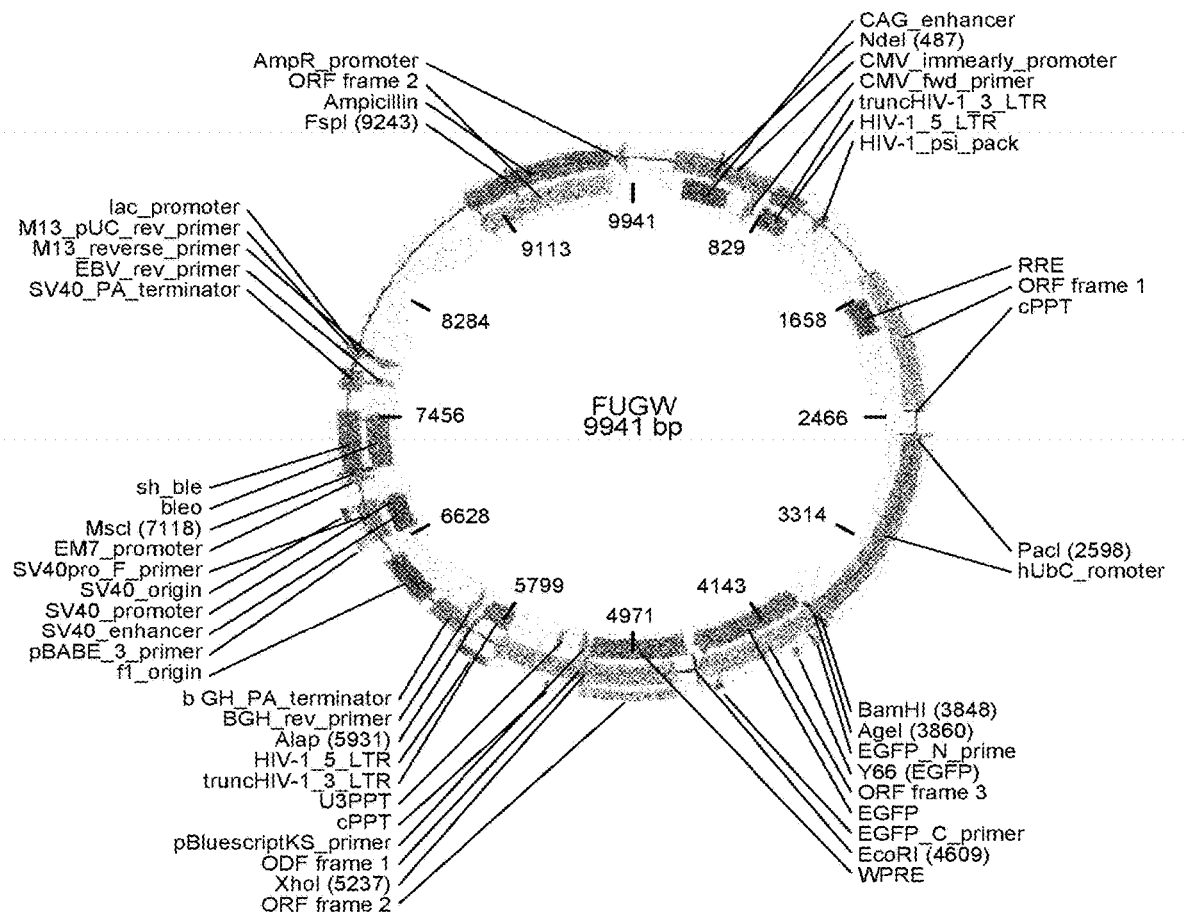
Figure 23:
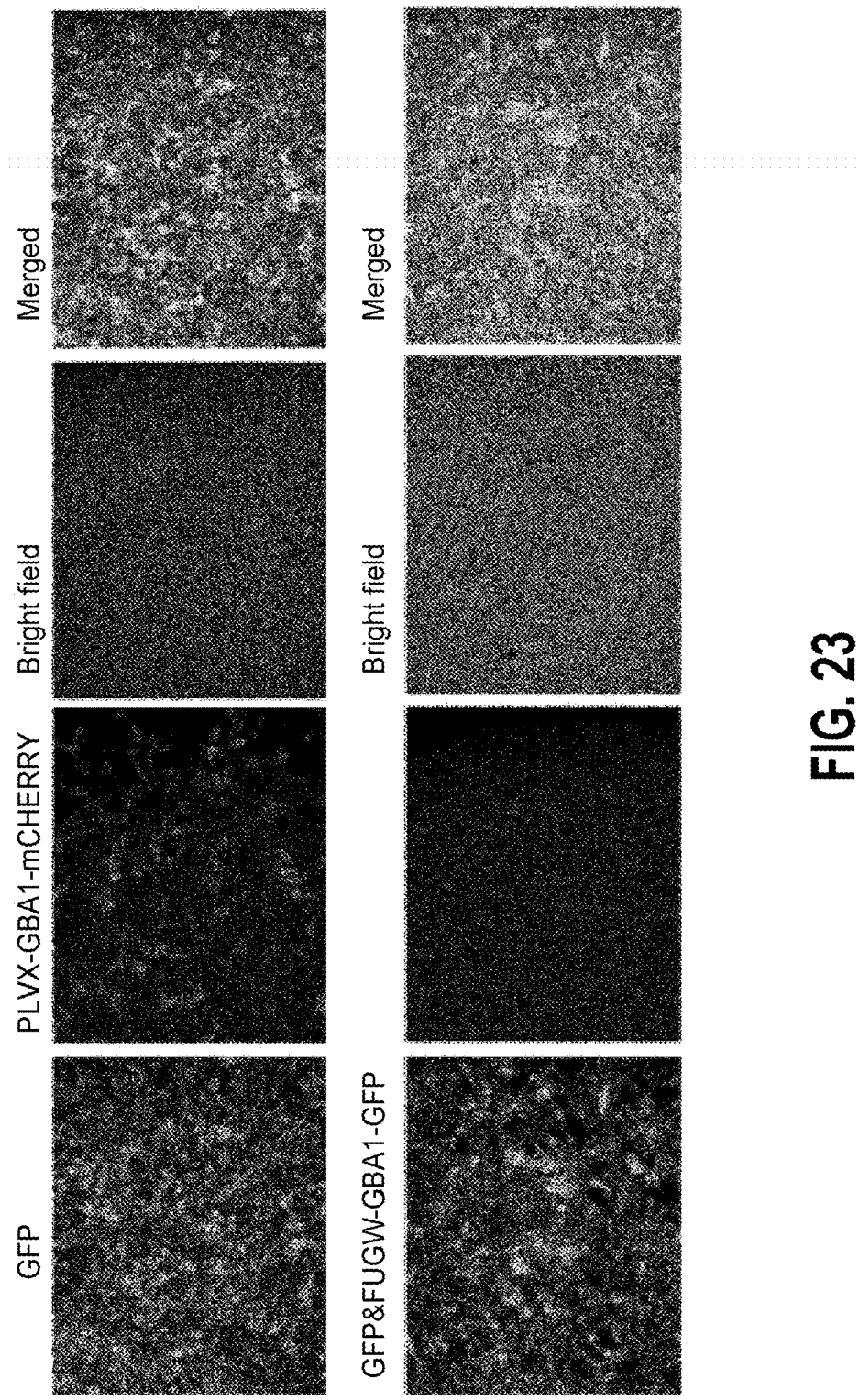
FIG. 23. If detection of lentiviral vector marker (mCherry or GFP) in GFP+VLA4+NPCs transduced with human GBA1 expression lentiviral particles.)
Figure 24:
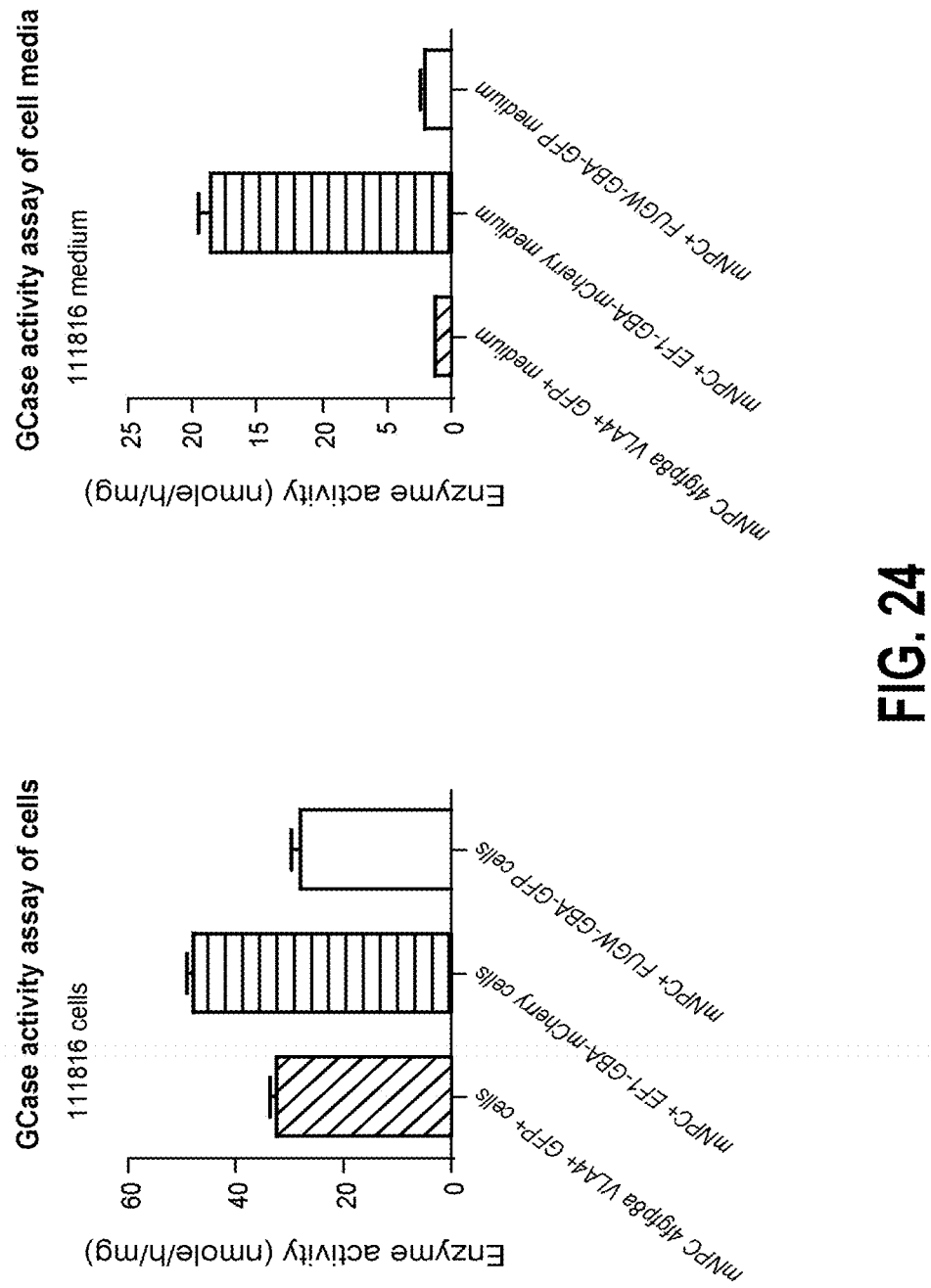
FIG. 24. GCase activity assay determined that human GBA1 was expressed and secreted in the NPCs transduced by lentiviral vector PLVX-GBA1-mCHERRY that was used in following cell and mice studies. Lentiviral vector FUGW-GBA1-GFP transduced cells did not have significant GCase secretion and was not used for following studies.

The single stranded guide (g) RNAs are designed to target the mutation, L444P (GBA1 mutation at nt14446, T>C) on iPSCs (See, e.g., FIGS. 1 and 2). The corrected clones are verified for the correction of the mutant allele and no effect on WT allele by DNA sequencing (FIG. 3). The construction of gRNA, validation of gRNA editing activity and DNA sequence in iPSCs are carried out in CCHMC Transgenic Animal & Genomic Editing Core using methods known in the art. The corrected iPSC clones carry heterozygous GBA1 mutations P415R (wt/P415R). Because GD is autosomal recessive disease, people with heterozygous GBA1 mutation, like GD carrier, have sufficient GCase function to live normal life.

Corrected GD-iPSC clones are assayed for GBA1 encoding enzyme acid β-glucosidase (GCase) activity to confirm restoring GCase in corrected clones. Corrected clones (herein referred to as #9, #27, #44) recovered GCase activity at ~40-47% of normal level, compared to the control H1 clone with normal GBA1 gene (FIG. 4), which reached heterozygous GBA1 levels.

Corrected GD-iPSC can be validated for chromosome normality by Karyotyping. The edited iPSCs can be derived to NPCs and FACS sorted for VLA4+ population. The corrected VLA4+NPCs can then be tested for multipotency. In vivo efficacy of corrected VLA4+NPCs can then be evaluated in animal models by intravenous injection, a noninvasive procedure, to assess the ability of the corrected cells to engraft in the mouse CNS and provide short-term amelioration of substrate accumulation and inflammatory phenotypes in the GD mouse brain (transplanted human NPCs survive only 1-2 months in the CNS of immunocompetent mice). In parallel, uncorrected GD and normal human iPSC-derived NPCs can be analyzed.

Genetically edited GD-iPSCs may be used as a personalized therapy by autologous cell replacement (NPCs and other cell types) treatments for GD patients, with wider applications in Parkinson's disease.

Methods

Generation of human GBA1 expression lentiviral vector. Human wild-type GBA1 cDNA is from Origene™ Technologies (GBA (untagged)-Human glucosidase, beta, acid (GBA), transcript variant 3, NM_001005742.1). The full-length GBA cDNA is cloned into flap-Ub promoter-GFP-WRE lentiviral expression vector (Addgene, Plasmid #14883) and pLVX-EF1α-IRES-mCherry Vector (Clontech, Catalog No. 631987) using In-Fusion Cloning kit (Clontech). The GBA1 clones are confirmed by DNA sequencing. The lent vector constructs are packaged into viral particles using HEK293T cells and lentiviruses are produced at Cincinnati Children's Hospital Medical Center vector core using methods known in the art. The titer of pLVX-EF1α-GBAHRES-mCherry and FUGW-GBAHRES-EGFP lentivirus are 8.13 E+07 and 3.51 E+06, respectively.

Transduction of NPCs with lentiviral hGBA1. WT VLA4+GFP+NPCs are plated at $7 \times 10^4$ cells/well in 6-well plate. The cells are transduced with Lentivector PLVX-GBAHRES-mCherry (MOI=23) and FUGW-GBAHRES-EGFP (MOI=1), respectively, in serum-free medium in the presence of Polybrene (4 μg/ml) (an enhancer reagent of retrovirus-mediated gene transduction). Transduced cells are sorted by FACS for GFP or mCherry-positive cells that contained FUGW-GBA1-GFP or pLVX-EF1α-GBA1-IRES-mCherry. The transduced NPCs are fixed by 4% PFA and evaluated for GFP or mCherry signals by Phase contrast and immunofluorescence using conventional fluorescence microscopy (Zeiss Axiophot; Oberkochen, Germany).

GCase activity assay. The cells are homogenized in 1% Na-taurocholate/1% Triton X-100 (Tc/Tx). Mouse tissues are homogenized in 1% Tc/Tx. GCase activity is determined fluorometrically with 4MU-Glc as substrate in 0.25% Tc/Tx diluted in 0.1M citrate phosphate (CP) buffer (pH 5.6) as described. Liou, B. et al. Analyses of variant acid beta-glucosidases: effects of Gaucher disease mutations. J Biol Chem 281, 4242-53 (2006). Mouse brains are homogenized in 1×PBS and incubated in 5 mM brain phosphatidylserine. The GCase activity assay is carried out in 0.1M CP buffer (pH 5.6) using 4MU-Glc as substrate as described. (Xu, Y. H. et al. Dependence of reversibility and progression of mouse neuronopathic Gaucher disease on acid beta-glucosidase residual activity levels. Mol Genet Metab 94, 190-203 (2008).) Protein concentrations of cells and tissues were determined by BCA assay using BSA as standard.

Genomic editing patient iPSC clones. The iPSCs are derived from both human GD patients and normal individuals as described in (Sun, Y., et al. (2015) PLoS One 10(3): e0118771). The clone selected for correction is iPSC47_36 that carries compound heterozygous GBA1 mutation (P415R/L444P). The single stranded guide (g) RNA was designed to target spCas9-mediated double strand break introduction proximal to the L444P mutation (GBA1 mutation at nt14446, T>C) in iPSC47_36. Oligonucleotides (caccGAAGAACGACCcGGACGCAG (SEQ ID NO:29) and aaacCTGCGTCCgGGTCGTTCTTC) (SEQ ID NO:30) encoding the sgRNA target sequence are annealed and subcloned via BbsI restriction digest into plasmid px458M that contains a U6 promoter-driven sgRNA and a SpCas9 expression cassette. The pX458M plasmid is modified from the pX458 plasmid (addgene #48138) (Ran F A, Hsu P D, Wright J, Agarwala V, Scott D A, et al. (2013) Genome engineering using the CRISPR-Cas9 system. Nature protocols 8: 2281-2308) and carries an optimized sgRNA scaffold (Chen B, Gilbert L A, Cimini B A, Schnitzbauer J, Zhang W, et al. (2013) Dynamic imaging of genomic loci in living human cells by an optimized CRISPR/Cas system Cell 155: 1479-1491.). The targeting activity of this plasmid is validated by T7E1 assay using 293 cells. iPSC47_36 cells are transfected with pX458M and a phosphorothioate-modified single stranded oligonucleotide (ssODN) donor template using TransIT-LT1 (Minis). The ssODN (FIG. 2) is designed to introduce the desired wildtype GBA1 sequence flanked by homology arms to the targeted genomic region. The ssODN is also designed to contain silent mutations to prevent retargeting by spCas9 and to introduce a BtgI restriction site to facilitate identification of targeted clones. Forty-eight hours post-transfection, GFP-positive cells are isolated by FACS and re-plated at cloning density (250-500 cells/well of a 6 well Matrigel-coated plate). Cells are re-plated and cultured for 4 days in mTeSR1 containing 10% CloneR (StemCell Technologies), using the manufacturer's recommended protocol. Cells were subsequently fed daily with mTeSR1 for an additional 9 days before colonies were manually harvested and expanded for genotyping. Primers VS4247 (gtgcgtaactttgtcgacagtcc) (SEQ ID NO:31) and VS4249 (ctgagagtgtgatcctgccaag) (SEQ ID NO:32) are used to PCR amplify the targeted GBA1 genomic region and products are subjected to BtgI digestion to identify putative edited clones. Corrected clones are subsequently confirmed by Sanger sequencing. The construction of gRNA, validation of gRNA editing activity and DNA sequencing are carried out by the CCHMC Transgenic Animal & Genome Editing Core using methods known in the art.

FACS isolation of VLA+NPCs and testing NPCs multipotency. GFP+ mouse iPSC-derived neural precursor cells (NPC) were produced as described (Sun, Y., et al. (2015) PLoS One 10(3): e0118771). The mouse NPCs are cultured in STEMdiff™ Neural Progenitor Medium (STEMCELL Technologies) and $1\times10^7$ mNPCs were labelled by anti-VLA4 antibody conjugated with APC (1: 50, Miltenyi Biotec, 130-102-142) in NPC culture medium for 30 min. The labeled cells are sorted by FACS in PBS. The sorted VLA4+cells are confirmed by staining with anti-VLA4 antibody. For neural differentiation, the VLA4+NPC are plated on a polyornithine and laminin-coated culture dish in complete StemPro® NSC SFM at $2.5-5\times10^4$ cells/cm² for 2 days and medium is changed, allowing differentiation: neuron differentiation medium (Neurobasal® Medium, B-27® Serum-Free Supplement, GlutaMAX™-I Supplement), aastrocyte differentiation medium (D-MEM with N-2, GlutaMAX™-I, and FBS), oligodendrocyte differentiation medium (Neurobasal® medium with B-27®, GlutaMAX™-I, and T3). The media is refreshed every 3-4 days (Sun, Y. et al. Properties of neurons derived from induced pluripotent stem cells of Gaucher disease type 2 patient fibroblasts: potential role in neuropathology. PLoS One 10, e0118771 (2015)).

Mice treatment and assessment of survival and body weight. To minimize mixed background interference with behavioral testing, Applicant has generated a C57BL/6 strain of 4L;C* mice by back-crossing to C57BL/6 WT mice for 10 generations. The C57BL/6 4L;C* mice developed the same neuronal phenotype with an average life span of ~56 days compared to ~48 days for mixed background (C57BL/6J/129SvEV) 4L;C* mice (Sun, Y. et al. Neuronopathic Gaucher disease in the mouse: viable combined selective saposin C deficiency and mutant glucocerebrosidase (V394L) mice with glucosylsphingosine and glucosylceramide accumulation and progressive neurological deficits. Hum Mol Genet 19, 1088-97 (2010).). These C57BL/6 4L;C* mice have a sufficient lifespan to allow IV tail injection and for use in this study. 4L;C* mice are transplanted with the NPCs by IV tail injection with $1\times10^6$ cells/injection, one IV/week, 2 IV/week or 3 IV/week, until end stage. 4L;C* mice are monitored following transplantation for body weight and clinical signs of disease. The mice are euthanized by sodium pentobarbital at the clinical end point when presenting difficulties in feeding, a clear downward trend of body weight loss, and severe paralysis, as previously described (Sun, Y. et al. Neuronopathic Gaucher disease in the mouse: viable combined selective saposin C deficiency and mutant glucocerebrosidase (V394L) mice with glucosylsphingosine and glucosylceramide accumulation and progressive neurological deficits. Hum Mol Genet 19, 1088-97 (2010).). Mice tissues are collected after transcardial perfusion with saline. Dissected tissues were either fixed in 4% paraformaldehyde (PFA) or snap-frozen for further analyses. The age at end point is analyzed for survival using Prizm software.

Survival and body weight change is shown in Table 1 and Table 2.

TABLE 1.

Survival Data

|  | mNPC 1×/WK | mNPC 2×/WK | mNPC 3×/WK | Vehicle (Saline) | Untreated |
|---|---|---|---|---|---|
| Range (days) | 61-62 | 60-63 | 60-64 | 56-62 | 51-62 |
| Average (days) | 61.5 | 61.2 | 61.4 | 57.8 | 56.2 |
| Percentage (vs saline) % | 106.4 | 105.9 | 106.3 | 100 | −2.7 |
| P value (vs saline) | 0.002 | 0.0202 | 0.003 |  | 0.0912 |

TABLE 2

Peak body weight data

|  | mNPC 1×/WK | mNPC 2×/WK | mNPC 3×/WK | Vehicle (Saline) |
|---|---|---|---|---|
| Age of the peak body weight (days) | 46 | 47 | 50 | 43 |

Neurobehavioral testing. Hindlimb clasping is tested by grasping the tail from base and lifting the mouse clear of all surrounding objects. The hindlimb position is observed for 30 seconds. Each mouse at each time point is tested in two trials, 10 mins apart between two trials, giving a score as follows. Score 0, hindlimbs are consistently splayed outward, away from the abdomen; Score 1, one hindlimb is retracted toward the abdomen for >50% of 30 seconds; score 2, both hindlimbs are partially retracted toward the abdomen for >50% of 30 seconds; and score 3, hindlimbs are entirely retracted and touching the abdomen for >50% of 30 seconds. Gait analyses was conducted to determine sensorimotor function. (Fleming, S. M. et al. Early and progressive sensorimotor anomalies in mice overexpressing wild-type human alpha-synuclein. J Neurosci 24, 9434-40 (2004).) Mice were trained to walk through a narrow alley leading into their home-cage. The mice are then brushed with non-toxic paint on the hind paws and placed at the beginning of the alley. As they walk into their home-cage they leave paw prints on the paper underneath. Stride length and base width are determined by measuring the distance between hind paw prints. The 4L;C* and control mice, untreated and non-4L;C* littermates are tested for gait at 40, 50 and over 50 days of age. The investigators performing the functional assessment are blind to the treatment.

Immunofluorescence. Immunofluorescence staining is performed on PFA fixed brains and cells. The brain sections are incubated in 0.3% Triton X-100 for 30 min, and treated with 50 mM $NH_4Cl$ in 1×PBS for 15 min followed by 1×PBS wash. The sections are blocked for 1 hr at RT in Blocking buffer (10% goat serum and 0.4% Triton X-100 in PBS). PFA fixed cells are incubated in blocking buffer (5% goat serum and 0.4% Triton X-100 in PBS) for 30-60 minutes. Following primary antibodies diluted in 5% goat serum is applied to the cells and brain sections overnight at 4° C. Rabbit anti-GFP (1:200, Cell Signaling Technology, 2956), rat anti-CD106 (VCAM-1) monoclonal Antibody (1:100, ebioscience, MR106), mouse anti-SOX2 (1:200, Millipore, AB5603), mouse anti-Nestin (1:100, Millipore, MAB353), mouse anti-integrin alpha 4 (VLA4) (1:100, Cell Signaling Technology, 8440S), mouse anti-TUJ1 (1:200, STEMCELL TECHNOLOGIES, 60052), mouse anti-O4 (1:100, Millipore, MAB365), mouse anti-NeuN antibody (1:500, Millipore, MAB377). After washing in PBS (3×10 min), the secondary antibodies: goat anti-mouse conjugated with Alexa Fluor® 594 (1:1000) for SOX2, Nestin, VLA4, Tuj 1, GFAP, and O4 detection, goat anti-rabbit conjugated with Alexa Fluor® 488 (1:1000) for GFP detection, and goat anti-rat conjugated with Alexa Fluor® 594 (1:1000) for VCAM detection, are applied. The cell and tissues sections are count-stained for nuclei with DAPI in mounting medium.

Immunohistochemistry. Frozen tissue sections fixed with 4% PFA are incubated with rat anti-mouse CD68 monoclonal antibodies (Serotec, mca1957) (1:3000 in PBS with 5% BSA) and mouse anti-GFAP monoclonal antibody (Roche #7604345). Detection is performed using Research IHC DAB XT and Research IHC Omni-UltraMap HRP XT Discovery XT Staining Module. ABC Vectastain and Alkaline Phosphatase Kit II (black) are used according to the manufacturer's instruction. The slides are counterstained with methylene green. Images are captured using a Zeiss microscope (Axioskop) equipped with SPOT Advance software (SPOT Diagnostic Instruments, Inc.). CD68-positive and GFAP-positive signal in brain sections are analyzed by Fiji software in randomly selected fields (300 mm6210 mm/field) from treated and saline control mice brains. Quantification data of the relative positive signal ratio is performed. Data collected from 10 images for each group).

Fluoro-Jade C (FJC) staining. FJC is a fluorescent dye derived from fluorescein used to label degenerating neurons. (Chidlow, G., Wood, J. P., Sarvestani, G., Manavis, J. & Casson, R. J. Evaluation of Fluoro-Jade C as a marker of degenerating neurons in the rat retina and optic nerve. Exp Eye Res 88, 426-37 (2009).) FJC staining and imaging analysis is performed on the frozen brain sections (25 µm). Prior to staining, sections are mounted on gelatin coated slides that were prepared by immersion in 1% pig skin gelatin solution (Sigma; gel strength 300, Type A) and dried overnight in an oven at 60° C. The sections mounted on gelatin slide are air dried for 30 min in a slide warmer at 50° C. Slides bearing tissue sections were first immersed in a solution consisting of 1% sodium hydroxide in 80% ethanol for 5 min, followed by rinsing for 2 min in 70% ethanol, 2 min in distilled water, and incubating in 0.06% potassium permanganate solution for 10 min. The tissue slides are then washed for 1-2 min in water and transferred for 10 min to a 0.0001% solution of FJ C (MILLIPORE, AG325) dissolved in 0.1% acetic acid. The slides are washed through three changes of distilled water for 1 min per change and air dried on a slide warmer at 50° C. for 5 min. The air-dried slides are dipped in xylene for 1 min and mounted with DPX (mixture of distyrene, a plasticizer, and xylene) non-fluorescent mounting media (Sigma).

Glycosphingolipids analysis. Tissue are homogenized in water and chloroform/methanol using a PowerGen 35 (Fisher Scientific) as described. (Sun, Y. et al. Substrate compositional variation with tissue/region and Gbal mutations in mouse models—implications for Gaucher disease. PLoS One 8, e57560 (2013).) Aliquots of the homogenates are processed for glycolipids extraction and analyzed for glucosylceramide and glucosylsphingosine by LC-MS at Medical University of South Carolina Lipidomics Shared Resource-Analytical Unit.

Oxygen consumption assay. Mouse brain mitochondria were isolated as described (Liou, B. et al. Modulating ryanodine receptors with dantrolene attenuates neuronopathic phenotype in Gaucher disease mice. Hum Mol Genet 25, 5126-5141 (2016)). To evaluate the mitochondrial function, OCR was measured and the data were analyzed using the XFe Wave software as described (Liou, B. et al. Modulating ryanodine receptors with dantrolene attenuates neuronopathic phenotype in Gaucher disease mice. Hum Mol Genet 25, 5126-5141 (2016)). ATP production rate in brain mitochondria was normalized to mg of mitochondrial protein (Dasgupta, N. et al. Neuronopathic Gaucher disease: dysregulated mRNAs and miRNAs in brain pathogenesis and effects of pharmacologic chaperone treatment in a mouse model. Hum Mol Genet 24, 7031-48 (2015)).

Quantitative real-time PCR. Total RNA from the mouse midbrain is isolated using an RNeasy Micro Kit (QIAGEN) including DNase treatment to remove potential genomic DNA contamination. The starting RNA (1000 ng) is quantified by spectrophotometric analysis (ND-100; NanoDrop, Thermo Scientific). Total RNA from mouse midbrain obtained from 3 animals for each condition (WT, NPCs treated and vehicle treated 4L;C* mice) is extracted as described. (Dasgupta, N. et al. Neuronopathic Gaucher disease: dysregulated mRNAs and miRNAs in brain pathogenesis and effects of pharmacologic chaperone treatment in a mouse model. Hum Mol Genet 24, 7031-48 (2015)). Total RNA is reverse transcribed into complementary DNA using random hexamers and Transcriptor Reverse Transcriptase (Roche Diagnostics). Real-time PCR is performed according to the manufacturer's protocol using TaqMan Gene Expression Assays and an ABI Prism 7000 Sequence Detection System (Applied Biosystems). The gene expression assays used were the following: Nt3 (Gene ID: 18205; neurotrophin 3), Bdnf (Gene ID: 12064; brain derived neurotrophic factor), Cntf (Gene ID: 12803; ciliary neurotrophic factor), Tgfb2 (Gene ID: 21808; transforming growth factor, beta 2), Cntfra (Gene ID: 12804; ciliary neurotrophic factor receptor), Igf1 (Gene ID: 16000; insulin-like growth factor 1), Jag1 (Gene ID: 16449; jagged 1), Lif (Gene ID: 16878; leukemia inhibitory factor), Tnf (Gene ID: 21926; tumor necrosis factor), Vegfa (Gene ID: 22339; vascular endothelial growth factor A), Vegfb (Gene ID: 22340; vascular endothelial growth factor B), Gdnf (Gene ID: 14573; glial cell line derived neurotrophic factor), Tnfα (Gene ID: 21926; tumor necrosis factor) and Fgf2 (Gene ID: 14173; fibroblast growth factor 2). Primers sequences are listed in Table 3. The reactions were performed in triplicate and gene expression Ct values were corrected for β-actin Ct values using the ΔΔCt method.

TABLE 3

Primers for qRT-PCR

|   | Primers (species) | Sequence (position) | |
|---|---|---|---|
| 1 | NT-3-F-qRT | 5'-ATGCAGAACATAAGAGTCAC-3' | SEQ ID NO: 1 |
|   | NT-3-R-Qrt | 5'-AGCCTACGAGTTTGTTGTTT-3' | SEQ ID NO: 2 |
| 2 | BDNF-F-qRT | 5'-GAAAGTCCCGGTATCCAAAG-3' | SEQ ID NO: 3 |
|   | BDNF-R-qRT | 5'-CCAGCCAATTCTCTTTTT-3' | SEQ ID NO: 4 |
| 3 | CNTF-F-qRT | 5'-GGCTAGCAAGGAAGATTCGT-3' | SEQ ID NO: 5 |
|   | CNTF-R-qRT | 5'-TCCCTTGGAAGGTACGGTAA-3' | SEQ ID NO: 6 |
| 4 | TGFb2-F-qRT | 5'-AAAATCGACATGCCGTCCCA-3' | SEQ ID NO: 7 |
|   | TGFb2-R-qRT | 5'-ATACCTGCAAATCTCGCCTC-3' | SEQ ID NO: 8 |
| 5 | CNTFRa-F-qRT | 5'-ATCCCCAATACCTTCAAT-3' | SEQ ID NO: 9 |
|   | CNTFRa-R-qRT | 5'-TATTCCTTCCCTGCGTAG-3' | SEQ ID NO: 10 |
| 6 | Igf1-F-qRT | 5'-GCTGGTGGATGCTCTTCAGT-3' | SEQ ID NO: 11 |
|   | Igf1-R-qRT | 5'-TAGGGACGGGGACTTCTGAG-3' | SEQ ID NO: 12 |
| 7 | Jag1-F-qRT | 5'-GAAAGACCACTGCCGTACCA-3' | SEQ ID NO: 13 |
|   | Jag1-R-qRT | 5'-CCCCGTAGTGACAAGGGTTC-3' | SEQ ID NO: 14 |
| 8 | Lif-F-qRT | 5'-AGCGCCAATGCTCTCTTCAT-3' | SEQ ID NO: 15 |
|   | Lif-R-qRT | 5'-CAGTGGGGTTCAGGACCTTC-3' | SEQ ID NO: 16 |
| 9 | Tnf-F-qRT | 5'-AGGCACTCCCCCAAAAGATG-3' | SEQ ID NO: 17 |
|   | Tnf-R-qRT | 5'-CCACTTGGTGGTTTGTGAGTG-3' | SEQ ID NO: 18 |
| 10 | Vegfa-F-qRT | 5'-CGATTGAGACCCTGGTGGAC-3' | SEQ ID NO: 19 |
|   | Vegfa-R-qRT | 5'-GCTGGCTTTGGTGAGGTTTG-3' | SEQ ID NO: 20 |
| 11 | Vegfb-F-qRT | 5'-GTGGTGCCATGGATAGACGTT-3' | SEQ ID NO: 21 |
|   | Vegfb-R-qRT | 5'-ATGCTCCCGGGGTAGAGTC-3' | SEQ ID NO: 22 |
| 12 | Fgf2-F-qRT | 5'-AAGCGGCTCTACTGCAAGAA-3' | SEQ ID NO: 23 |
|   | Fgf2-R-qRT | 5'-TGTAACACACTTAGAAGCCAGCA-3' | SEQ ID NO: 24 |
| 13 | GDNF-F-qRT | 5'-CAAAAATCGGGGGTGCGTTT-3' | SEQ ID NO: 25 |
|   | GDNF-R-qRT | 5'-GCCTTCTACTCCGAGACAGG-3' | SEQ ID NO: 26 |
| 14 | TGF-α-F-qRT | 5'-CCGGTTTTTGGTGCAGGAAG-3' | SEQ ID NO: 27 |
|   | TGF-α-R-qRT | 5'-CACCACTCACAGTGTTTGCG-3' | SEQ ID NO: 28 |

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating Gaucher disease in an individual in need thereof, comprising administering to said individual an Integrin α4β1, Very Late Antigen-4 positive neural precursor cell ("VLA4+NPC"), said VLA4+NPC being transfected with a lentivirus comprising wild type glucocerebrosidase (GCase).

2. The method of claim 1, wherein said Gaucher disease is characterized by reduced GCase activity and/or alpha synuclein aggregation.

3. The method of claim 1, wherein said Gaucher disease is caused or exacerbated by a GBA1 mutation.

4. The method of claim 1, wherein said Gaucher disease is type II nGD.

5. The method of claim 1, wherein said Gaucher disease is type III nGD.

6. The method of claim 1, wherein said NPC is derived from an iPSC, wherein said iPSC is derived from a human fibroblast.

7. The method of claim 1 wherein said VLA4+NPC is administered to said individual via intravenous administration.

8. The method of claim 1 wherein said lentivirus comprises a human elongation factor 1 alpha ("EF1α") promoter or an Ubiquitin C promoter (UbC).

9. The method of claim 1 wherein said VLA4+NPC is co-administered with a chaperone molecule.

10. The method of claim 1 wherein said VLA4+NPC is co-administered with a chaperone molecule selected from Dantrolene, Ambroxol, or a combination thereof.

11. The method of claim 1, wherein said VLA4+NPC is co-administered with an enzyme replacement therapy (ERT) selected from imiglucerase, velaglucerase alfa, taliglucerase alpha, or substrate reduction therapy (SRT) selected from eliglustat, miglustat, ibiglustat, or combinations thereof.

* * * * *

```
                          SEQUENCE LISTING

<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
atgcagaaca taagagtcac                                                   20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agcctacgag tttgttgttt                                                   20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gaaagtcccg gtatccaaag                                                   20

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
ccagccaatt ctcttttt                                                     18

<210> SEQ ID NO 5
<211> LENGTH: 20
<212> TYPE: DNA
<213> ORGANISM: Artificial Sequence
<220> FEATURE:
<223> OTHER INFORMATION: Primer
```

<400> SEQUENCE: 5
ggctagcaag gaagattcgt                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tcccttggaa ggtacggtaa                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aaaatcgaca tgccgtccca                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
atacctgcaa atctcgcctc                                               20

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
atccccaata ccttcaat                                                 18

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tattccttcc ctgcgtag                                                 18

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gctggtggat gctcttcagt                                               20

<210> SEQ ID NO 12

```
<211> LENGTH: 20
<212> TYPE: DNA
<213> ORGANISM: Artificial Sequence
<220> FEATURE:
<223> OTHER INFORMATION: Primer

<400> SEQUENCE: 12
tagggacggg gacttctgag                                                        20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gaaagaccac tgccgtacca                                                        20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ccccgtagtg acaagggttc                                                        20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
agcgccaatg ctctcttcat                                                        20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cagtggggtt caggaccttc                                                        20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
aggcactccc ccaaaagatg                                                        20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
```

```
ccacttggtg gtttgtgagt g                                              21

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cgattgagac cctggtggac                                                20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gctggctttg gtgaggtttg                                                20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
gtggtgccat ggatagacgt t                                              21

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
atgctcccgg ggtagagtc                                                 19

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
aagcggctct actgcaagaa                                                20

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
tgtaacacac ttagaagcca gca                                            23

<210> SEQ ID NO 25
<211> LENGTH: 20
<212> TYPE: DNA
```

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 25
caaaaatcgg gggtgcgttt                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gccttctact ccgagacagg                                               20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccggtttttg gtgcaggaag                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
caccactcac agtgtttgcg                                               20

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
caccgaagaa cgacccggac gcag                                          24

<210> SEQ ID NO 30
<211> LENGTH: 24
<212> TYPE: DNA
<213> ORGANISM: Artificial Sequence
<220> FEATURE:
<223> OTHER INFORMATION: Oligonucleotide for sgRNA

<400> SEQUENCE: 30
aaacctgcgt ccgggtcgtt cttc                                          24

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
gtgcgtaact ttgtcgacag tcc                                           23

```
<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
ctgagagtgt gatcctgcca ag                                              22

<210> SEQ ID NO 33
<211> LENGTH: 36
<212> TYPE: DNA
<213> ORGANISM: Artificial Sequence
<220> FEATURE:
<223> OTHER INFORMATION: gRNA WT

<400> SEQUENCE: 33
tgccagtcag aagaacgacc tggacgcagt ggcact                               36

<210> SEQ ID NO 34
<211> LENGTH: 36
<212> TYPE: DNA
<213> ORGANISM: Artificial Sequence
<220> FEATURE:
<223> OTHER INFORMATION: gRNA KI

<400> SEQUENCE: 34
tgccagtcag aagaacgatc tggatgccgt ggcact                               36

<210> SEQ ID NO 35
<211> LENGTH: 6
<212> TYPE: PRT
<213> ORGANISM: Artificial Sequence
<220> FEATURE:
<223> OTHER INFORMATION: Protein fragment

<400> SEQUENCE: 35

Cys Cys Arg Tyr Gly Gly
1               5

<210> SEQ ID NO 36
<211> LENGTH: 30
<212> TYPE: DNA
<213> ORGANISM: Artificial Sequence
<220> FEATURE:
<223> OTHER INFORMATION: Patient Strand

<400> SEQUENCE: 36
aagaacgacc cggacgcagt ggcactgatg                                      30

<210> SEQ ID NO 37
<211> LENGTH: 30
<212> TYPE: DNA
<213> ORGANISM: Artificial Sequence
<220> FEATURE:
<223> OTHER INFORMATION: Corrected Strand

<400> SEQUENCE: 37
aagaacgatc tggatgccgt ggcactgatg                                      30

<210> SEQ ID NO 38
<211> LENGTH: 23
<212> TYPE: DNA
<213> ORGANISM: Artificial Sequence
```

```
<220> FEATURE:
<223> OTHER INFORMATION: VS4247

<400> SEQUENCE: 38
gtgcgtaact ttgtcgacag tcc                                              23

<210> SEQ ID NO 39
<211> LENGTH: 22
<212> TYPE: DNA
<213> ORGANISM: Artificial Sequence
<220> FEATURE:
<223> OTHER INFORMATION: VS4249

<400> SEQUENCE: 39
ctgagagtgt gatcctgcca ag                                               22

<210> SEQ ID NO 40
<211> LENGTH: 130
<212> TYPE: DNA
<213> ORGANISM: Artificial Sequence
<220> FEATURE:
<223> OTHER INFORMATION: ssODN design
<220> FEATURE:
<221> NAME/KEY: modified base
<222> LOCATION: (2)..(2)
<223> OTHER INFORMATION: n is a, c, g, or t
<220> FEATURE:
<221> NAME/KEY: modified base
<222> LOCATION: (4)..(4)
<223> OTHER INFORMATION: n is a, c, g, or t
<220> FEATURE:
<221> NAME/KEY: modified base
<222> LOCATION: (6)..(6)
<223> OTHER INFORMATION: n is a, c, g, or t
<220> FEATURE:
<221> NAME/KEY: modified base
<222> LOCATION: (125)..(125)
<223> OTHER INFORMATION: n is a, c, g, or t
<220> FEATURE:
<221> NAME/KEY: modified base
<222> LOCATION: (127)..(127)
<223> OTHER INFORMATION: n is a, c, g, or t
<220> FEATURE:
<221> NAME/KEY: modified base
<222> LOCATION: (129)..(129)
<223> OTHER INFORMATION: n is a, c, g, or t

<400> SEQUENCE: 40
tncntncagc ccacttccca gacctcacca ttgccctcac cggtttagca cgaccacaac      60
agcagagcca tcgggatgca tcagtgccac ggcatccaga tcgttcttct gactggcaac    120 cagcncncnc                                                            130

<210> SEQ ID NO 41
<211> LENGTH: 30
<212> TYPE: DNA
<213> ORGANISM: Artificial Sequence
<220> FEATURE:
<223> OTHER INFORMATION: Allele 1

<400> SEQUENCE: 41
aagaacgatc tggatgccgt ggcactgatg                                       30

<210> SEQ ID NO 42
<211> LENGTH: 30
<212> TYPE: DNA
<213> ORGANISM: Artificial Sequence
<220> FEATURE:
<223> OTHER INFORMATION: Allele 2
```

```
-continued

<400> SEQUENCE: 42
aagaacgacc tggatgccgt ggcactgatg                                      30

<210> SEQ ID NO 43
<211> LENGTH: 41
<212> TYPE: DNA
<213> ORGANISM: Artificial Sequence
<220> FEATURE:
<223> OTHER INFORMATION: Forward Primer PLVX-GBA1-F

<400> SEQUENCE: 43
gagactagtt ctagagccac catggagttt tcaagtcctt c                         41

<210> SEQ ID NO 44
<211> LENGTH: 36
<212> TYPE: DNA
<213> ORGANISM: Artificial Sequence
<220> FEATURE:
<223> OTHER INFORMATION: Reverse Primer-PLVX-GBA1-R

<400> SEQUENCE: 44
cgcggccgct ctagatcact ggcgacgcca caggta                               36

<210> SEQ ID NO 45
<211> LENGTH: 41
<212> TYPE: DNA
<213> ORGANISM: Artificial Sequence
<220> FEATURE:
<223> OTHER INFORMATION: Forward Primer-FUGW-GBA1-F

<400> SEQUENCE: 45
tccccgggta ccggtgccac catggagttt tcaagtcctt c                         41

<210> SEQ ID NO 46
<211> LENGTH: 36
<212> TYPE: DNA
<213> ORGANISM: Artificial Sequence
<220> FEATURE:
<223> OTHER INFORMATION: Reverse Primer-FUGW-GBA1-R

<400> SEQUENCE: 46
atggtggcga ccggttcact ggcgacgcca caggta                               36
```